(12) United States Patent
Saidi et al.

(10) Patent No.: US 10,588,740 B2
(45) Date of Patent: Mar. 17, 2020

(54) NASAL IMPLANTS AND SYSTEMS AND METHODS OF USE

(71) Applicant: SPIROX, INC., Redwood City, CA (US)

(72) Inventors: Iyad S. Saidi, Dunn Loring, VA (US); Michael H. Rosenthal, Menlo Park, CA (US); Donald A. Gonzales, Austin, TX (US); J. Cameron Loper, Alexandria, VA (US); Marcus A. Hadley, Olney, MD (US); Jamie L. Ingram, Alexandria, VA (US); Cheng Q. Ren, Annandale, VA (US); Charles P. Luddy, Alexandria, VA (US); Leon A. Marucchi, Fairfax Station, VA (US); Bruce C. Gray, Belle Mead, NJ (US); R. Andrew Carlton, Arlington, VA (US)

(73) Assignee: SPIROX, INC., Menlo Park, CA (US)

( * ) Notice: Subject to any disclaimer, the term of this patent is extended or adjusted under 35 U.S.C. 154(b) by 0 days.

(21) Appl. No.: 15/339,220

(22) Filed: Oct. 31, 2016

(65) Prior Publication Data
US 2017/0079774 A1    Mar. 23, 2017

Related U.S. Application Data

(62) Division of application No. 14/192,365, filed on Feb. 27, 2014, now Pat. No. 9,480,594.
(Continued)

(51) Int. Cl.
*A61F 2/18* (2006.01)
*A61F 5/08* (2006.01)
(Continued)

(52) U.S. Cl.
CPC .......... *A61F 2/186* (2013.01); *A61B 17/3468* (2013.01); *A61F 5/08* (2013.01);
(Continued)

(58) Field of Classification Search
CPC .. A61F 2/18; A61F 2/186; A61F 5/08; A61M 29/00; A61M 5/31; A61L 27/18; A61L 27/58
See application file for complete search history.

(56) References Cited

U.S. PATENT DOCUMENTS

| 2,173,848 A | 9/1939 | Kraus |
| 3,395,709 A | 8/1968 | Rubin |

(Continued)

FOREIGN PATENT DOCUMENTS

| EP | 1216013 B1 | 6/2006 |
| EP | 1857078 A | 11/2007 |

(Continued)

OTHER PUBLICATIONS

Parylene Engineering; Why use parylene; retrieved from the internet (http://www.paryleneengineering.com/why_use_parylene.htm); 3 pages; on Oct. 2, 2017.
(Continued)

*Primary Examiner* — Yashita Sharma
(74) *Attorney, Agent, or Firm* — McDonnell Boehnen Hulbert & Berghoff LLP

(57) ABSTRACT

Described are implants for placing in a body, tools for delivering the implants, and systems and methods for using implants and tools for placing in a body and more particularly to nasal implants, tools for delivering nasal implants, and systems and methods for using such implants and tools. A tool may include a hand-held implant delivery device that cuts, holds, moves, orients, inserts, or shapes an implant. An implant may be a biodegradable, longitudinal implant that
(Continued)

may be oriented for implantation by an implant delivery device.

30 Claims, 72 Drawing Sheets

Related U.S. Application Data

(60) Provisional application No. 61/785,816, filed on Mar. 14, 2013, provisional application No. 61/770,008, filed on Feb. 27, 2013.

(51) Int. Cl.
*A61L 27/18* (2006.01)
*A61B 17/34* (2006.01)
*A61L 27/58* (2006.01)

(52) U.S. Cl.
CPC .............. *A61L 27/18* (2013.01); *A61L 27/58* (2013.01); *A61F 2/18* (2013.01); *A61F 2230/0008* (2013.01); *A61L 2430/34* (2013.01)

(56) References Cited

U.S. PATENT DOCUMENTS

| | | | |
|---|---|---|---|
| 3,716,058 A | 2/1973 | Tanner, Jr. | |
| 4,265,246 A | 5/1981 | Barry | |
| 4,461,281 A | 7/1984 | Carson | |
| 4,645,491 A | 2/1987 | Evans | |
| 4,938,234 A | 7/1990 | Capriotti | |
| 5,131,382 A | 7/1992 | Meyer | |
| 5,163,952 A | 11/1992 | Froix | |
| 5,254,106 A | 10/1993 | Feaster | |
| 5,261,916 A | 11/1993 | Engelson | |
| 5,286,254 A | 2/1994 | Shapland et al. | |
| 5,342,348 A | 8/1994 | Kaplan | |
| 5,356,431 A | 10/1994 | Pierce | |
| 5,358,522 A | 10/1994 | Montgomery et al. | |
| 5,411,550 A | 5/1995 | Herweck et al. | |
| 5,419,760 A | 5/1995 | Narciso | |
| 5,464,450 A | 11/1995 | Buscemi et al. | |
| 5,500,013 A | 3/1996 | Buscemi et al. | |
| 5,531,744 A | 7/1996 | Nardella et al. | |
| 5,533,440 A | 7/1996 | Sher | |
| 5,545,208 A | 8/1996 | Wolff et al. | |
| 5,551,954 A | 9/1996 | Buscemi et al. | |
| 5,591,227 A | 1/1997 | Dinh et al. | |
| 5,637,113 A | 6/1997 | Tartaglia et al. | |
| 5,649,977 A | 7/1997 | Campbell | |
| 5,679,400 A | 10/1997 | Tuch | |
| 5,683,448 A | 11/1997 | Cragg | |
| 5,730,744 A | 3/1998 | Justin et al. | |
| 5,735,811 A | 4/1998 | Brisken | |
| 5,749,893 A | 5/1998 | Vidal et al. | |
| 5,766,237 A | 6/1998 | Cragg | |
| 5,769,883 A | 6/1998 | Buscemi et al. | |
| 5,785,647 A | 7/1998 | Tompkins et al. | |
| 5,837,008 A | 11/1998 | Berg et al. | |
| 5,843,172 A | 12/1998 | Yan | |
| 5,891,108 A | 4/1999 | Leone et al. | |
| 5,893,840 A | 4/1999 | Hull et al. | |
| 5,897,523 A | 4/1999 | Wright et al. | |
| 5,951,586 A | 9/1999 | Berg et al. | |
| 5,972,027 A | 10/1999 | Johnson | |
| 5,980,551 A | 11/1999 | Summers et al. | |
| 5,980,564 A | 11/1999 | Stinson | |
| 5,980,566 A | 11/1999 | Alt et al. | |
| 6,010,054 A | 1/2000 | Johnson et al. | |
| 6,063,101 A | 5/2000 | Jacobsen et al. | |
| 6,071,305 A | 6/2000 | Brown et al. | |
| 6,099,561 A | 8/2000 | Alt | |
| 6,106,541 A | 8/2000 | Hurbis | |
| 6,165,210 A | 12/2000 | Lau et al. | |
| 6,183,433 B1 | 2/2001 | Bays | |
| 6,238,411 B1 | 5/2001 | Thorner | |
| 6,241,747 B1 | 6/2001 | Ruff | |
| 6,241,762 B1 | 6/2001 | Shanley | |
| 6,250,307 B1 | 6/2001 | Conrad et al. | |
| 6,258,056 B1 | 7/2001 | Turley et al. | |
| 6,268,405 B1 | 7/2001 | Yao et al. | |
| 6,290,673 B1 | 9/2001 | Shanley | |
| 6,293,967 B1 | 9/2001 | Shanley | |
| 6,322,590 B1 | 11/2001 | Sillers et al. | |
| 6,390,096 B1 | 5/2002 | Conrad et al. | |
| 6,401,717 B1 | 6/2002 | Conrad et al. | |
| 6,415,796 B1 * | 7/2002 | Conrad | A61F 5/566 128/898 |
| 6,431,174 B1 | 8/2002 | Knudson et al. | |
| 6,450,169 B1 | 9/2002 | Conrad et al. | |
| 6,454,803 B1 | 9/2002 | Romo | |
| 6,516,806 B2 | 2/2003 | Knudson et al. | |
| 6,656,195 B2 | 12/2003 | Peters et al. | |
| 6,878,165 B2 | 4/2005 | Makino | |
| 6,899,105 B2 | 5/2005 | Krueger et al. | |
| 6,978,781 B1 | 12/2005 | Jordan | |
| 6,982,359 B1 | 1/2006 | Beaudry | |
| 7,055,523 B1 | 6/2006 | Brown | |
| 7,114,495 B2 | 10/2006 | Lockwood | |
| D536,792 S | 2/2007 | Krueger et al. | |
| 7,213,599 B2 | 5/2007 | Conrad et al. | |
| 7,237,554 B2 | 7/2007 | Conrad et al. | |
| 7,322,356 B2 | 1/2008 | Critzer et al. | |
| 7,322,993 B2 | 1/2008 | Metzger et al. | |
| 7,337,781 B2 | 3/2008 | Vassallo | |
| 7,381,222 B2 | 6/2008 | Pflueger et al. | |
| 7,396,232 B2 | 7/2008 | Fromovich et al. | |
| 7,419,497 B2 | 9/2008 | Muni et al. | |
| 7,520,876 B2 | 4/2009 | Ressemann et al. | |
| 7,563,267 B2 | 7/2009 | Goldfarb et al. | |
| 7,666,203 B2 | 2/2010 | Chanduszko et al. | |
| 7,678,099 B2 | 3/2010 | Ressemann et al. | |
| 7,762,940 B2 | 7/2010 | Henderson et al. | |
| 7,780,730 B2 | 8/2010 | Saidi | |
| 7,842,062 B2 | 11/2010 | Keith et al. | |
| 7,879,061 B2 | 2/2011 | Keith et al. | |
| 7,905,889 B2 | 3/2011 | Catanese, III et al. | |
| 7,918,871 B2 | 4/2011 | Truitt et al. | |
| 7,992,566 B2 | 8/2011 | Pflueger et al. | |
| 8,104,478 B2 | 1/2012 | Pflueger et al. | |
| 8,133,276 B2 | 3/2012 | Saidi | |
| 8,167,787 B2 | 5/2012 | Gillis | |
| 8,241,266 B2 | 8/2012 | Keith et al. | |
| 8,267,962 B2 | 9/2012 | Stupak | |
| 8,277,478 B2 | 10/2012 | Drontle et al. | |
| 8,282,667 B2 | 10/2012 | Drontle et al. | |
| 8,348,969 B2 | 1/2013 | Keith et al. | |
| 8,409,250 B2 | 4/2013 | Schmieding et al. | |
| 8,568,439 B2 | 10/2013 | Keith et al. | |
| 8,585,728 B2 | 11/2013 | Keith et al. | |
| 8,585,729 B2 | 11/2013 | Keith et al. | |
| 8,623,043 B1 | 1/2014 | Keith et al. | |
| 8,657,846 B2 | 2/2014 | Keith et al. | |
| 8,678,008 B2 | 3/2014 | Rousseau et al. | |
| 8,784,488 B2 | 7/2014 | Saidi | |
| 8,801,670 B2 | 8/2014 | Drontle et al. | |
| 8,834,513 B2 | 9/2014 | Hanson et al. | |
| 8,882,795 B2 | 11/2014 | Drontle et al. | |
| 8,888,686 B2 | 11/2014 | Drontle et al. | |
| 8,915,938 B2 | 12/2014 | Keith et al. | |
| 8,944,990 B2 | 2/2015 | Hamel et al. | |
| 9,005,284 B2 | 4/2015 | Ressemann | |
| 9,101,739 B2 | 8/2015 | Lesch, Jr. et al. | |
| 9,192,748 B2 | 11/2015 | Ressemann et al. | |
| 9,278,199 B2 | 3/2016 | Keith et al. | |
| 9,282,986 B2 | 3/2016 | Hanson et al. | |
| 9,283,360 B2 | 3/2016 | Lesch et al. | |
| 9,320,876 B2 | 4/2016 | Ressemann et al. | |
| 9,333,327 B2 | 5/2016 | Setliff, III et al. | |
| 9,339,637 B2 | 5/2016 | Drontle et al. | |
| 9,370,650 B2 | 6/2016 | Hanson et al. | |
| 9,433,343 B2 | 9/2016 | Drontle et al. | |
| 9,440,049 B2 | 9/2016 | Drontle et al. | |
| 9,480,594 B2 | 11/2016 | Saidi et al. | |

(56) References Cited

U.S. PATENT DOCUMENTS

| | | |
|---|---|---|
| 9,486,614 B2 | 11/2016 | Drontle et al. |
| 9,550,049 B2 | 1/2017 | Hanson et al. |
| 9,597,220 B2 | 3/2017 | Gonzales et al. |
| 9,694,167 B2 | 7/2017 | Keith et al. |
| 9,700,705 B2 | 7/2017 | Lesch, Jr. et al. |
| 9,775,975 B2 | 10/2017 | Ressemann et al. |
| 10,022,525 B2 | 7/2018 | Hanson et al. |
| 10,029,069 B2 | 7/2018 | Keith et al. |
| 10,086,181 B2 | 10/2018 | Lesch et al. |
| 2002/0019670 A1 | 2/2002 | Crawley et al. |
| 2002/0173848 A1 | 11/2002 | Sachs |
| 2003/0028076 A1 | 2/2003 | Kuyava et al. |
| 2003/0149447 A1 | 8/2003 | Morency et al. |
| 2003/0199970 A1 | 10/2003 | Shanley |
| 2004/0098098 A1 | 5/2004 | McGuckin et al. |
| 2005/0004417 A1 | 6/2005 | Nelson et al. |
| 2005/0142162 A1 | 6/2005 | Hunter et al. |
| 2005/0154412 A1 | 7/2005 | Krueger et al. |
| 2006/0085027 A1 | 4/2006 | Santin et al. |
| 2006/0147492 A1 | 7/2006 | Hunter et al. |
| 2006/0184224 A1 | 8/2006 | Angel |
| 2006/0185680 A1 | 8/2006 | Bhat et al. |
| 2006/0241650 A1 | 10/2006 | Weber et al. |
| 2006/0276817 A1 | 12/2006 | Vassallo et al. |
| 2007/0173848 A1 | 7/2007 | Lennox et al. |
| 2007/0219575 A1 | 9/2007 | Mejia |
| 2007/0250118 A1 | 10/2007 | Masini |
| 2007/0277831 A1 | 12/2007 | Luhrs |
| 2007/0293946 A1 | 12/2007 | Gonzales et al. |
| 2008/0021495 A1 | 1/2008 | Lee et al. |
| 2008/0027480 A1* | 1/2008 | van der Burg ..... A61B 17/0401 606/199 |
| 2008/0066794 A1 | 3/2008 | Durfee |
| 2008/0077240 A1* | 3/2008 | Saidi .................. A61F 2/18 623/10 |
| 2008/0097335 A1 | 4/2008 | Trogden et al. |
| 2008/0167628 A1* | 7/2008 | Li ........................ A61F 2/95 604/264 |
| 2008/0172033 A1 | 7/2008 | Keith et al. |
| 2008/0208265 A1 | 8/2008 | Frazier et al. |
| 2008/0234818 A1 | 9/2008 | Kang et al. |
| 2008/0312688 A1 | 12/2008 | Nawrocki et al. |
| 2009/0024133 A1 | 1/2009 | Keady et al. |
| 2009/0024227 A1 | 1/2009 | Lesh |
| 2009/0099577 A1 | 4/2009 | Gonzales et al. |
| 2009/0198216 A1 | 8/2009 | Muni et al. |
| 2009/0204130 A1 | 8/2009 | Kantsevoy et al. |
| 2009/0274743 A1 | 11/2009 | Edelman et al. |
| 2009/0312791 A1 | 12/2009 | Lindh, Sr. et al. |
| 2009/0318875 A1* | 12/2009 | Friedman ........... A61B 17/3468 604/187 |
| 2010/0106255 A1 | 4/2010 | Dubin |
| 2010/0174138 A1 | 7/2010 | Chang et al. |
| 2010/0280611 A1 | 11/2010 | Saidi |
| 2011/0009872 A1 | 1/2011 | Mistry et al. |
| 2011/0251634 A1 | 10/2011 | Gonzales et al. |
| 2011/0264138 A1 | 10/2011 | Avelar et al. |
| 2012/0078367 A1 | 3/2012 | Hristov et al. |
| 2012/0215307 A1 | 8/2012 | Chen et al. |
| 2012/0310280 A1* | 12/2012 | Harrington ........ A61B 17/0401 606/232 |
| 2012/0323227 A1 | 12/2012 | Wolf et al. |
| 2012/0323232 A1 | 12/2012 | Wolf et al. |
| 2013/0096382 A1 | 4/2013 | Alexander et al. |
| 2013/0197303 A1 | 8/2013 | Chun et al. |
| 2013/0217958 A1 | 8/2013 | Mujwid et al. |
| 2013/0327333 A1 | 12/2013 | Ng et al. |
| 2014/0000631 A1 | 1/2014 | Gillis et al. |
| 2014/0188158 A1 | 7/2014 | Servell et al. |
| 2014/0243975 A1 | 8/2014 | Saidi et al. |
| 2014/0277429 A1 | 9/2014 | Kuzma et al. |
| 2014/0357959 A1 | 12/2014 | Hanson et al. |
| 2015/0012090 A1 | 1/2015 | Saidi |
| 2015/0051449 A1 | 2/2015 | Qiu |
| 2015/0066071 A1 | 3/2015 | Alexander et al. |
| 2015/0148612 A1 | 5/2015 | Schaeffer et al. |
| 2015/0148902 A1 | 5/2015 | Komrit |
| 2016/0058556 A1 | 3/2016 | Rosenthal et al. |
| 2016/0151614 A1 | 6/2016 | Ressemann et al. |
| 2016/0367286 A1 | 12/2016 | Drontle et al. |
| 2017/0007282 A1 | 1/2017 | Drontle |
| 2017/0028112 A1 | 2/2017 | Drontle et al. |
| 2017/0050001 A1 | 2/2017 | Drontle et al. |
| 2017/0105836 A1 | 4/2017 | Baron et al. |
| 2017/0113027 A1 | 4/2017 | Drontle et al. |
| 2017/0143532 A1 | 5/2017 | Gonzales et al. |
| 2017/0368319 A1 | 12/2017 | Lesch, Jr. et al. |
| 2018/0008806 A1 | 1/2018 | Ressemann et al. |
| 2018/0304051 A1 | 10/2018 | Keith et al. |
| 2018/0304058 A1 | 10/2018 | Hanson et al. |

FOREIGN PATENT DOCUMENTS

| | | |
|---|---|---|
| EP | 1475056 B1 | 10/2010 |
| EP | 1940320 B1 | 12/2010 |
| EP | 2692313 A | 2/2014 |
| EP | 2961350 B1 | 3/2018 |
| EP | 3400906 A1 | 11/2018 |
| WO | WO00/76493 A1 | 12/2000 |
| WO | WO01/01957 A1 | 1/2001 |
| WO | 01/21247 A1 | 3/2001 |
| WO | WO01/19301 A1 | 3/2001 |
| WO | WO2002/076354 A1 | 10/2002 |
| WO | WO03/015664 A1 | 2/2003 |
| WO | WO2003/041612 A2 | 5/2003 |
| WO | WO2006/093533 A1 | 9/2006 |
| WO | WO2006/101610 A2 | 9/2006 |
| WO | WO2006/107957 A2 | 10/2006 |
| WO | 2007/011994 A2 | 1/2007 |
| WO | 2007/134005 A1 | 11/2007 |
| WO | WO2007/134215 A2 | 11/2007 |
| WO | WO2008/042058 A1 | 4/2008 |
| WO | WO2009/036290 A1 | 3/2009 |
| WO | WO2010/033682 A1 | 3/2010 |
| WO | WO2010/051273 A1 | 5/2010 |
| WO | WO2010/059586 A1 | 5/2010 |
| WO | WO2010/132648 A1 | 11/2010 |
| WO | WO2011/092161 A1 | 8/2011 |
| WO | WO2012/112967 A1 | 8/2012 |
| WO | WO2014/004231 A1 | 1/2014 |
| WO | 2017/192394 A1 | 11/2017 |
| WO | 2018/053297 A1 | 3/2018 |
| WO | 2018/183561 A1 | 10/2018 |

OTHER PUBLICATIONS

De Pochat et al.; The role of septal cartilage in rhinoplasty: Cadaveric analysis and assessment of graft selection; Aesthetic Surgery Journal; 31(8); pp. 891-896; Nov. 2011.

Friedman et al.; A simplified technique for airway correction at the nasal valve area; Otolaryngol Head Neck Surg; 131(4); pp. 519-524; Oct. 2004.

Kalan et al.; Treatment of external nasal valve (alar rim) collapse with an alar strut; Journal of Laryngology and Otology; 115(10); pp. 788-791; Oct. 2001.

Karen et al.; The use of percutaneous sutures for graft fixation in rhinoplasty; Archives Facial Plastic Surgery; 5(2); pp. 193-196; Mar.-Apr. 2003.

Lambert et al.; A new method for arterial drug delivery via removable stent (abstract); JACC; 21(2); p. 483A; Abstract No. 834-2; Feb. 1993.

Millman; Alar Batten grafting for management of collapsed nasal valve; Laryngoscope; 112(3); pp. 574-579; Mar. 2002.

Pochat et al.; The role of septal cartilage in rhinoplasty: cadaveric analysis and assessment of graft selection; Aesthetic Surgery Journal; 31(8); pp. 891-896; Nov. 2011.

Rhee et al.; Nasal valve surgery improves disease-specific quality of life; Laryngoscope; 115(3); pp. 437-440; Mar. 2005.

Westreich et al.; Defining nasal cartilage elasticity: Biomechanical testing of the tripod theory based on a cantilevered model; Arch Facial Plast Surg; 9(4); pp. 264-270; Jul./Aug. 2007.

(56) References Cited

OTHER PUBLICATIONS

Cole; Biophysics of nasal air flow: A review; American Journal of Rhinology; 14(4); pp. 245-249; Jul./Aug. 2000.
Cole; The four components of the nasal valve; American Journal of Rhinology; 17(2); pp. 107-110; Mar./Apr. 2003.
Fanous et al.; Collapsed nasal-valve widening by composite grafting to the nasal floor; Journal of Otolaryngology; 25(5); pp. 313-316; Oct. 1996.
Friedman et al.; Nasal Valve Suspension: An Improved, Simplified Technique for Nasal Valve Collapse; Laryngoscope; 113(2); pp. 381-385; Jan. 2003.
Baron et al.; U.S. Appl. No. 15/274,986 entitled "Nasal implants and systems and method of use," filed Sep. 23, 2016.
Gonzales et al.; U.S. Appl. No. 15/423,345 entitled "Apparatus and methods for correcting nasal valve collapse," filed Feb. 2, 2017.
Kim et al.; Analysis of cartilage-polydioxanone foil composite grafts; Facial Plast. Surg.; 29(6): pp. 502-505; doi:10.1055/s-0033-1360593; (Author Manuscript); Dec. 2013.
The extended European search report dated Oct. 11, 2018 in European Patent Application No. 18156136.6, Applicant: Spriox, Inc., (7pages).
The extended European search report dated Oct. 19, 2016 in European Patent Application No. 14756699.6, Applicant: Spriox, Inc., (7pages).
Communication pursuant to Rules 70(2) and 70a(2) EPC dated Nov. 7, 2016 in European Patent Application No. 14756699.6, Applicant: Spriox, Inc., (1page).
Response to Search Opinion under Rules 70(2) and 70a(2) EPC dated May 16, 2017 in European Patent Application No. 14756699.6, Applicant: Spriox, Inc., (26pages).
Communication under Rule 71(3) EPC dated Oct. 18, 2017 European Patent Application No. 14756699.6, Applicant: Spriox, Inc., (5pages).
Notification of Reason(s) for Refusal dated Apr. 18, 2017 in Japanese Patent Application No. JP 2015-560308.
Notification of Reason(s) for Refusal dated Dec. 19, 2017 in Japanese Patent Application No. JP 2015-560308, (10pages).
Notification of Reason(s) for Refusal dated Jun. 26, 2018 in Japanese Patent Application No. JP 2015-560308, (10pages).
Decision to Grant a Patent dated Aug. 28, 2018 in Japanese Patent Application No. JP 2015-560308, (3pages).
PCT International Search Report for PCT/US2017/030201, Applicant: Entellus Medical Inc., Form PCT/ISA/210 and 220, dated Jul. 19, 2017 (4pages).
PCT Written Opinion of the International Search Authority for PCT/US2017/030201, Applicant: Entellus Medical Inc. Form PCT/ISA/237, dated Jul. 19, 2017 (6pages).
PCT International Preliminary Report on Patentability (Chapter I of the Patent Cooperation Treaty) for PCT/US2017/030201, Applicant: Entellus Medical, Inc., Form PCT/IB/326 and 373, dated Nov. 15, 2018 (8pages).
Decision on Appeal dated Oct. 26, 2018 in U.S. Appl. No. 14/331,805, Inventor(s): Iyad S. Saidi, (12pages).

\* cited by examiner

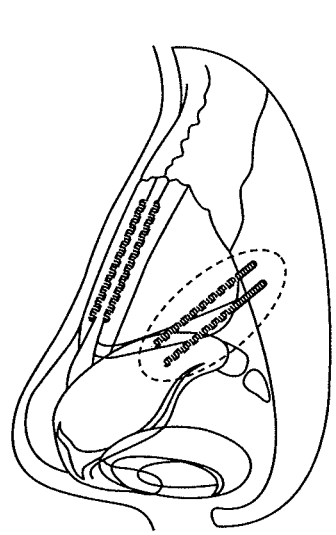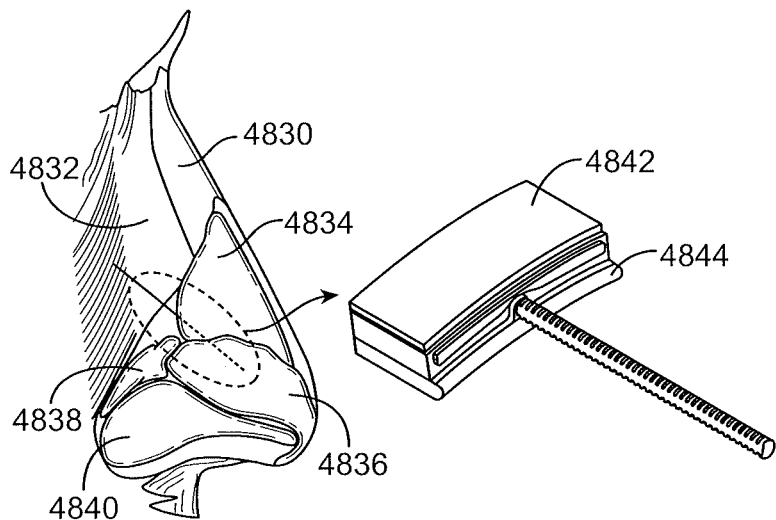
FIG. 1E  FIG. 1F  FIG. 1G
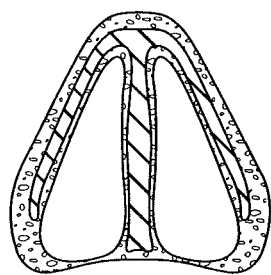
FIG. 1H
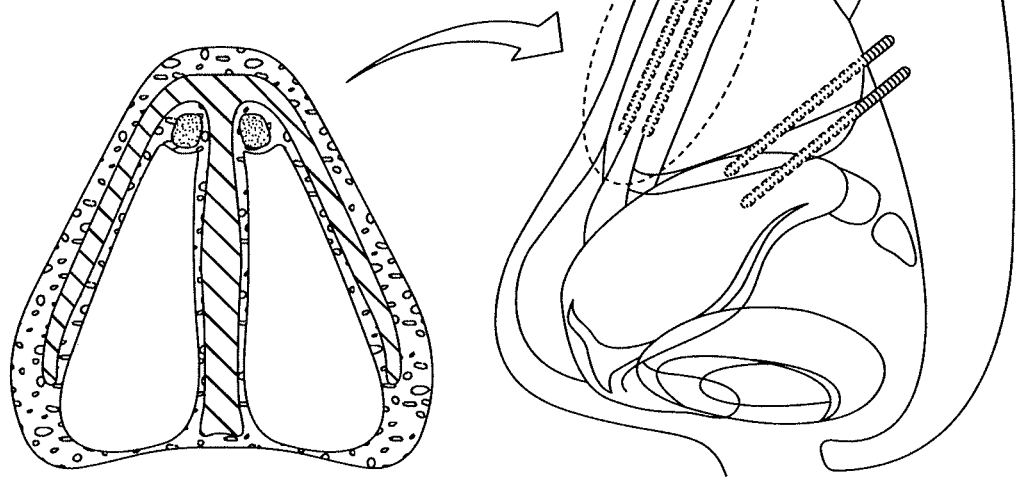
FIG. 1I  FIG. 1J

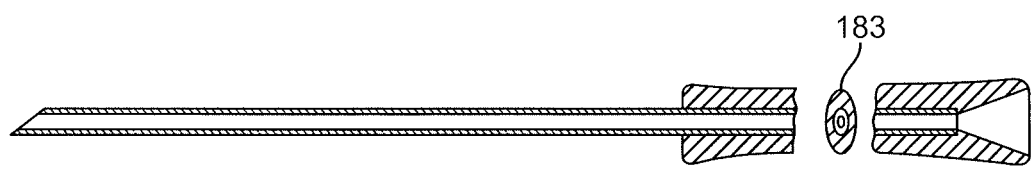
FIG. 6A
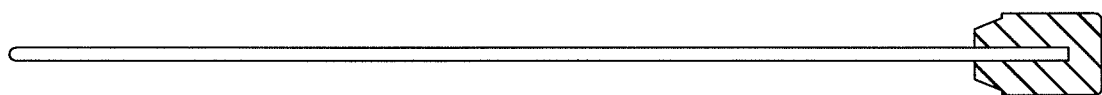
FIG. 6B
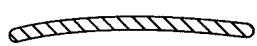   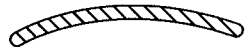   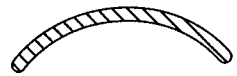
FIG. 6C         FIG. 6D         FIG. 6E

FIG. 10A
FIG. 10B
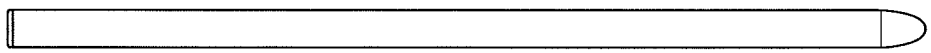
FIG. 10C
FIG. 10D
FIG. 10E
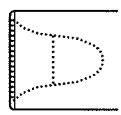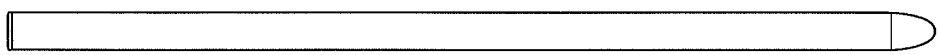
FIG. 10F
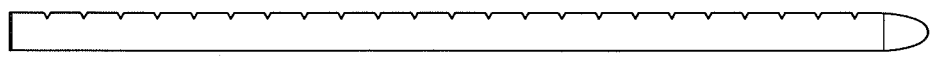
FIG. 10G
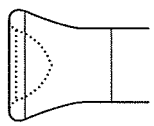
FIG. 10H

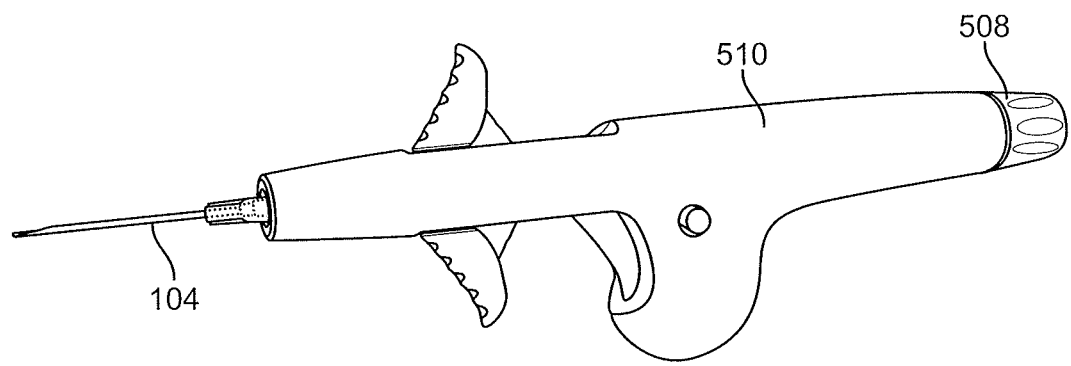
FIG. 12C
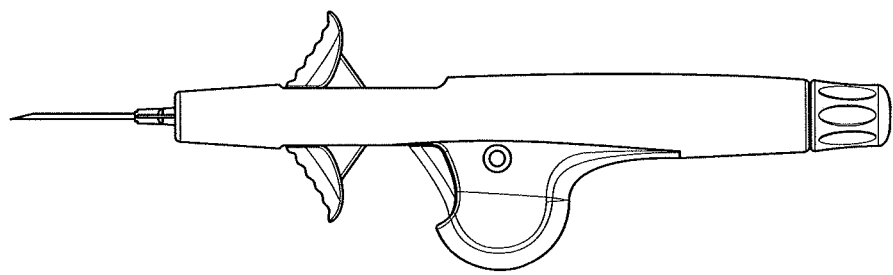
FIG. 13A
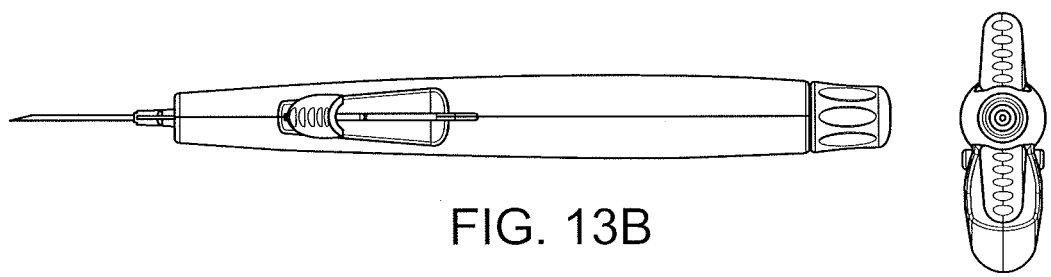 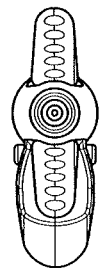
FIG. 13B        FIG. 13C
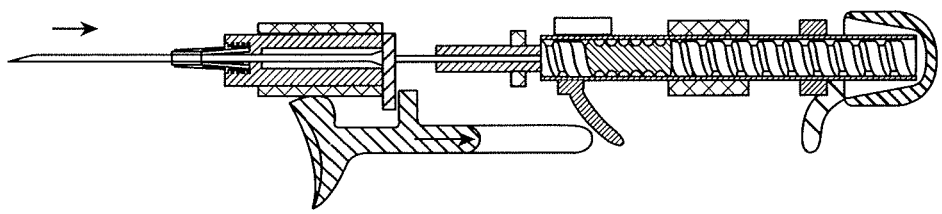
FIG. 14

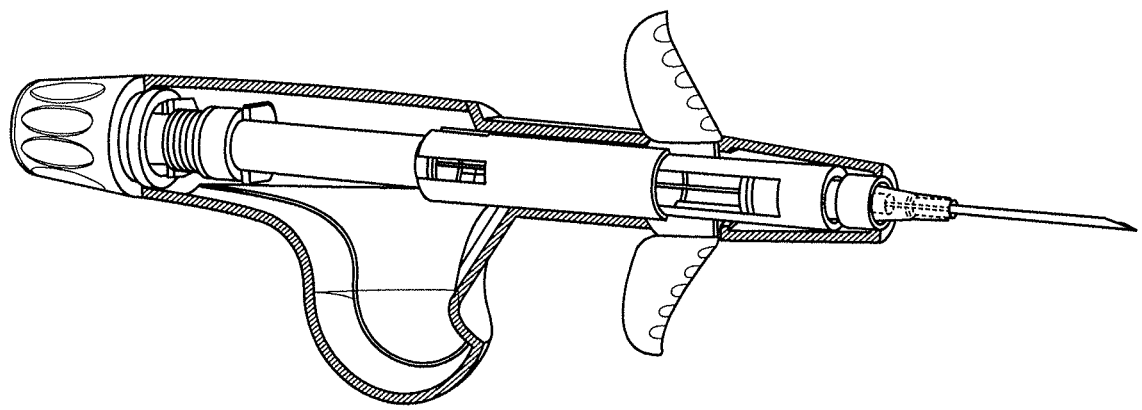
FIG. 15A
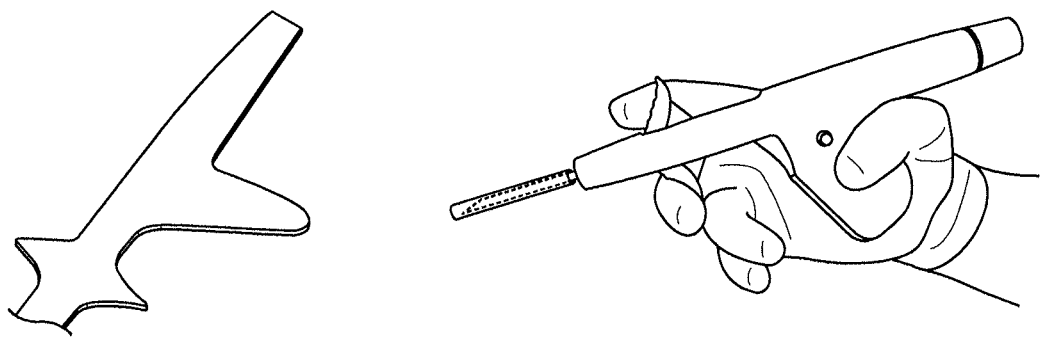
FIG. 15B
FIG. 15C
FIG. 16

Procedure Sequence
Preparation

Insertion

Insertion

Shaping

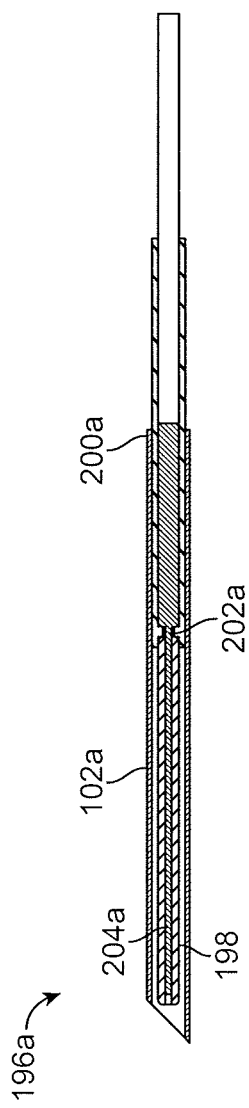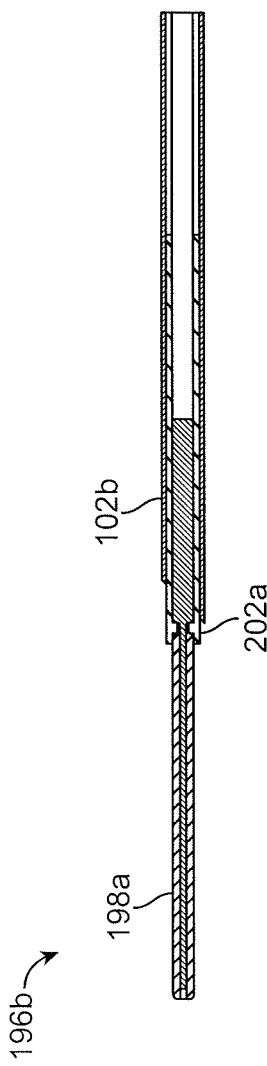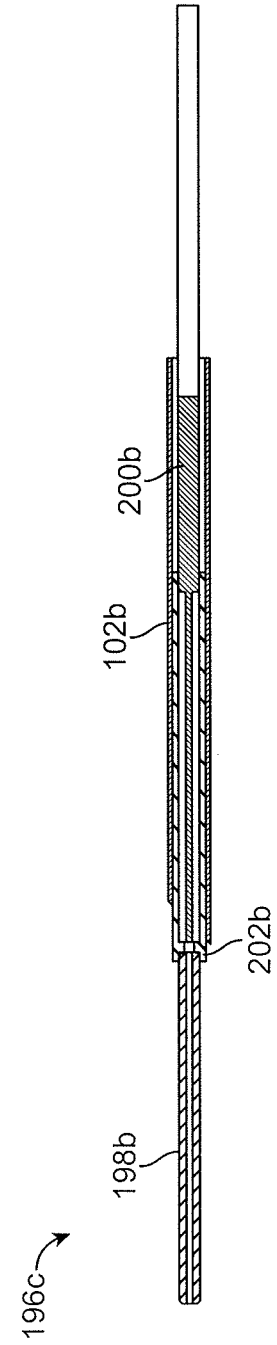

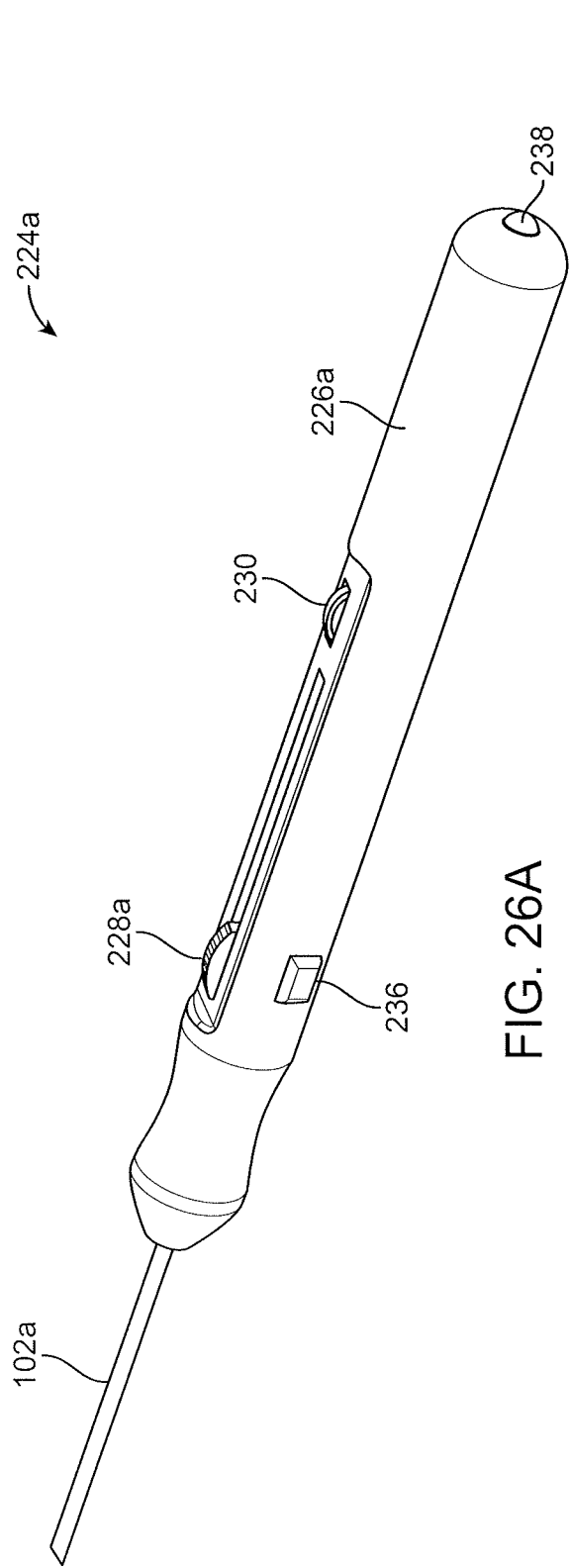
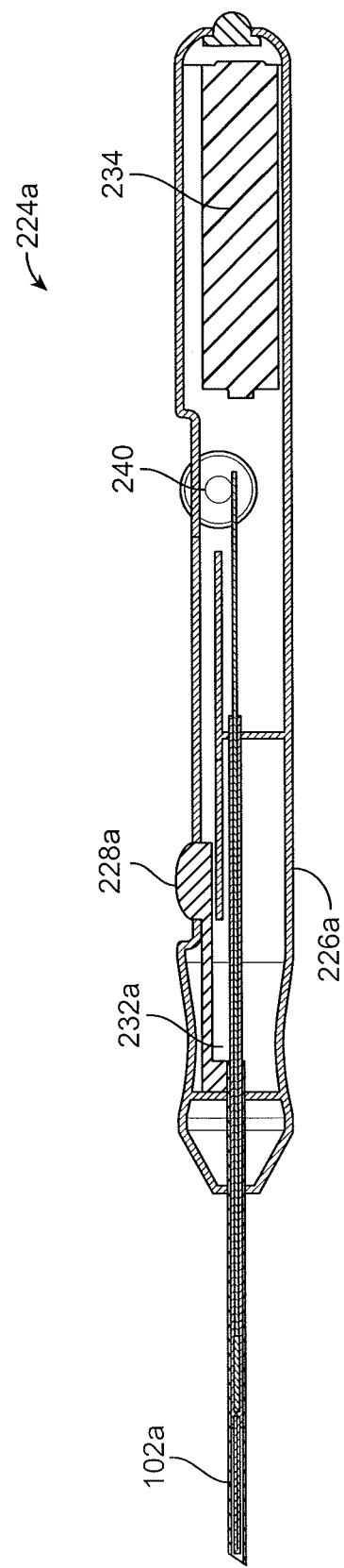
FIG. 26A
FIG. 26B

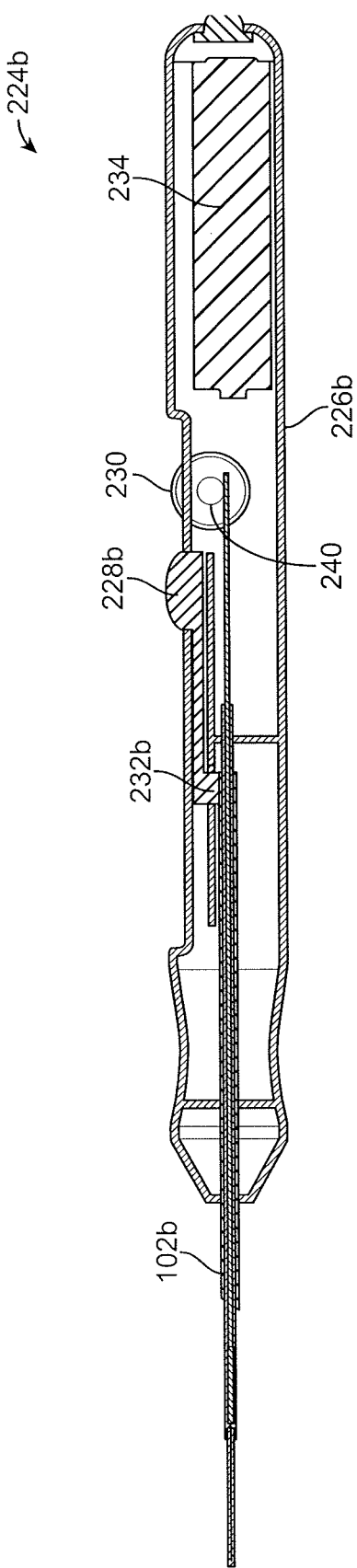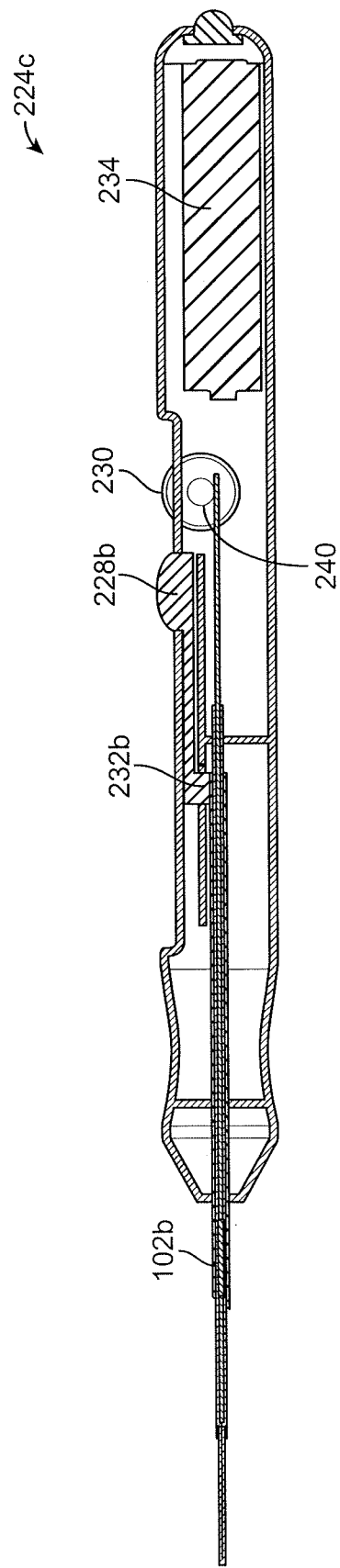
FIG. 26C
FIG. 26D

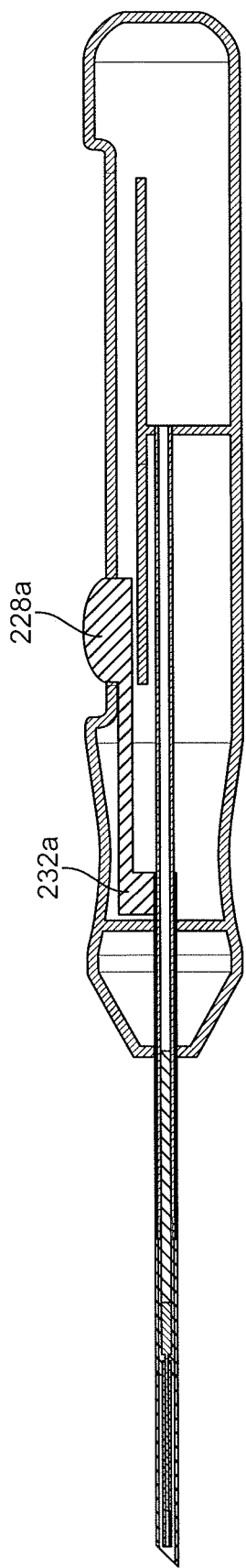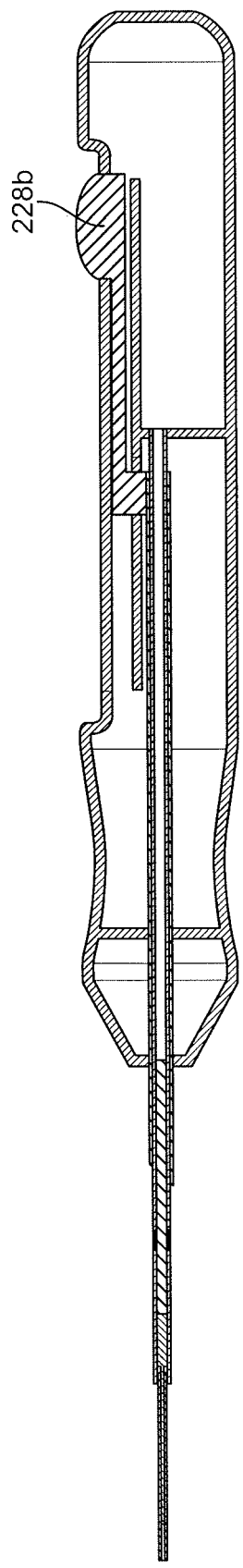
FIG. 27B
FIG. 27C

A

B

C

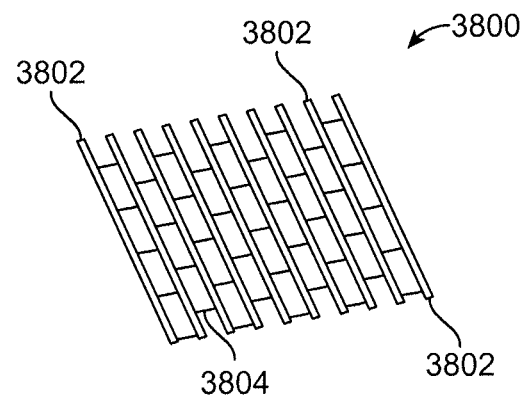
FIG. 38
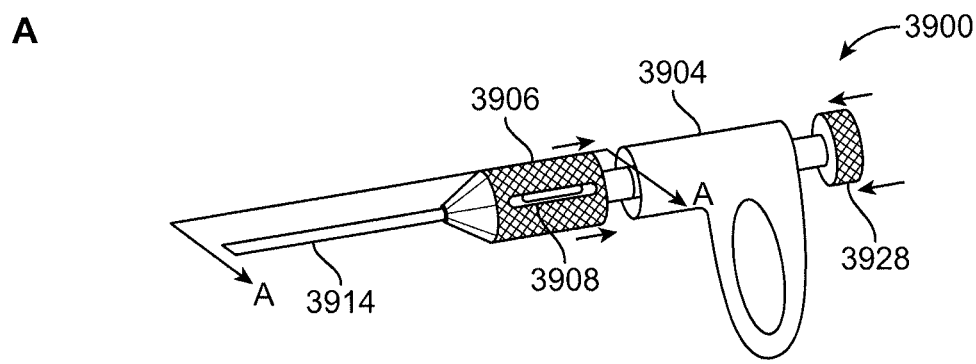
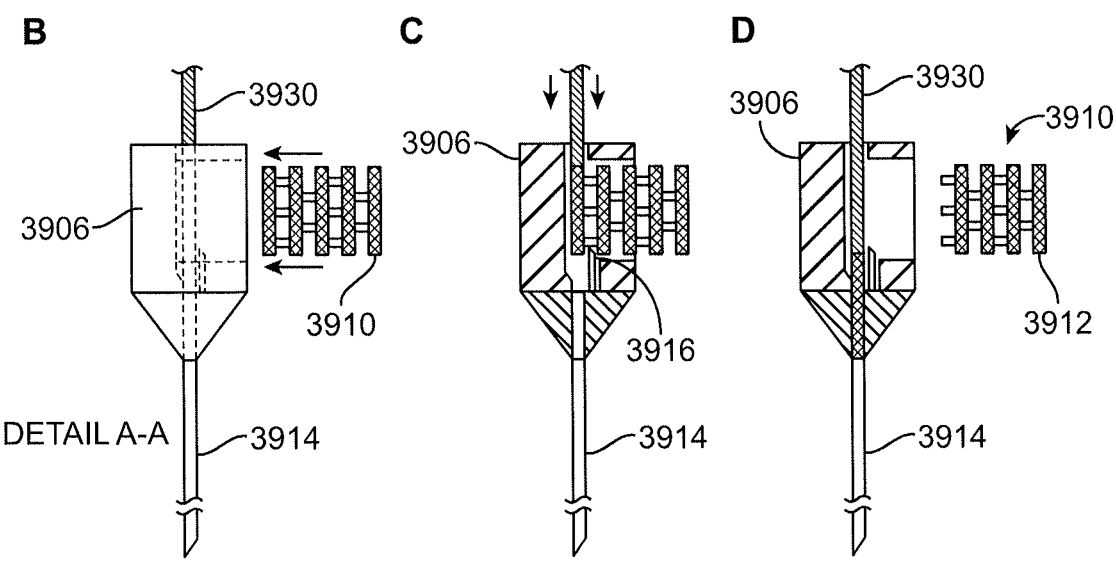
FIGS. 39A-39D

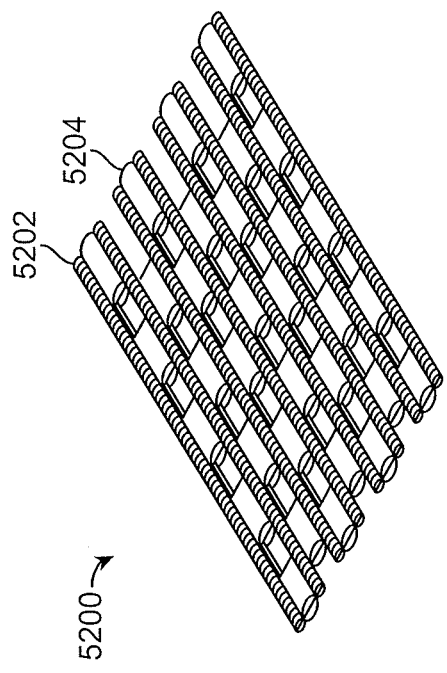
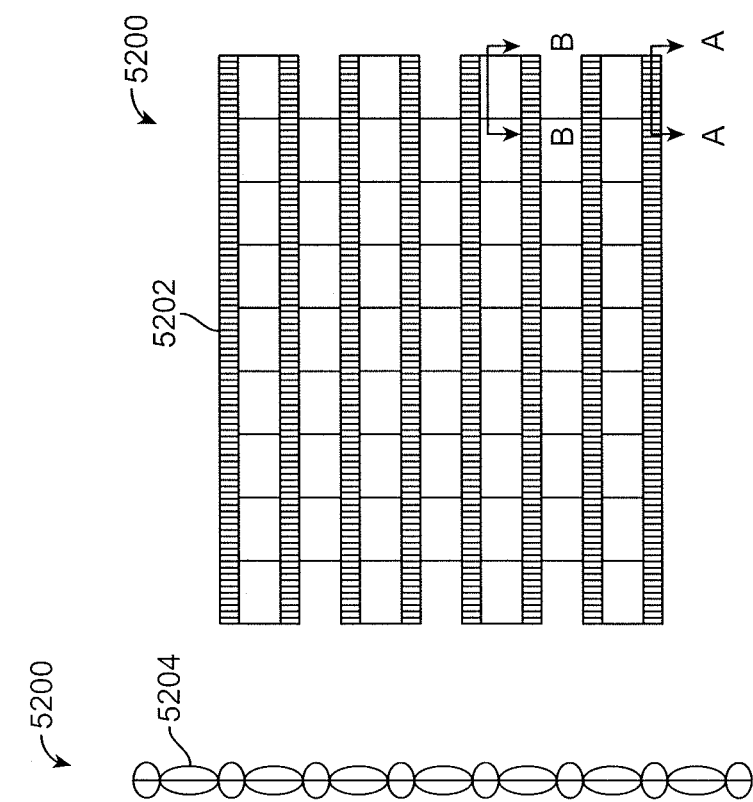
FIG. 52C
FIG. 52E
FIG. 52D
FIG. 52B
FIG. 52A

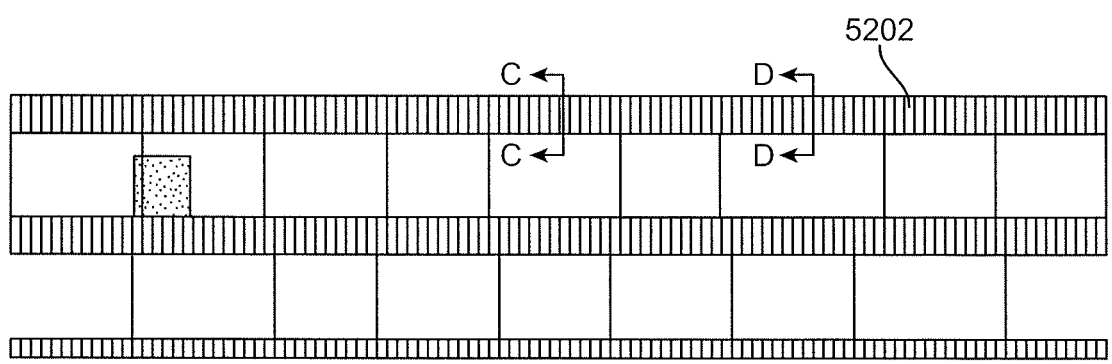
FIG. 52F
   
SECTION C-C    SECTION D-D
FIG. 52G    FIG. 52H

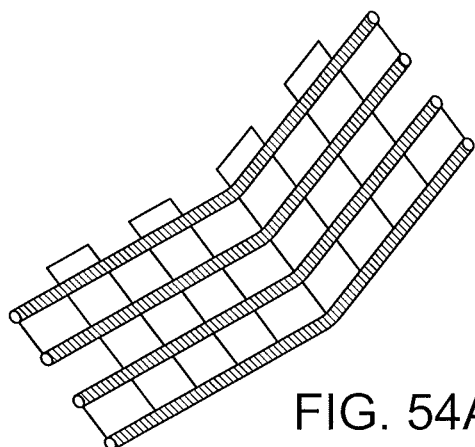
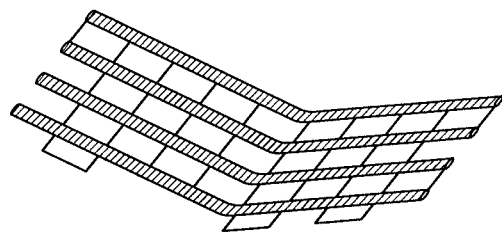
FIG. 54A
FIG. 54B
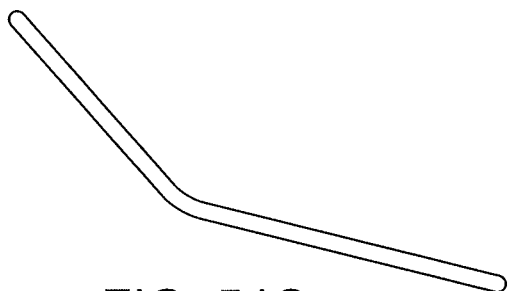
FIG. 54C
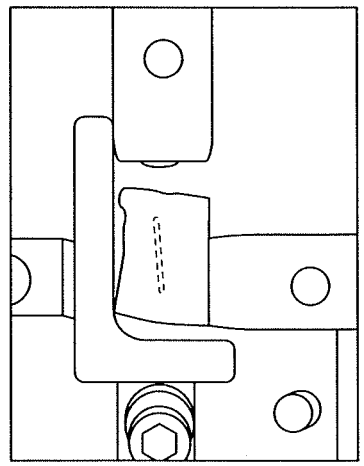
FIG. 55A
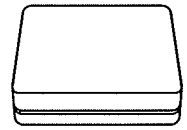
FIG. 55B
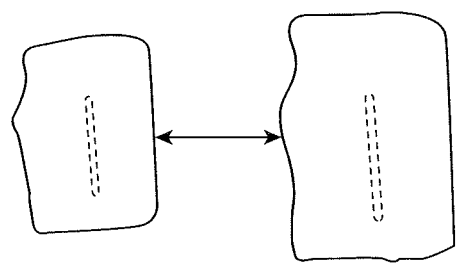
FIG. 56A    FIG. 56B

Material Samples Using During Testing

| Material | Shape | ID | OD | E [GPa] | I [m$^4$] | E·I [N-m$^2$] |
|---|---|---|---|---|---|---|
| Poly(L-Lactic) Acid, PLLA | Tube | 0.06 +/- 0.001" | 0.084 +/- 0.001" | 3.40 | 6.78E-03 | 2.30E-05 |
| Poly(l-lactide-co-d, l-lactide) Acid 70:30, PLLA-PDLA | Tube | 0.059 +/- 0.001" | 0.068 +/- 0.001" | 0.43 | 1.34E-04 | 5.76E-08 |
| Poly(L-Lactic-e-caprolactone) 70:30, PLLA-PCL | Tube | 0.073 +/- 0.001" | 0.092 +/- 0.001" | 0.04 | 2.66E-03 | 7.99E-08 |
| Poly(L-Lactic-glycolide) 82:18, PLLA-PGA | Rod | ------ | 0.029 +/- 0.001" | 3.40 | 1.45E-02 | 4.91E-05 |

FIG. 57

| Material | Temp. | Brittleness | Bend Force Required | Cool Off Time | Bend Results |
|---|---|---|---|---|---|
| PLLA-PGA | 22° C (room temperature) | No | Moderate | ---- | Relaxed back to 120° |
| | 37° C (body temperature) | No | Moderate | Immediate | Relaxed back to 120° |
| | 65° C | No | Very slight | 5 – 10 sec | Sample felt like "wet spaghetti" and firmly held its shape once it cooled |
| PLLA | 22° C (room temperature) | Slightly | Unbendable | ---- | Unbendable |
| | 37° C (body temperature) | Slightly | Unbendable | Immediate | Unbendable |
| | 65° C | Slightly | Very high | Immediate | Only able to bend slightly (~10°) |
| | 70° C | Slightly | High | 10 – 15 sec | Relaxed back to 100° Partial tube collapse |
| | 100° C | Slightly | Moderate | 10 – 20 sec | Relaxed back to 120° |
| | ~250° C (Heated by hot air gun) | Moderately (maybe due to high heat rate) | Slight | 10 – 20 sec | Held shape (only bent to 120°) |
| PLLA-PDLA | 22° C (room temperature) | No | Moderate | ---- | Bent to 90° Tube collapse |
| | 65° C | No | Moderate | Immediate | Bent to 90° Tube collapse |
| | 70° C | No | Moderate | 10 – 15 sec | Somewhat bendable Tube collapse |

FIG. 58

|  | | | | | |
|---|---|---|---|---|---|
|  | 100° C | No | Slight | 10 – 20 sec | Bendable Partial tube collapse |
|  | ~250° C (Heated by hot air gun) | No | Very slight | 10 – 20 sec | Sample collapsed due to thermal stresses |
| PLLA-PCL | 22° C (room temperature) | No | Very slight | ---- | Very bendable but relaxed back to original shape |
|  | 37° C (body temperature) | No | Very slight | Immediate | Very bendable but relaxed back to original shape |
|  | 65° C | Slightly | Very slight | Immediate | Very bendable but relaxed back to original shape |

FIG. 58 (Cont.)

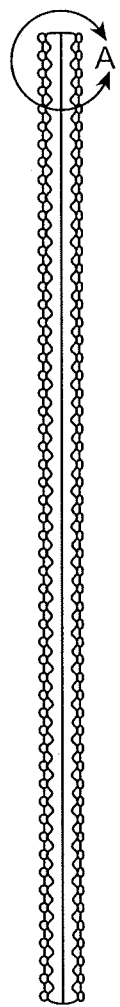
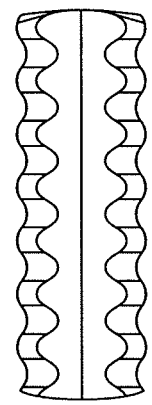
FIG. 62C
FIG. 62A   FIG. 62B
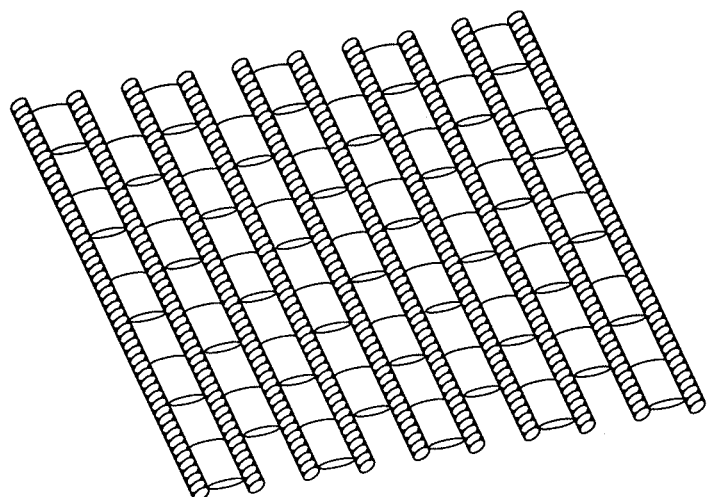
FIG. 62D

NASAL IMPLANTS AND SYSTEMS AND METHODS OF USE

CROSS REFERENCE TO RELATED APPLICATIONS

This application is a divisional of U.S. patent application Ser. No. 14/192,365, filed Feb. 27, 2014, which claims the benefit under 35 U.S.C. § 119 of U.S. Provisional Patent Application No. 61/770,008 filed Feb. 27, 2013 and U.S. Provisional Patent Application No. 61/785,816 filed Mar. 14, 2013, the disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention pertains to implants for placing in a body, tools for delivering the implants, and systems and methods for using implants and tools for placing in a body and more particularly to nasal implants, tools for delivering nasal implants, and systems and methods for using such implants and tools.

BACKGROUND

The particular nasal anatomy of an individual may cause or contribute to various problems, such as cosmetic concerns, difficulty breathing, sleep apnea, or snoring, and impact an individual's health or reduce the quality of life. For example, the structure of an external or internal nasal valve may resist airflow from the nose to the lungs and prevent an individual from getting sufficient oxygen to the blood.

U.S. Pat. Nos. 8,133,276, 7,780,730, and U.S. 2012/0109298 describe implants that can be introduced into the nasal region of an individual using non-surgical injection techniques for treating a nasal valve of an individual.

There is a continued need for improvements to address problems attributed to nasal anatomy that are easier to use, last longer, are less invasive, are less expensive to manufacture, work better and so on.

SUMMARY OF THE DISCLOSURE

Described herein are implants for placing in a body, tools for delivering the implants, and systems and methods for using implants and tools for placing in a body and more particularly to nasal implants, tools for delivering nasal implants, and systems and methods for using such implants and tools. These may be useful in minimally invasive procedures, including outpatient procedures, and may result in minimal pain and rapid recovery. These systems, assemblies and methods may be used, for example, in a doctor's office or clinic, and in some cases may require only a suitable local anesthetic. These implants, assemblies, systems, and methods may be especially useful for supporting or repairing nasal tissue, such as an internal nasal valve or an external nasal valve. Some implants may provide a long-term solution for improved nasal function or nasal cosmesis: a semi-permanent implant that degrades over a long time period may provide short-term nasal tissue support while the implant is intact and may initiate a body response (e.g. a fibrotic response) that strengthens nasal tissues and provides long-term nasal tissue support. A nasal treatment system may employ a pre-shaped or shapeable nasal implant including a bioresorbable material that provides structural support of surrounding nasal tissue. The assemblies and systems may penetrate through a patient's nasal tissue and allow precise positioning of an implant within a patient's nose.

One aspect of the invention provides a nasal implant delivery system including a delivery device and an implant. In some embodiments, the system includes a grippable housing with an implant delivery conduit having a piercing end configured to pierce a nasal tissue. In some embodiments, the conduit includes an interior orienting portion with a cross-sectional shape configured to orient an implant relative to the conduit. In some embodiments, the system includes a longitudinal implant including a resiliently deformable portion configured to have a contracted first shape and an expanded second shape. In some such embodiments, the first shape comprises a non-circular cross-section configured to orient the implant relative to the conduit by the conduit orienting portion when the implant is in place in the conduit. In some embodiments, the second shape includes an expanded shape configured to anchor the implant to nasal tissue when the implant is in place in the nasal tissue.

In some embodiments, the delivery device is configured to hold the implant near a distal end of the conduit when the implant is in the conduit. In some embodiments, the conduit is configured to hold the implant near a distal end of the conduit when the implant is in the conduit. In some embodiments, the conduit includes a 14 gauge, a 16 gauge, or an 18 gauge needle and the implant is configured to sit in the needle. In some embodiments, the delivery tool includes a window along its length configured to accept the implant into the conduit. In some embodiments, the delivery device is configured to hold the implant at a proximal side of a bevel on the distal end of the conduit when the implant is in the conduit. In some embodiments, the conduit cross-sectional shape includes an ellipse. In some embodiments, the conduit and implant are configured to provide a friction fit between the conduit and the implant when the implant is in the conduit.

In some embodiments, the resiliently deformable portion includes tines configured to have the contracted first shape and the expanded second shape. In some embodiments, the resiliently deformable portion includes tines at an end of the implant. In some embodiments, a length of the implant includes a plurality of repeating features. In some embodiments, the implant includes a plurality of ribs with alternating raised regions and depressed regions. In some embodiments, the implant includes a first end feature and a second end feature different from the first end feature. In some embodiments, the first end feature includes a rounded end. In some embodiments, the implant includes a biodegradable material. In some embodiments, the implant includes a biocompatible biodegradable poly-L-lactic acid (PLLA) or poly-D-lactic acid (PDLA). In some embodiments, the implant is configured to provide an implant flexural rigidity between $2.5e^{-6}$, and $1.5e^{-5}$.

Some embodiments include a stylet having a proximal graspable portion and a distal pushing portion configured to fit in the conduit. In some such embodiments, the stylet is configured move the implant through the conduit and into the tissue when the implant and the pushing portion are in place in the conduit and the pushing portion is moved through the conduit.

Another aspect of the invention provides a biodegradable longitudinal implant including a first end including a resiliently deformable portion configured to have a contracted first shape and an expanded second shape. In some embodiments, the first shape includes a non-circular cross-section configured to orient the implant relative to a delivery conduit in a nasal implant delivery device. In some embodiments, the second shape includes an expanded shape configured to anchor the implant to nasal tissue when the implant is in place in the nasal tissue. Some embodiments include a second end including a second feature different from the first feature. Some embodiments include a length therebetween the first end and the second end, including a plurality of repeating features. In some embodiments, the implant has an outer diameter less than 1.5 mm or less than 1.2 mm when in the contracted first shape.

In some embodiments, the implant is configured to provide an implant flexural rigidity between 2.5e-6, and 1.5e-5. In some embodiments, a length of the implant is less than 30 mm or less than 25 mm. In some embodiments, the resiliently deformable portion includes tines at an end of the implant. In some embodiments, the length includes a plurality of repeating features. In some embodiments, the length includes a plurality of ribs with alternating raised regions and depressed regions. In some embodiments, the first end feature includes a rounded end. In some embodiments, the implant includes a biocompatible biodegradable poly-L-lactic acid (PLLA) or poly-D-lactic acid (PDLA).

Another aspect of the invention provides system for placing an implant into a nasal tissue of a patient including an assembly with a grippable housing, a delivery conduit control mechanism, and an implant delivery conduit. In some embodiments, the implant delivery conduit includes a piercing end configured to pierce a body tissue. In some embodiments, the conduit configured to hold an implant and to place the implant in the body tissue. In some such embodiments, a movement of the delivery conduit is controllable by the delivery conduit control mechanism. In some embodiments, the delivery conduit control mechanism is configured to move the delivery conduit away from the implant and towards the housing without moving the implant.

Some embodiments include an implant pusher member configured to connect with an end of the implant in the delivery conduit. In some such embodiments, the implant pusher member is configured to control a position of the implant when the implant is in place in the conduit. In some embodiments, the delivery conduit control mechanism is further configured to move the conduit away from the implant pusher member.

Some embodiments include a first trigger member on an outside of the housing. In some such embodiments, the first trigger member is configured to be activated by a finger of a user. In some such embodiments, the activation moves the delivery conduit from a first position to a second position. In some such embodiments, the first trigger member is configured to move the delivery conduit into the housing when the trigger member is activated. In some embodiments, the trigger member is configured to be activated by a finger of a user pulling the trigger member. Some such embodiments include a handgrip proximal to the first trigger member. In some such embodiments, the handgrip is configured to be partially encompassed by a hand of the user when a finger of a user in place on the first trigger member. In some embodiments, the trigger arrangement and handgrip are further configured to be usable by either a left-handed person or a right-handed person. Some embodiments include a second trigger member on a generally opposite side from the first trigger member wherein the first trigger member and second trigger member are configured to be simultaneously pulled using fingers from a hand of a user.

In some embodiments, the implant pusher member is configured to hold the implant in place when the delivery conduit moves away from the implant. In some embodiments, a user controllable safety element is configured to hold the delivery conduit in an advanced position relative to the housing.

Some embodiments further include an implant, e.g., including a biodegradable material. Some such embodiments include an implant pusher member wherein the implant pusher member and implant comprise mating ends.

Some embodiments further include a support member connected with the grippable housing and configured to abut a face of a patient, e.g., such as when the delivery conduit is being retracted from the implant during assembly use.

Another aspect of the invention provides a method of implanting an implant into a nasal tissue of a patient. Some embodiments include the steps of loading an implant into a grippable housing, the housing including a delivery conduit control mechanism for controlling movement of a delivery conduit; attaching an implant delivery conduit with the housing; advancing the implant through the conduit until the implant is close to the distal end of the conduit; and piercing a nasal tissue with the piercing end of the implant delivery conduit by moving the implant delivery conduit through the nasal tissue; retracting the delivery conduit from the implant and into the grippable housing using the delivery conduit control mechanism to thereby leave the implant in place in the nasal tissue; and removing the implant delivery conduit from the patient. In some embodiments, movement of the conduit is controllable by the delivery conduit control mechanism.

Some embodiments include the step of releasing a user-controlled safety mechanism to thereby allow delivery conduit movement; and advancing the implant further to the end of the conduit. Some embodiments include the step of apposing the proximal end of the implant with an implant pusher member to thereby prevent movement of the implant relative to the delivery conduit during the retracting the delivery conduit step. In some embodiments, the housing is connected with a support member, the method further includes the step of contacting support member with a face of a patient to thereby hold the housing in place on the face of the patient during the retracting the delivery step.

Another aspect of the invention provides a method of deliver an implant to a nasal tissue. Some embodiments include the steps of placing a hollow delivery conduit holding a resiliently deformable implant having a first shape into a nasal tissue; and removing the hollow delivery conduit away from the implant to thereby change the implant into a second shape.

Another aspect of the invention includes a system for shaping an implant in a tissue in a body including a grippable housing including a delivery conduit control mechanism, an implant delivery conduit, and an energy delivery element. Some embodiments include a grippable housing including a delivery conduit control mechanism configured to control a delivery conduit movement. Some embodiments include an implant delivery conduit with a piercing end, the conduit connected with the delivery conduit control mechanism and configured to pierce a body tissue with the piercing end and place an implant in the tissue. Some embodiments include an energy delivery element configured to deliver energy to the implant when the implant and energy delivery element are in place in the tissue. Some embodiments include an energy source for delivering energy to the energy delivery element. Some embodiments include an energy source controller configured to control the energy delivered to the energy delivery device from the energy source.

Some embodiments further include an energy-responsive implant disposed within the implant delivery conduit and configured to change from a first shape to a second shape in response to an energy delivered from the energy delivery element. In some such embodiments, the energy-responsive implant is configured to change from a first shape to a second shape by conforming to a shape of a structure in the body tissue. In some embodiments, the energy-responsive implant comprises a heat-responsive biodegradable material. In some embodiments, the energy-responsive implant includes at least one of poly-L-lactic acid (PLLA) or poly-D-lactic acid (PDLA). In some embodiments, the energy-responsive implant includes an internal cavity configured to accept the energy delivery element. In some embodiments, the energy delivery element is configured to deliver heat to the implant. In some embodiments the delivery conduit control mechanism is configured to move the implant delivery conduit away from the energy-responsive implant to thereby place the implant in contact with nasal tissue.

Some embodiments further include an indicator configured to indicate a readiness of an energy source to deliver energy to the energy delivery element.

In some embodiments, the energy delivery element includes a flexible material configured to conform to a shape of the implant. In some embodiments, the energy delivery element includes a resistive wire configured to fit inside the implant. In some embodiments, the energy delivery element is configured to at least partially wrap around an implant when the element is in use. In some embodiments, the energy delivery element further includes a ribbon.

Some embodiments include an insulating material configured to separate the energy delivery element from the nasal tissue when the energy delivery element is in use to deliver energy to an implant.

In some embodiments, the implant delivery conduit is configured to at least partially retract inside the grippable housing. In some such embodiments, the energy delivery element is configured to travel from the grippable housing along an outside of the implant delivery conduit when the conduit is in a partially retracted position in the housing. In some such embodiments, the implant delivery conduit is further configured to travel past the piercing end of the implant delivery conduit and to thereby at least partially surround the implant. In some other embodiments, the energy delivery element further includes a clasping element configured to hold the energy delivery device to an outside of the implant delivery conduit. In some other embodiments, the energy delivery element further includes an insulating material configured to separate the energy delivery element from the tissue when the energy delivery element is in use for delivering energy to the implant.

Some embodiments include an energy delivery control mechanism connected with the housing and configured to move the energy delivery element relative to the body tissue or relative to an implant. In some such embodiments, the energy delivery control mechanism is further configured to move the energy delivery element relative to the housing. Some such embodiments include a pulley mechanism configured to pull the energy delivery element into the housing. Some embodiments include a user interface element on an outside of the housing configured to control an action of the energy delivery control mechanism to thereby control the energy delivery element in response to a user.

In some embodiments, the implant delivery conduit is configured to hold an implant within 10 mm of the piercing end during implant placement in the tissue.

Another aspect of the invention provides a method of changing a shape of a nose. Such a method may include the steps of inserting an energy-responsive implant having a first shape into a nasal tissue; inserting an energy delivery element into the nasal tissue; delivering energy from the energy delivery element to the energy-responsive implant to thereby increase a flexibility of the energy-responsive implant; shaping the energy-responsive implant into a second shape; removing energy from the energy-responsive implant to thereby hold it in the second shape; removing the energy delivery element from the nasal tissue apposing the energy-responsive implant having the second shape to a nasal tissue; and applying a force from the energy-responsive implant to the nasal tissue to thereby change the shape of the nose.

In some embodiments, the step of shaping the implant into a second shape includes conforming the implant to a shape of a portion of the nasal tissue. Some embodiments include the step of applying a force to the portion of the nasal tissue, e.g., to create a desired shape wherein shaping the implant includes conforming the implant to the desired shape of the portion of the nasal tissue. In some embodiments, the step of changing a shape of the nose includes changing the shape of a nasal valve.

Another aspect of the invention provides method of shaping a nasal implant in a nasal tissue. The method may include the steps of implanting an energy-responsive implant having a first shape into a nasal tissue; inserting an energy delivery element into an individual's nose; delivering energy from the energy delivery element to the implant to thereby increase a flexibility of the implant; shaping the implant to a second shape; and removing energy from the implant to thereby hold the implant in the second shape.

In some embodiments, the shaping step includes conforming the implant to a shape in the body. In some embodiments, the removing energy step includes decreasing a flexibility of the implant. In some embodiments, the delivering energy step includes heating the implant. In some such embodiments, delivering energy includes heating an implant material above the material glass transition temperature (Tg). Some embodiments include the step of moving the energy delivery element into contact with the implant prior to the delivering energy from the energy delivery element step. In some embodiments, the step of inserting an energy delivery element includes inserting an energy delivery element connected with a housing, the housing including a monitoring element, the method further including monitoring at least one of an intensity of the energy from the energy delivery element, a temperature of the implant, and a temperature of the nasal tissue. In some embodiments, the monitoring step includes using an open control loop process in the monitoring element. In some embodiments, the monitoring step includes using closed control loop process in the monitoring element.

Some embodiments further include the step of placing the implant in contact with a nasal tissue prior to the delivering energy from the energy delivery element step. Some embodiments further include the step of placing the implant in contact with a nasal tissue after the delivering energy from the energy delivery element step. In some embodiments, the steps of delivering the energy and shaping the implant comprises performing the steps simultaneously using a single tool. Some embodiments include repeating the delivering energy from the delivery element step, and the method further includes shaping the implant to a third shape. Some such embodiments include the step of removing energy from the implant to thereby hold the implant in the third shape.

Some embodiments include the step of implanting a second energy responsive implant into a nasal tissue and repeating the delivering energy from the energy delivery element to the implant to thereby increase a flexibility of the implant. Some such embodiments further include the step of shaping the implant to a second shape. Some such embodiments further include the step of removing energy from the implant to thereby hold the implant in the second shape on the second implant.

In some embodiments, the energy delivery element includes a flexible energy delivery element disposed along a length of the implant, and the shaping step further includes simultaneously shaping the energy delivery element and shaping the implant to a second shape wherein delivering energy comprises delivering energy during the shaping step.

In some embodiments, the shaping step includes placing pressure on the implant using a shaping instrument applied to at least one of the inside of the nose and the outside of the nose. In some embodiments, the shaping step includes placing pressure on the implant before and during the removing energy from the implant step. Some embodiments include the step of leaving the implant partially in the needle during the shaping the implant step. Some embodiments include repeating the delivering energy from the energy delivery element to the implant after the removing step, and the method further includes the step shaping the implant into a third shape.

In some embodiments, implanting further includes the steps of inserting a tip of the needle into the nose, the needle enclosing the implant and an implant pusher member; moving the needle, implant and implant pusher member through nasal tissue; retracting the needle proximally relative to both the implant pusher member and the implant; and retracting the implant pusher member away from the implant. Some such embodiments further include the steps of moving the energy delivery element relative to the implant after the moving the needle, implant and implant pusher member step; activating the energy delivery element; verifying a temperature of the energy delivery element; warming the implant; alerting the user when a set period of time has passed; shaping the implant; removing the energy source from the implant; maintaining a pressure on the implant to maintain an implant shape during the removing step; removing the pressure from the implant; verifying the shape of the implant; and removing the heating element from the implant without disturbing the position of the implant. Some embodiments include the step of maintaining the implant pusher member in place during the removing the energy delivery element step. Some such embodiments include the step of placing a shaping utensil in the nasal tissue and shaping includes shaping using the shaping utensil. Some embodiments include the step of verifying the shape of the implant after the shaping step.

Another aspect of the invention provides another method of shaping an implant in a nasal tissue, e.g., by heating the delivery conduit. Some embodiments include the steps of placing an implant delivery conduit encompassing an implant in the nasal tissue, wherein the implant comprises a first shape; heating a portion of the delivery conduit to thereby heat the implant; and after the heating step, shaping the implant into a second shape.

Some embodiments further include the step of retracting the implant delivery conduit from the nasal tissue and from the implant to thereby place the implant in contact with the nasal tissue after the shaping step. In some embodiments, the implant delivery conduit includes a needle generally concentric with and external to a cannula and the cannula includes an energy delivery element, the method further includes the step of partially retracting the needle away from the implant before the heating a portion of the delivery conduit step. Some such embodiments include the step of partially retracting the cannula before the shaping the implant step.

In some embodiments in which the implant delivery conduit includes a beveled needle, the method further includes heating the nasal tissue in the vicinity of the delivery conduit with the heated delivery conduit. In some embodiments in which the implant delivery conduit includes a heated internal portion, the method further includes insulating the nasal tissue from the heated internal portion. In some embodiments, the heating step includes heating the implant to a temperature at or above the glass transition temperature (Tg) of an implant material. In some embodiments, the heating step includes the step of heating the implant above body temperature but below the glass transition temperature (Tg) of an implant material.

Another aspect of the invention includes system for shaping an implant in a tissue in a body including a first grippable housing including an implant delivery conduit control mechanism; a second grippable housing including an energy delivery element control mechanism; and an energy delivery element. In some embodiments, the first grippable housing includes an implant delivery conduit control mechanism configured to connect with and move an implant delivery conduit relative to an energy-responsive implant, and the grippable housing configured to receive the implant delivery conduit and connectable with a joining element. In some embodiments, an implant delivery conduit is connected with the joining element and configured to hold an implant. Some embodiments include a second grippable housing including an energy delivery element control mechanism configured to connect with and move the energy delivery element relative to the implant, and further configured to deliver energy to the energy delivery element, the second housing connectable with a joining element. Some embodiments include a joining element connectable with the energy delivery element, the first grippable housing, and the second grippable housing. Some embodiments include an energy delivery element configured to delivery energy to an energy-responsive implant when the element and implant are in place. In some embodiments, the connector is configured to connect with only one of the first housing or the second housing at any given time.

Some embodiments include an energy responsive implant. Some embodiments include a power source connected with the second grippable housing.

Yet another aspect of the invention provides a method of shaping a nasal implant including at least partially encapsulating the implant with a flexible energy delivery device and delivering energy from the delivery device to the implant. Some embodiments include the steps of placing an energy-responsive implant into a nasal tissue; at least partially encapsulating the implant with a flexible energy delivery element configured to deliver energy to the implant;

delivering energy from the energy delivery element to the implant; and after the delivering step, shaping the implant into a desired shape.

In some embodiments, the flexible energy delivery element includes a flat strip, and the step of at least partially encapsulating includes placing the flat strip along an outside of the implant. In some embodiments, the implant includes an internal hollow region, and the step of at least partially encapsulating includes placing a resistive material inside the hollow region. In some embodiments, the step of at least partially encapsulating includes placing a resistive wire inside the internal hollow region, wherein the resistive wire configured to deliver heat to the implant. Some embodiments include an insulation element and the method further includes the step of insulating nasal tissue from energy coming from at least one of the implant and the energy delivery element. Some embodiments include the step of removing the flexible energy delivery element from the nasal region.

Yet another aspect of the invention provides a method of shaping a nasal implant in a nasal tissue, including inserting an energy delivery conduit holding an implant into a nasal tissue and retracting the conduit to expose the implant to an outside of the conduit, and delivering energy to the implant. The method may include the steps of inserting a energy delivery conduit into a nasal tissue, the conduit holding an energy-responsive implant having a first shape, the conduit having an energy delivery element disposed along an outside surface; retracting the conduit relative to the implant and relative to the energy delivery element to thereby expose a portion of the energy-responsive implant on an outside the conduit; placing the energy delivery element in proximity to the energy-responsive implant wherein the conduit holds a portion of the implant; delivering energy from the energy delivery element to the energy responsive implant to thereby increase an implant flexibility; applying a force to the implant to thereby change the implant from a first shape to a second shape; and removing energy from the implant to thereby hold it in the second shape.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1J show nasal tissue and various embodiments of implants for implanting in nasal tissue according to the disclosure.

FIGS. 6A and 6B show views of another embodiment of an implant delivery device for implanting a nasal implant into nasal tissue.

FIGS. 6C-6E show embodiments of implants that may be implanted such as by using the implant delivery device shown in FIGS. 6A and 6B.

FIGS. 10A-10J show embodiments of nasal implants and various implant features.

FIG. 12C shows another view of an embodiment of an implant delivery device.

FIGS. 13A-13C show different views of yet another embodiment of an implant delivery device for implanting a nasal implant into nasal tissue.

FIG. 14 shows a longitudinal cross-section view of another embodiment of an implant delivery device.

FIGS. 15A-15C show various embodiments of handle grips of implant delivery devices.

FIG. 16 shows another embodiment of an implant delivery device with a different handle grip.

FIGS. 25A-25C show another embodiment of a system using energy for shaping an implant in a tissue in a body.

FIGS. 26A-26D show another embodiment of a system using energy for shaping an implant in a tissue in a body.

FIGS. 27A-27G show another embodiment of a system using energy for shaping an implant in a tissue in a body.

FIG. 38 shows a sheet of implants connected by bridges.

FIGS. 39A-39D show an embodiment of a delivery tool for separating an implant from a sheet of implants, such as the sheet shown in FIG. 38, and for delivering the implant to a nasal tissue.

FIG. 48A is an end view of another sheet of nasal implants connected by bridges and openings that may allow for a needle and suture to pass through.

FIGS. 52A-52H show details of another sheet of nasal implants connected by bridges.

FIGS. 54A-54C show results of flexural rigidity from a flexed implant rod.

FIGS. 55A and 55B show results from a 1000 cycle test using a test fixture.

FIGS. 56A and 56B show results from testing the implant migration after manually flexing tissue for 5 minutes.

FIG. 57 shows a table of material property test results of candidate implants made into various shapes and sizes.

FIG. 58 shows a table of results from testing various material samples with heat for moldability and brittleness.

FIGS. 62A-62D show implants that may be formed as a long structure (FIG. 63D).

FIGS. 63A-63C show embodiments of different hand-held delivery tools with different types of hand-grips.

FIGS. 66A and 66B show placement of implants in a "spreader" region.

DETAILED DESCRIPTION

Figure 1A:
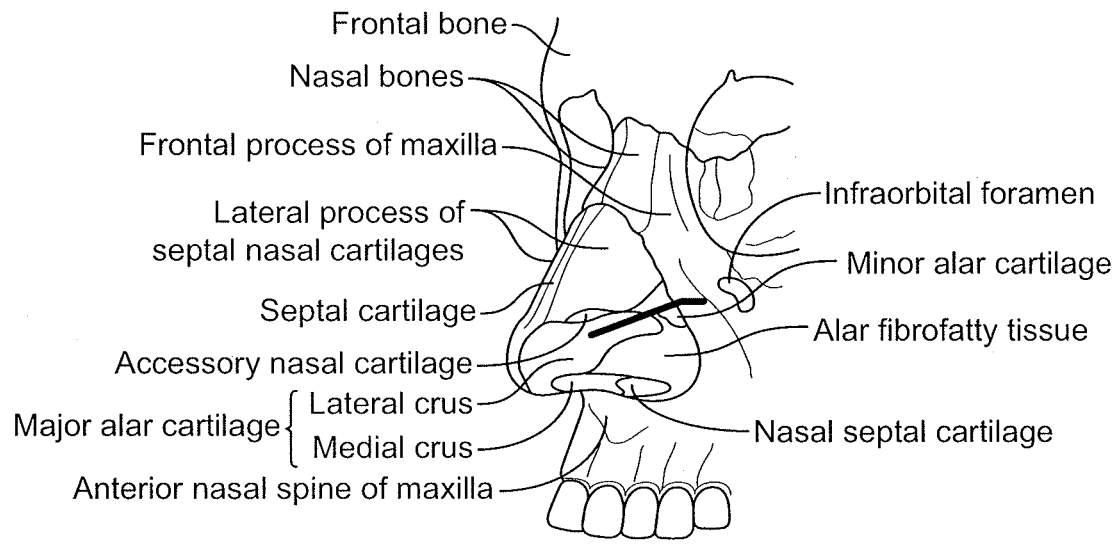

Various regions of airway tissue can impact airflow to the lungs. One major impact on airflow is from airflow resistance from the nose. The highest resistance structures in the nose may be the narrowest regions, such as the external nasal valve and the internal nasal valve. During normal inspiration, nasal valve cartilage around these valves prevents or reduces valve collapse and helps maintains airway patency. Incompetent internal and/or external valves can collapse and obstruct airflow during inhalation. Problems with the nasal septum, nasal turbinates, lateral cartilage, or other structures due to, for example, aging, poorly formed or weak cartilage, surgery (e.g. rhinoplasty, septoplasty) and/or trauma can lead to nasal valve problems and impact airflow.

Surgical treatments (e.g. submucosal resection of turbinates, septoplasty) have been used in the past to reduce the size of the turbinates or correct deviated septum or to repair the nasal wall in order to improve the nasal valves and airflow. These surgical treatments are invasive, uncomfortable and require significant time to recuperate. Furthermore, they do not readily address problems with the lateral cartilage wall. The lateral cartilage wall has been repaired, for example, by cartilaginous graft techniques using additional material (cartilage) from the nose or ear. In addition to the above mentioned limitations, these techniques are expensive (e.g. thousands of dollars), highly invasive, require a high level of surgical experience, have long, painful recovery times (e.g. 3 weeks of downtime), do not always work well and require a second surgical invasion site (into the nasal area or ear to obtain cartilage). Invasive nasal surgery is complicated by the ongoing need to use the surgical site for breathing. Thus, invasive surgical approaches are far from ideal. Non-surgical approaches for nasal valve collapse include strips or stent-like materials (e.g. "BreathRight", Breathe with EEZ, Nozovent") that are placed on or around the nose. These temporary, suboptimal approaches suffer from limited efficacy and poor cosmesis.

Provided herein are implants, assemblies, systems, and methods using implants, assemblies, and systems that may be used for supporting and repairing a body tissue. These may be useful in minimally invasive procedures, including outpatient procedures, and may result in minimal pain and rapid recovery. These systems, assemblies and methods may be used, for example, in a doctor's office or clinic, and in some cases may require only a suitable local anesthetic. These implants, assemblies, systems, and methods may be especially useful for supporting or repairing nasal tissue, such as an internal nasal valve or an external nasal valve. Some implants may provide a long-term solution for improved nasal function or nasal cosmesis: a semi-permanent implant that degrades over a long time period may provide short-term nasal tissue support while the implant is intact and may initiate a body response (e.g. a fibrotic response) that strengthens nasal tissues and provides long-term nasal tissue support. A nasal treatment system may employ a pre-shaped or shapeable nasal implant including a bioresorbable material that provides structural support of surrounding nasal tissue. The assemblies and systems may penetrate through a patient's nasal tissue and allow precise positioning of an implant within a patient's nose.

FIG. 1A shows the underlying structural anatomy and tissues of a face with the muscles and skin removed. Bones of the nose and the rest of the face are indicated. An implant may be placed apposed to, within or attached or connected to any of the nasal tissues or surrounding tissues. In some embodiments, an implant is placed within a nasal tissue. In some embodiments, an implant is partially within a nasal tissue and partially within a surrounding tissue (e.g., a maxilla).

Figures 1B, 1C, 1D:
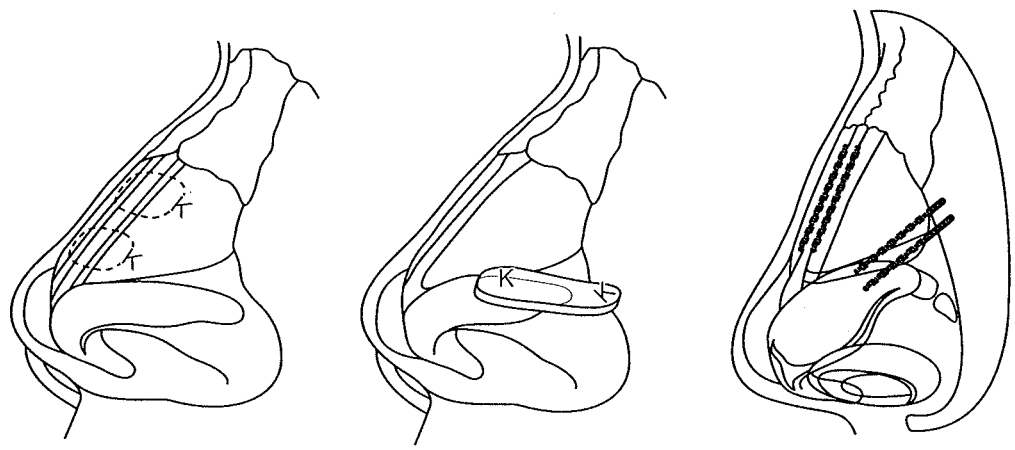

One aspect of the invention provides a nasal implant for nasal valve repair. Such a nasal implant may be used to strengthen or otherwise repair valves that previously may have been treated using a cartilage grafting technique. FIGS. 1B and 1C show prior implants used for internal valve repair. FIG. 1B shows a spreader graft implanted into a patient's nose. FIG. 1C shows an alar batten graft implanted into a patient's nose. FIG. 1D shows four implants according to one embodiment of the invention implanted into a patient's nose to strengthen the nasal valves in these same regions. Any type of implant may be used, such as any of those described herein or in U.S. Pat. Nos. 8,133,276, 7,780,730, and U.S. 2012/0109298. A method for using an implant may include the steps of moving the implant though the mucosa, passing the implant through the nasal region medial to the lateral cartilage, and passing the implant along the maxilla. An implant may additionally, or instead, be placed for treating a spreader region, submucosally, between the lateral cartilage and septal cartilage. In some embodiments, the implants are made of an absorbable material. They are implanted in positions that support the lateral wall cartilage and help resist or reduce movement of the cartilage during inhalation, thereby keeping the patient's airway open. As shown, the implants are positioned such that their distal most points are in close contact with the maxilla. The implant may be disposed between the maxilla and the overlying soft tissue (as shown in FIGS. 1F and 1G). FIG. 1F shows internal anatomy of a nose and a position (see oval in FIG. 1F) in which an implant can be placed. Note that the implant crosses (or lies adjacent to) one region that is substantially maxillary bone and another region that is substantially cartilage. FIG. 1G shows an implant in place in nasal tissue, such as in the position shown in FIG. 1F relative to nasal bone 4830, the frontal process of the maxilla 4832, the lateral cartilage 4834, the greater lateral cartilage 4836, the lesser alar 4838, and fibrofatty tissue 4840. Some of the nasal tissue has been cut away in FIG. 1F to illustrate the relationship of the implant relative to the nasal tissue in the region of the maxilla bone. In particular, the implant is leveraged between the maxilla bone 4844 below the implant and the soft tissue above the implant. Soft tissue above the bone (such as the periosteum, muscle, dermis 4842, etc.) may be tightly apposed to the bone. The soft tissue and the bone may envelope the implant and thereby hold it in place. An implant held in this manner provides leverage to other portions of the implant (e.g. those running through or near the lateral cartilage) to hold the implant in place and to provide support to the cartilage and to the nasal valve. This leverage may allow the implant to support lateral cartilage from collapse. The implant may be substantially prevented from rotating and/or from moving longitudinally. An implant may prevent inward movement of lateral cartilage upon inspiration, but cause no change in cosmesis.

Alternatively, the distal face of the implant may be simply placed in contact with the edge of the maxillary surface. In both cases, the proximal end of the implant may extend to a position under the lateral wall cartilage, as in a deep alar graft.

The implant may also be placed in the same position as the conventional spreader graft shown in FIG. 1B, i.e., between the top rim of the septal cartilage and the lateral wall cartilage to increase the angle of the lateral cartilage as it extends from the base of the nose. FIG. 1H shows a view looking into a patient's nostrils before placement of implants. FIGS. 1I and 1J show two implants that have been placed endonasally through the mucosa to wedge between lateral cartilage and the septum of the nose to increase the internal nasal angle.

As indicated above, the nose is organized into a complex 3-dimensional geometry with a wide variety of tissue types in a relatively small area. The 3-dimensional geometry is important for these tissues (and associated tissues not shown in these views) to carry out various functions, such as getting air (especially oxygen) to the lungs, warming the air, humidifying the air, and smelling odors—both good and bad—from food and other items. A nasal implant placed in the nose should improve (or maintain) nasal function and/or improve (or maintain) nasal appearance without causing unacceptable side effects. As such, placing the right implant into the right tissue in the complex 3-dimensional structure may provide these advantages. Controlling the short-term and long-term effects of an implant on the nasal tissues may also influence nasal implant success. An implant optimally sized and optimally shaped to fit into the particular nasal tissue to have the desired effect may provide particular success. An implant that fits into or even conforms to the shape of a particular nasal tissue being treated (e.g. changed or supported) may be especially beneficial in some cases. Provided herein are implants, assemblies, systems, and methods using such implants, assemblies, and systems, that may be used to control the initial placement of an implant into a tissue area of interest or provide an implant especially suitable for short-term or long-term success in improving (or maintaining) nasal function and/or nasal appearance.

FIGS. 2A-2B, 3A-3B, 4A-4B, 5A-5B, and 6A-6E show simple nasal implant systems and variations for inserting an implant into a nasal tissue.

Figure 2A:
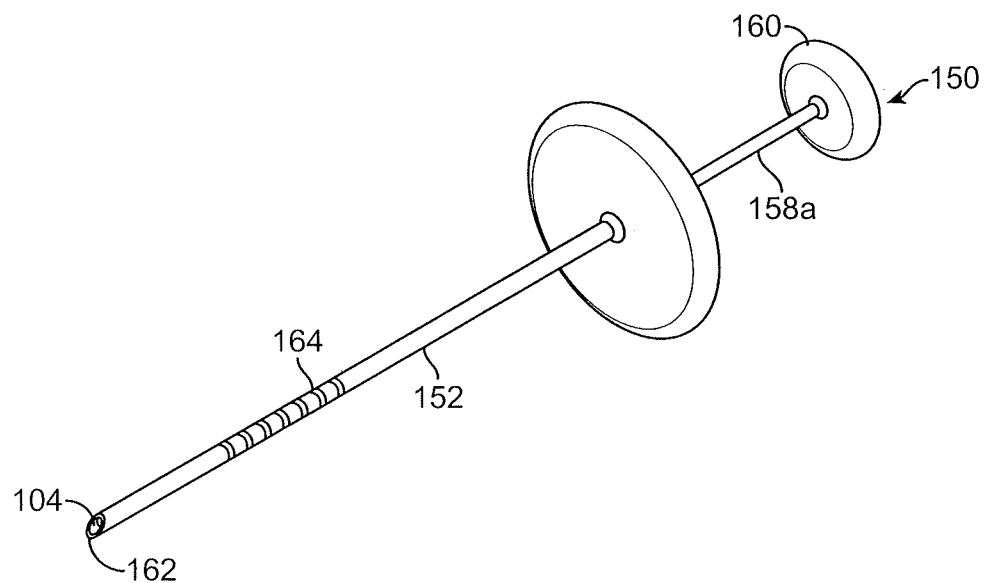
FIGS. 2A and 2B show different views of embodiment of an implant delivery device for implanting a nasal implant into nasal tissue.
Figure 2B:
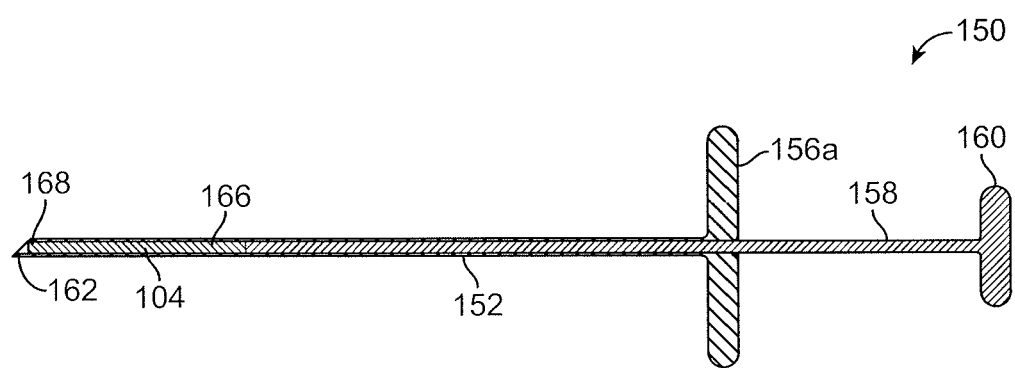
Figure 3A:
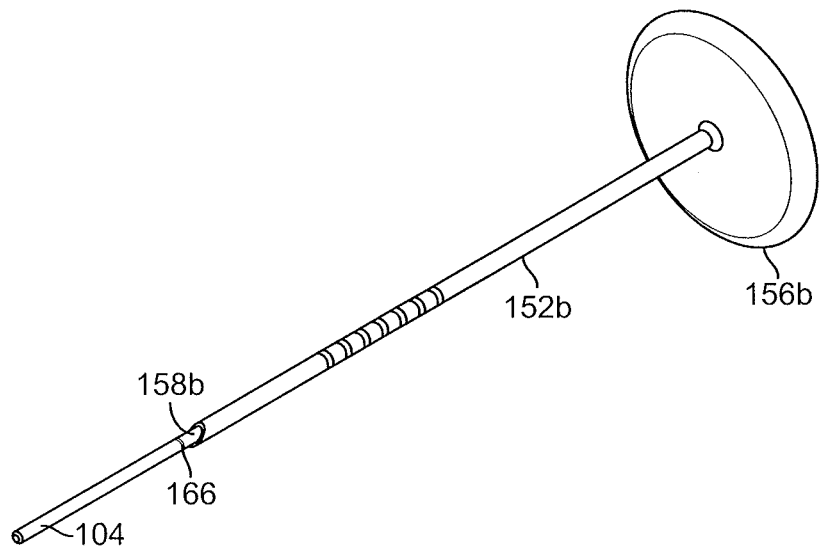
FIGS. 3A and 3B show different views of another embodiment of an implant delivery device for implanting a nasal implant into nasal tissue.

FIGS. 2A-2B and FIGS. 3A-3B show a nasal implant system in use. FIG. 2A (perspective view) and FIG. 2B (longitudinal cross-sectional view) show a nasal implant system in preparation for, or in the process of moving through, nasal tissue for placing an implant in a nasal tissue. (Nasal tissue is not shown in this view). FIG. 3A (perspective view) and FIG. 3B (longitudinal cross-sectional view) show the same nasal implant system as it appears after the implant was placed in the nasal tissue. The nasal implant system may include a delivery needle, a stylet, and an implant.

FIGS. 2A-2B show a system 150 including a hollow delivery needle 152 for placing implant 104 into a nasal tissue. Hollow delivery needle 152 has piercing end 162 for penetrating the tissue for placement. Hollow needle 152 may be held or may be moved using needle knob 156, such as by pushing on needle knob 156 to insert needle 152 into a nasal tissue or pulling on knob 156 to remove needle 152 from nasal tissue and away from an implant. System 150 may include implant 104. Implant 104 may be pre-loaded into needle 152 prior to use by a physician or other user or may be loaded by a physician or other user into needle 152 at the time of treatment (e.g., at the time of a minimally invasive or non-invasive procedure). System 150 may also include a stylet 158 configured to fit inside needle 152. Stylet 158 may hold implant 104 inside hollow needle 152 or may hold implant 104 in a first position relative to the nasal tissue, such as when needle 152 is retracted away from implant 104. Stylet 158 may push implant 104 inside needle 152 to adjust a position of implant 104. For example, stylet 158 may push implant 104 to initially place or to re-position it in needle 152, such as prior to needle 152 and implant 104 being placed into nasal tissue. Stylet 158 may push implant 104 into an implant insertion position such that distal end 168 of implant 104 is near piercing end 162 of needle 104. In particular, distal end 168 may be at the proximal side of the bevel on the piercing end. Needle 156 is moved through nasal tissue to an implant location. The depth of insertion of the needle into tissue may be indicated by marks 164 visible to the physician or other user. Such marks may, for example, be in increments of 1 mm for up to 30 mm. Because the depth of the needle in the tissue is indicated by the marks and the needle will be retracted away from the implant, the marks may precisely indicate the depth to which the implant will be placed. The physician or other user may receive tactile feedback from body tissue to determine when the needle is in place. For example, the physician or other user may "feel" the needle hitting a hard object (e.g., a bone) or "feel" a change in the way the needle behaves. Alternatively, if the needle comprises a radiopaque material, the physician may "see" the position of a needle using imaging equipment.

After moving needle 156 through nasal tissue to the implant location, but before the implant is released from the needle, stylet 158 may push implant 104 into an implant implantation position such that distal end 168 of implant 104 may be at the distal-most side of the bevel on the piercing end. The movement of the distal end of the implant from the proximal side of the bevel to the distal side of the bevel may be movement between 0 mm and 10 mm, between 1 mm and 7 mm, or between 2 mm and 4 mm. Hollow delivery needle 152 holding an implant 104 may be placed into nasal tissue.

Figure 3B:
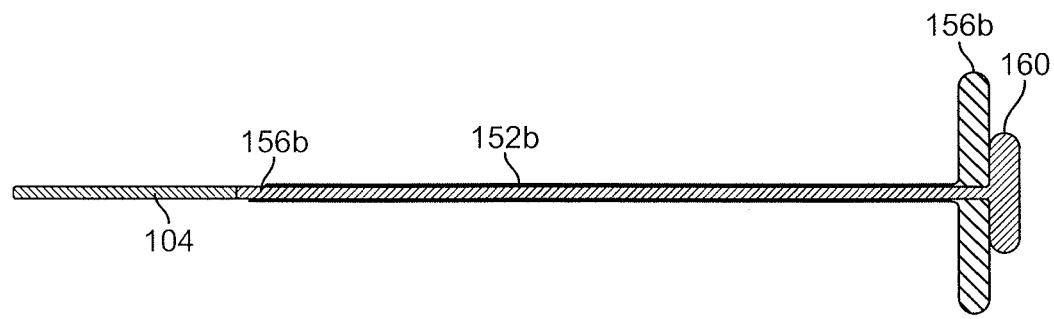

FIGS. 3A-3B show the same nasal implant system as in FIGS. 2A-2B as it appears after the implant was placed in nasal tissue. Structures changed in position in FIGS. 3A-3B relative to FIGS. 2A-2B are indicated by the addition of a lowercase letter ("a", "b", etc.) after the corresponding reference numeral (such as 152a). In particular, after implant 104 was in the desired nasal tissue location (but was still inside hollow needle 152) with stylet 158 abutting proximal end 166 (e.g., the end nearest the physician or other user) of implant 104, needle 152b was retracted by moving (e.g., pulling) needle knob 156b away from implant 104 to leave implant 104 in the tissue in the same location as it was in while inside the needle. In the next step, stylet knob 160 and needle knob 156b can be pulled (either together, or separately), removing the stylet and the needle from the tissue, leaving the implant in place in the tissue to improve (or maintain) nasal function and/or improve (or maintain) nasal appearance.

In another embodiment, needle 152 may be held still relative to implant 104. In this case, implant 104 may be pushed out of the needle by the pushing action of stylet 158 against the proximal end 166 of implant 104. In yet another embodiment, implant 104 may be placed in the nasal tissue (e.g. removed from the needle) using both actions: retracting the needle away from the implant as well as pushing the implant away from the needle with the stylet.

Figure 4A:
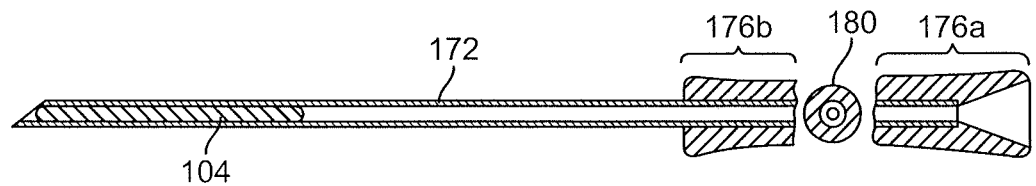
FIGS. 4A and 4B show different views of another embodiment of an implant delivery device for implanting a nasal implant into nasal tissue.
Figure 4B:
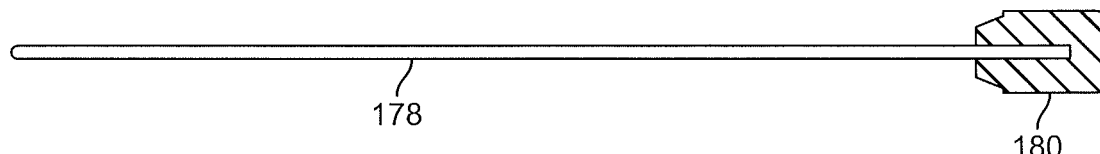

FIGS. 4A-4B show another embodiment of a nasal implant system for placing an implant into a nasal tissue similar to the nasal implant system shown in FIGS. 2A-2B and FIGS. 3A-3B with different control features. Needle knob 176a-176b comprises an elongated knob and may be grasped or held by a hand of a user or a finger and a thumb to move needle 172, as described above, into and out of nasal tissue. See also cross-sectional view 186. Stylet or pusher 178 may be grasped or held by a hand of a user (e.g. a different hand) or a finger and thumb of a user when the stylet is in place inside needle 172 to hold implant 104 in place while retracting needle 172 to place implant 104 into nasal tissue.

Figure 5A:
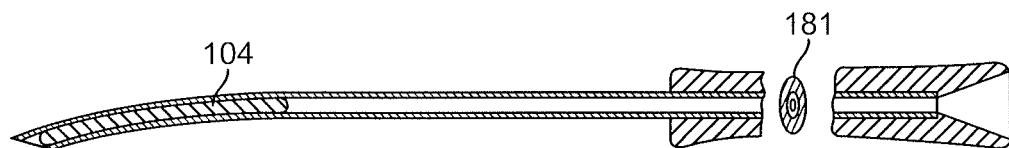
FIGS. 5A and 5B show different views of another embodiment of an implant delivery device for implanting a nasal implant into nasal tissue.
Figure 5B:

FIGS. 5A-5B show another embodiment of a nasal implant system implant for placing an implant into a nasal tissue similar to the nasal implant systems shown in FIGS. 2A-2B and FIGS. 3A-3B and FIGS. 4A-4B but with a contoured needle and with different control features. Such a contoured needle may be useful for placing a shaped (e.g. a contoured) implant into a nasal tissue (e.g. for placing an implant into an area that is hard to reach with a straight needle or for contouring the implant into the tissue to better support the tissue). A contoured implant may better conform to a tissue shape to provide support. A pre-formed contoured implant may be more effective at re-shaping a portion of a nasal tissue from a first shape to a second shape, such as by providing more force to the tissue. A contoured implant may provide better support (e.g. compared with an implant with a circular cross-section). FIG. 5A also shows the elliptical cross-sections 181 of the implant and needle.

FIGS. 6A-6E show another embodiment of a nasal implant system similar to the nasal implant systems described above. An implant and an inside of a needle may comprise (matching) elliptical cross-sectional shapes. However, the implants shown in FIGS. 6C-6E are pre-formed to have a curvature. Some implants may comprise a resilient material. Some implants may be temporarily deformed for a short time in a needle (e.g. a curved implant may be placed in a straight needle) in order for the needle to place the implant into a nasal tissue. Some embodiments provide a method of placing an implant in a tissue, including the steps of applying a force to an implant having a pre-delivery shape (or first shape) in a needle to hold it in a delivery shape (or second shape); placing the needle and the implant having the delivery shape into a nasal tissue; and removing the needle from the implant to thereby remove the force and allow the implant to return to its pre-delivery shape (first shape). The implant may include a soft barb to provide protection from movement, as described in more detail below. The needle cross section or shape provides for orientation of the implant.

Another aspect of the invention includes a system for placing an implant into a nasal tissue of a patient. Such a system may include an assembly, including a grippable housing and a delivery conduit control mechanism, and a needle (or other implant delivery conduit such as a hollow implant delivery conduit) with a piercing end configured to pierce a body tissue, the conduit configured to hold an implant and to place the implant in a body tissue wherein a movement of the delivery conduit is controllable by the delivery conduit control mechanism. Such a system may allow the implant to be unsheathed from the needle once in position in the tissue. Such unsheathing may allow an implant to be placed with greater precision and control into a specific nasal tissue region.

Figure 7A:
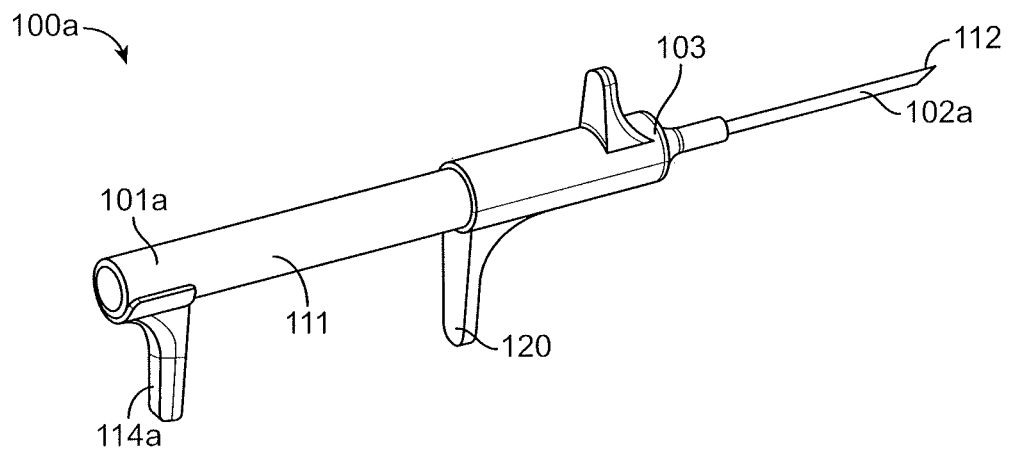
FIGS. 7A-7C show how an implant delivery device is loaded with an implant, advanced to deliver an implant to a nasal tissue, and retracted from the tissue according to some embodiments.
Figure 7B:
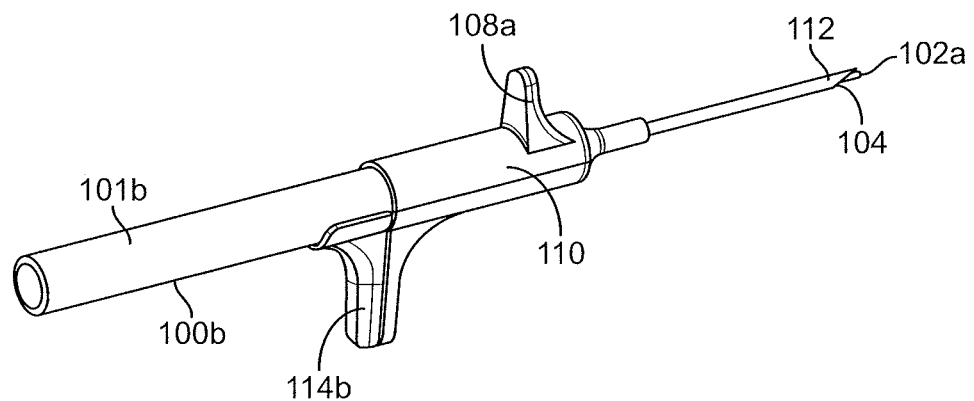
Figure 7C:
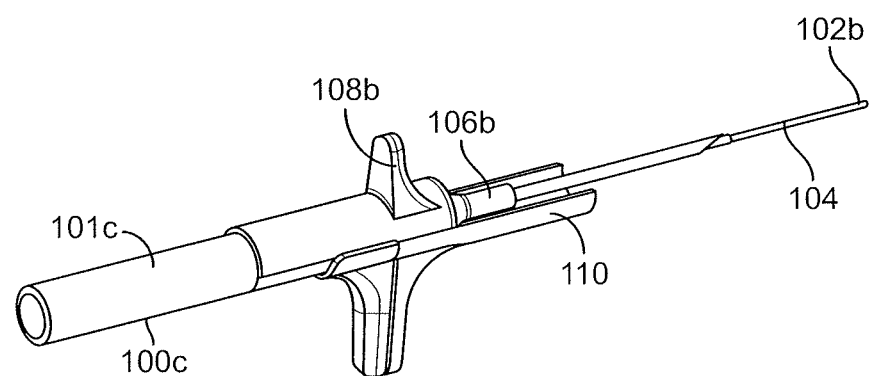

FIG. 7A shows a configuration of a nasal implant system 100 with an assembly 101 and a hollow delivery needle 102 (or other hollow delivery conduit) for implanting an implant 104 into a nasal tissue. FIG. 7A shows the implant being loaded into the needle. FIGS. 7B and 7C show other configurations of the same system during use for placing an implant in a nasal tissue. FIG. 7B shows an implant loaded in a needle and the needle advanced, just before needle retraction to place the implant in position. FIG. 7C shows the needle retracted away from the implant and the implant in position in the nasal tissue. A structure in a different position between related figures (e.g. between FIGS. 7A, 7B, and 7C) is indicated by the addition of a letter ("a", "b", etc.) after the corresponding reference numeral (such as 101a, 101b). FIG. 7A shows loading an implant into the nasal implant assembly and moving the implant distally near the distal end of the needle. FIG. 7B shows inserting the needle into nasal tissue and advancing the implant distally to the distal end of the needle. FIG. 7C shows retracting the needle and placing (releasing) the implant into the tissue.

FIG. 7A shows a hollow delivery needle with a proximal end (nearest the physician or other user) and a distal end (nearest the patient), the distal end having a piercing end 112 such that it can pierce and travel through nasal tissue to a desired implant location when a force is applied to the needle. Needle 102a is hollow and attached via a luer fitting 130 to a luer mating part (not visible in this view) of body 111 of the assembly. Prior to being attached to the body 111, a nasal implant was loaded into the proximal end of the needle. A system for placing an implant in a nasal tissue may further have a stylet (or other implant pusher member) for positioning the implant. To move implant 104 into an implant position in the needle (e.g., to the distal end of the needle) the physician (or other user) moves the stylet control lever 114a from a proximal to a distal position, which moves the stylet against the proximal end of the implant and pushes the implant near the distal end of the needle. Compare the position of stylet control lever 114a in FIG. 7A with the forward (distal) position of stylet control lever 114b in FIG. 7B. The implant is placed at the base of the bevel (the shorter side of the bevel portion) of the piercing end 112 (distal end) of the needle. In other embodiments, the implant may be placed partway along the bevel. Generally, the end of the implant may be at the base of the bevel, or less than 1 mm, less than 2 mm, less than 3 mm, or less than 6 mm from the base of the bevel. The implant is now in a travel position in needle 102a and implant 104 to travel through nasal tissue to an implant position. Needle 102 also has a piercing end 112 on its distal end. Body 111 is held by a hand of a physician or other user to guide needle 102a, which holds implant 104, via the piercing end 112, through body tissue to the desired implant location in nasal tissue. In some embodiments, having an implant near the end of the needle to at least partially block the needle opening reduces or prevents tissue coring (in which tissue is cored or collected inside the needle). Preventing or minimizing coring reduces patient pain and recovery time. Placing the implant at the base of the bevel without substantially protruding from the needle opening permits the beveled distal tip to perform its cutting function as the needle is advanced into tissue.

After moving needle 102a through nasal tissue to the implant location, but before the implant is released from the needle, the physician (or other user) moves the stylet control lever 114a from a proximal to a distal position, which pushes implant 104 slightly further to the distal end of the needle (e.g. to the distal side of the bevel on the piercing end). This movement may be between 0 mm and 10 mm, between 1 mm and 7 mm, or between 2 mm and 4 mm. This additional movement places the implant close to or beyond the point to which the distal end of the needle as inserted into nasal tissue.

The system may also include a needle control mechanism 108a (e.g., a delivery conduit control mechanism) for controlling movement of needle 102a. Needle control mechanism 106a retracts from a first position, shown in FIG. 7B, to a second position, needle control mechanism 106b, shown in FIG. 7C, so that it retracts needle 102a from a first position shown in FIG. 7B, proximally away from implant 104, and into a second position in grippable housing 110, shown by needle 102b in FIG. 7C. When the needle retracts, it leaves implant 104 in place in the nasal tissue in the desired location. The needle control mechanism may include a lever 108a configured for use by a physician or other user to control needle movement. Lever 108a may be moved from a first position (shown in FIG. 7B) to a second position (see lever 108b in FIG. 7C). A stylet (not visible in this view) may extend distally between the grippable housing 110 and may be at least partially disposed inside the hollow needle 102a or 102b. The stylet may connect with the proximal end of the implant and may control implant movement relative to the needle. In particular, the stylet may prevent the implant from moving proximally while the needle is being retracted. Instead, the stylet may keep the implant in the desired location as the implant is unsheathed from the needle (e.g., the needle is retracted away from the implant). In some embodiments, such unsheathing means that the needle, specifically the piercing tip of the needle, which is designed to enter tissue and minimize tissue damage, is responsible for all tissue penetration. An implant does not need to be pushed or forced into position against nasal tissue. Tissue damage, patient pain, and healing times may all be reduced.

Additionally, the control mechanism and the needle may move relative to the housing; that is, the housing remains in its position while the needle control mechanism and needle retract towards it or through it or partially through it. In particular, the assembly is configured so that the housing and the stylet—and the implant—can be held steady by the physician or other user while the needle moves so that the implant is placed in the desired location in the nasal tissue.

In some embodiments, the assembly may allow the physician or other user to readjust the needle after it is in place in the tissue.

In some embodiments, an implant may be loaded in the distal end of the needle. In some embodiments, a needle may be pre-loaded with an implant, such as on its own or as part of a kit, before use by a physician or other user. In some embodiments, an implant may be loaded into a needle by a physician or other user before performing a nasal implant procedure, such as a non-invasive or minimally invasive procedure. In some embodiments, an implant may be loaded into a stylet channel through a side port (e.g. in the assembly body).

In some embodiments a needle may (e.g., larger than 10 gauge, 10, 11, 12, 13, 14, 15, 16, 17, 18, 19, 20, 21, 22, 23, 24, 25, 26, 27, 28, 29, 30, 31, or 32 gauge, or smaller than 32 gauge). An implant may be sized to fit (e.g., fit tightly inside the needle). In some embodiments using a smaller needle may product less tissue damage. In some embodiments, a smaller needle may (better) fit into small areas of the nasal tissue (e.g., between the skin/mucosa and cartilage of the nose).

Figure 8A:
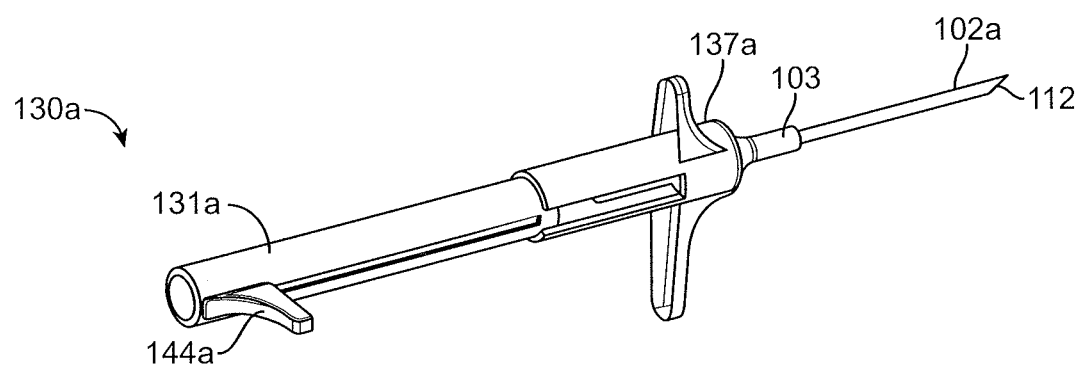
FIGS. 8A-8C show how another implant delivery device is loaded with an implant, advanced to deliver an implant to a nasal tissue, and retracted from the tissue according to some embodiments.
Figure 8B:
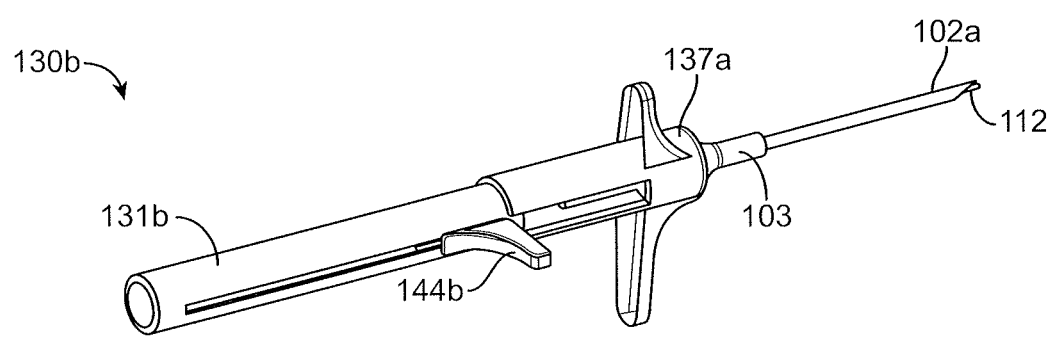
Figure 8C:
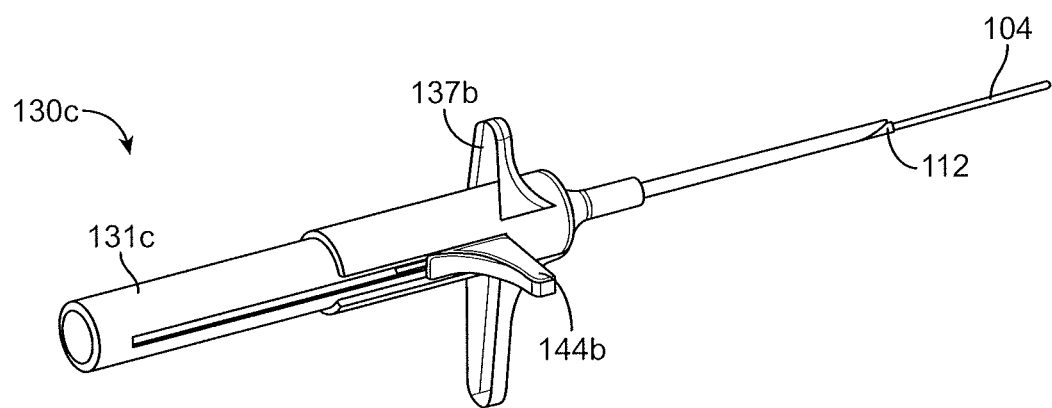

FIGS. 8A-8C show another embodiment of a system for placing an implant into a nasal tissue of a patient, related to the embodiment of FIGS. 7A-7C. FIG. 8A shows a configuration of a nasal implant system 130 with an assembly 131 and a hollow delivery needle 102 (or other hollow delivery conduit) for implanting an implant 104 into a nasal tissue. FIG. 8A shows the implant being loaded into the needle. FIGS. 8B and 8C show other configurations of the same system during use for placing an implant in a nasal tissue. FIG. 8B shows an implant loaded in a needle and the needle advanced, just before needle retraction to place the implant in position. FIG. 8C shows the needle retracted away from the implant and the implant in position in the nasal tissue. FIG. 8A shows loading an implant into the nasal implant assembly and moving the distal end of the implant near the distal end of the needle. FIG. 8B shows inserting the needle into nasal tissue and advancing the implant distally to the distal end of the needle. FIG. 8C shows retracting the needle and placing (releasing) the implant into the tissue. The detailed description of the implant loading, implant advancement to the distal end of the needle, placement of the needle and implant into nasal tissue, and retraction of the needle to place the implant into the nasal tissue and in contact with the nasal tissue is as described above for FIGS. 7A-7C. Changes relative to FIGS. 7A-7C include the shape and orientation of stylet control lever 144a, 144b and the shape and orientation of needle control mechanism 137a, b.

Figure 9A:
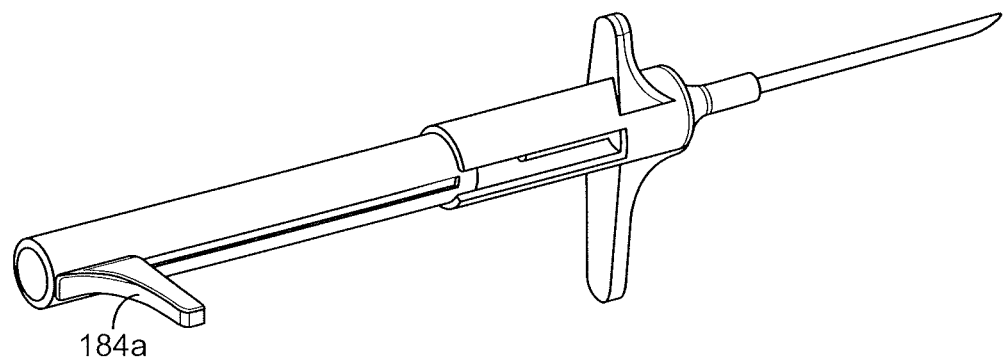
FIGS. 9A-9C show how yet another implant delivery device is loaded with an implant, advanced to deliver an implant to a nasal tissue, and retracted from the tissue according to some embodiments.
Figure 9B:
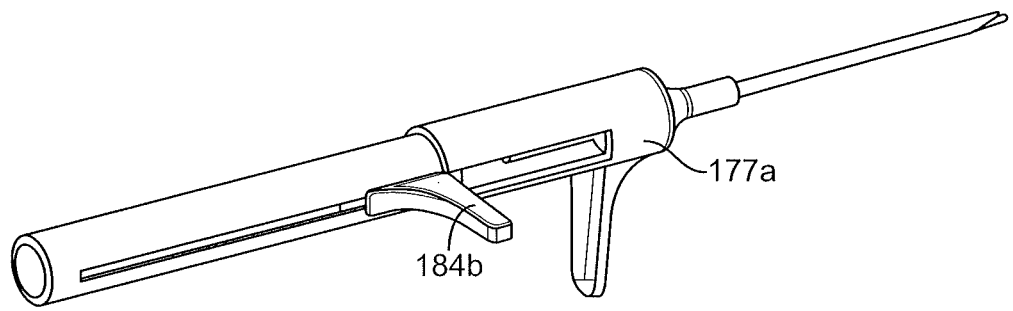
Figure 9C:
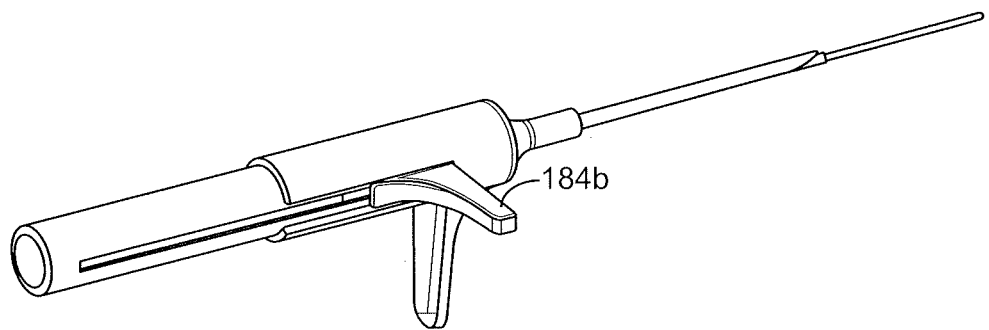

FIGS. 9A-9C a system for placing an implant into a nasal tissue of a patient. FIGS. 9A-9C show another embodiment of a system for placing an implant into a nasal tissue of a patient, related to the embodiment of FIGS. 7A-7C and FIGS. 8A-8C. FIG. 9A shows a configuration of a nasal implant system 130 with an assembly 131 and a hollow delivery needle 102 (or other hollow delivery conduit) for implanting an implant 104 into a nasal tissue. FIG. 9A shows the implant being loaded into the needle. FIGS. 9B and 9C show other configurations of the same system during use for placing an implant in a nasal tissue. FIG. 9B shows an implant loaded in a needle and the needle advanced, just before needle retraction to place the implant in position. FIG. 9C shows the needle retracted away from the implant and the implant in position in the nasal tissue. FIG. 9A shows loading an implant into the nasal implant assembly and moving the distal end of the implant near the distal end of the needle. FIG. 9B shows the configuration of the system while inserting the needle into nasal tissue and advancing the implant distally to the distal end of the needle. FIG. 8C shows the configuration of the system while retracting the needle and placing (releasing) the implant into the tissue. The detailed description of the implant loading, implant advancement to the distal end of the needle, placement of the needle and implant into nasal tissue, and retraction of the needle to place the implant into the nasal tissue and in contact with the nasal tissue is as described above for FIGS. 7A-7C. Changes relative to FIGS. 7A-7C include the shape and orientation of stylet control lever 184a, 184b and the shape and orientation of needle control mechanism 177a, b.

As indicated above, at different times, implant 104 may be moved inside assembly 101 or moved inside needle 102 or may be held in place inside assembly 101 or inside needle 102. An end of implant 104 may be held by the stylet. Needle 102 may be further internally configured to hold implant 104 such as by tight fit with an implant. The tight fit may be "just right"—a friction fit sufficiently tight to hold the implant inside the needle, but loose enough to allow the force from a stylet or other pusher to hold the implant in place during needle retraction to place the implant into nasal tissue. In such embodiments, a delivery needle can be retracted away from an implant in order to place the implant into the nasal tissue without the need for a mechanism to hold the implant or a mechanism or cutting tool to release the implant from the needle. A "just right" friction fit may also be helpful for holding the implant in the needle, such as in a kit.

FIGS. 10A-10J show various embodiments of implants. Any of these implants may be used with any of the systems, assemblies, and devices and with any of the methods described herein or an implant may be used with other system, assembly, or device described elsewhere.

Such implants may be useful for placing in a body tissue, such as nasal tissue. One aspect of the invention provides a generally longitudinal resilient implant comprising: a first end, a second end and a length therebetween, the implant comprising a surface feature along the length. In some embodiments, an implant is configured to provide an implant flexural rigidity between 2.5e-6, and 1.5e-5. In some embodiments, an implant is configured to provide an implant flexural rigidity between 2.5e-6, and 1.5e-5 after being in contact with a body tissue for at least 3 months, for at least 6 months, for at least 9 months, or for at least one year. Some embodiments of an implant include one or a plurality of surface features (such as, e.g., a fin, a notch, a rib, or a scallop. Some embodiments of an implant comprise a resorbable feature (such as, e.g. PLLA-PDLA in a ratio from 90:10 to 50:50. Some embodiments include an implant with a bend, with an angle greater than 0 degrees and less than 45 degrees, less than 35 degrees, less than 25 degrees, or less than 15 degrees. Some embodiments include an implant less than 30 mm, less than 25 mm, less than 20 mm, or less than 15 mm. Some embodiments include an implant with a diameter (e.g. an outer diameter) configured to form a tight fit within a 16 gauge needle. Some embodiments have an outer diameter less than 1.5 mm, less than 1.2 mm, less than 1.0 mm or between 0.8 and 1.2 mm. In some embodiments, an implant comprises a color that is not readily visible through skin (e.g. skin-tone, tan, brown, etc.). In some embodiments, an implant comprises a radiopaque material. An implant may preserve its shape; may be strong, yet flexible; it may be similar to cartilage in such properties.

Another aspect of the invention includes a generally longitudinal implant having a first end, a second end, and a length there between, the first end comprising an end feature. In some embodiments, the second end comprises an end feature. In some embodiments, the first end feature and the second end features may comprise the same configuration. In some embodiments the first end feature and the second end features may comprise different configurations. In some embodiments, an end feature is configured to mate with a pusher tool. In some embodiments, an end feature comprises an ellipse. In some embodiments, an end feature comprises an expansion feature, such as tines or fins. An expansion feature may be useful, when inserted into a nasal tissue, for preventing the implant from moving, such as, for example, from moving into the path or space left after a removal of a needle that placed the implant in the tissue. An expansion feature may be useful for anchoring the implant to a bone or to cartilage. In some embodiments, an implant with an elliptical distal end may allow seating of the implant against a bone at any angle.

An end feature may be useful for fixing an implant together with a tissue. One or more than one surface features may be useful for fixing an implant together with a tissue.

Another aspect of the invention provides an adjustable implant (e.g. adjustable for an individual patient). In some embodiment, a shape of an implant is conformed in situ to a shape of a nasal tissue. In some embodiments, a particular length of an implant can be chosen based on an individual's nasal structure size(s).

FIG. 10A shows an implant comprising scallops such as a series of circular segments or angular projections. Such scallops, segments or projections may provide additional surface area (e.g. for tissue interaction) to reduce or prevent implant movement (such as backing out of the implant into an incision or needle insertion site). Such scallops, segments or projections may be used to provide an indication of length and to provide stability during implant cutting.

FIG. 10B shows an implant comprising an elliptical first end and an elliptical second end. An elliptical end may provide greater surface area to rest against a tissue at any angle.

FIG. 10C shows an implant comprising an elliptical first end (semi-elliptical). An elliptical end may provide greater surface area to rest against a tissue at any angle.

FIG. 10D shows an implant comprising a plurality of ribs and a conical first end and a conical second end. An implant may include one rib or more than one rib. Such ribs may include alternating raised regions and depressed regions (valleys) with smooth transitions between the a rib and a depression (valley). A conical end may provide greater surface area to rest against tissue at any angle when an implant is in place in a tissue. A rib(s) along the shaft may provide additional surface area for the tissues to adhere. A valley of ribs may provide stability when cutting an implant.

FIG. 10E shows an implant comprising a plurality of fins and a conical end (as described above). One or more than one fin may provide additional surface area for tissue to adhere to the implant. A valley of fins may provide stability during implant cutting.

FIG. 10F shows an implant with a first semi-elliptical end and a second end with a concave end feature. A concave end feature may allow tissue to embed within the implant. A concave end feature may mate with a corresponding (e.g. elliptical) shape on an insertion tool (e.g. a stylet, a pusher).

FIG. 10G shows an implant with a first semi elliptical end and a plurality of notches (e.g. along one side or one region of the implant). One or more than one notch may provide leverage to reduce or prevent implant movement (such as backing out of the implant into or through an incision or needle insertion site). One or more than one notch may provide stability during cutting and indication of implant length (e.g. for implant cutting).

FIG. 10H shows an implant with a first semi-elliptical end and a second end with an expansion feature(s). A concave expansion feature may allow tissue to embed within the implant. A concave end feature may mate with a corresponding (e.g. elliptical) shape on an insertion tool (e.g. a stylet, a pusher). The flared geometry may be compressed within an insertion tool (e.g. needle) and expanded or allowed to expand after being placed in tissue. Such an expansion feature may provide leverage to reduce or prevent implant movement (such as backing out of the implant into or through an incision or needle insertion site).

Figure 10I:
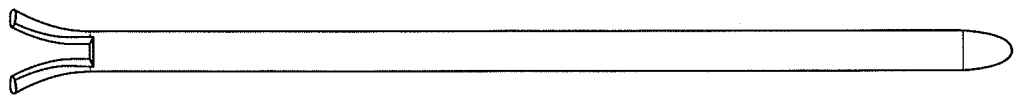

FIG. 10I shows an implant with a first semi-elliptically shaped end and a second end with a plurality of tines. One or more than tine on an implant end may be compressed within the insertion tool (needle). Upon deployment into the tissue, the tine or tines may expand and provide leverage for the implant. Such an expansion feature may provide leverage to reduce or prevent implant movement (such as backing out of the implant into or through an incision or needle insertion site).

Figure 10J:
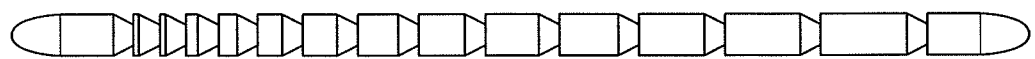
Figure 10K:
FIGS. 10K-10N show cross-sectional views of various embodiments of nasal implants.
Figure 10L:
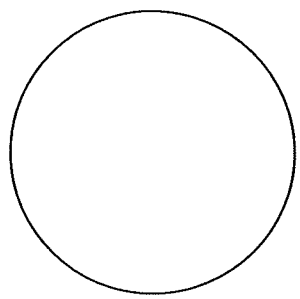
Figure 10M:
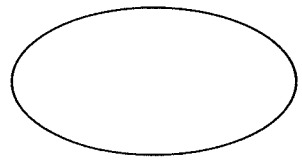
Figure 10N:
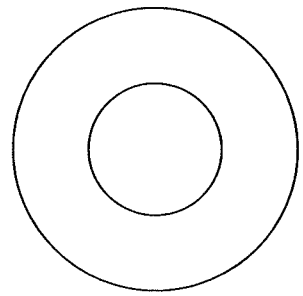

FIG. 10J shows an implant with a first conical end and a second conical end and a plurality of modified fins along the shaft. The modified fins show a (continuous) progression from a shorter length to a longer length from a first region (which may a first end region) to a second region (which may be a second end region). Such modified fins may provide additional surface area for the tissue to adhere. A valley of fins may provide stability when cutting an implant and may provide an indication of implant length (e.g., for implant cutting).

A ribbed implant or an implant with a regular, repeating pattern comprising a biodegradable material may provide a controlled degradation pathway.

FIGS. 10K-10N show cross-sectional views of various embodiments of an implant.

FIG. 11 and FIGS. 12A-12C shows other systems for placing an implant into a nasal tissue of a patient. Such systems may include an assembly comprising a grippable housing and a delivery conduit control mechanism, and a needle (or other hollow implant delivery conduit) configured to hold an implant and to place the implant in the nasal tissue, the needle further having a piercing end to pierce body tissue for moving the needle through the body tissue.

Figure 11:
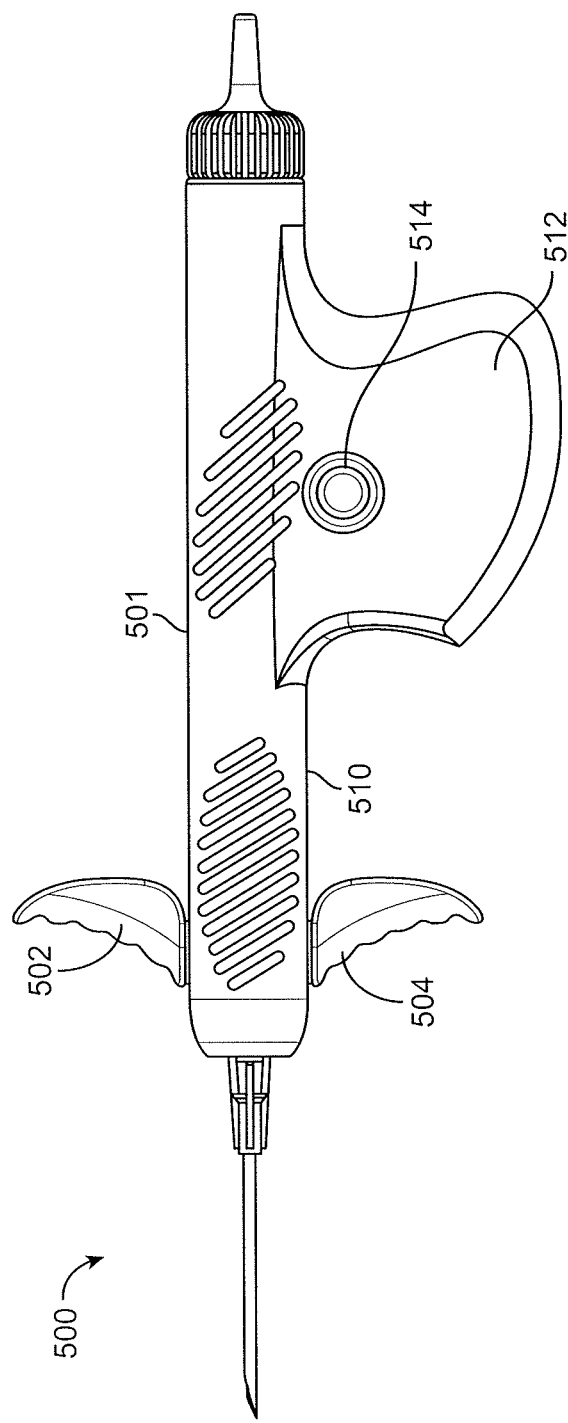
FIG. 11 shows an embodiment of an implant delivery device for implanting a nasal implant into nasal tissue.
Figure 12A:
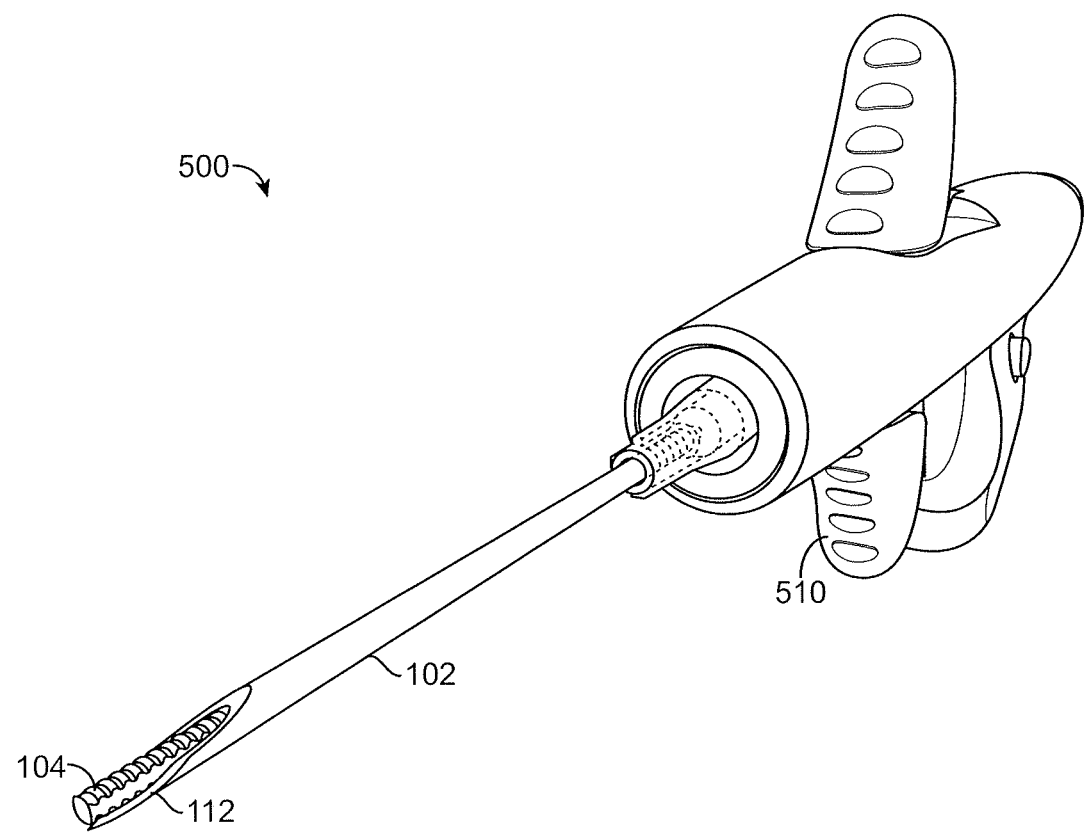
FIGS. 12A and 12B show different views of yet another embodiment of an implant delivery device for implanting a nasal implant into nasal tissue.
Figure 12B:
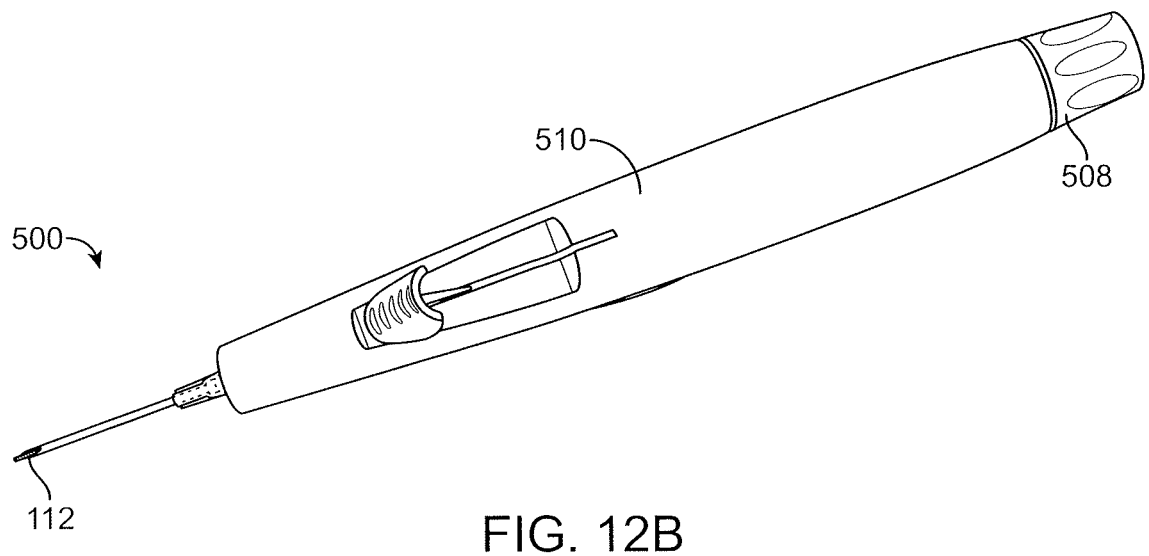
Figure 17:
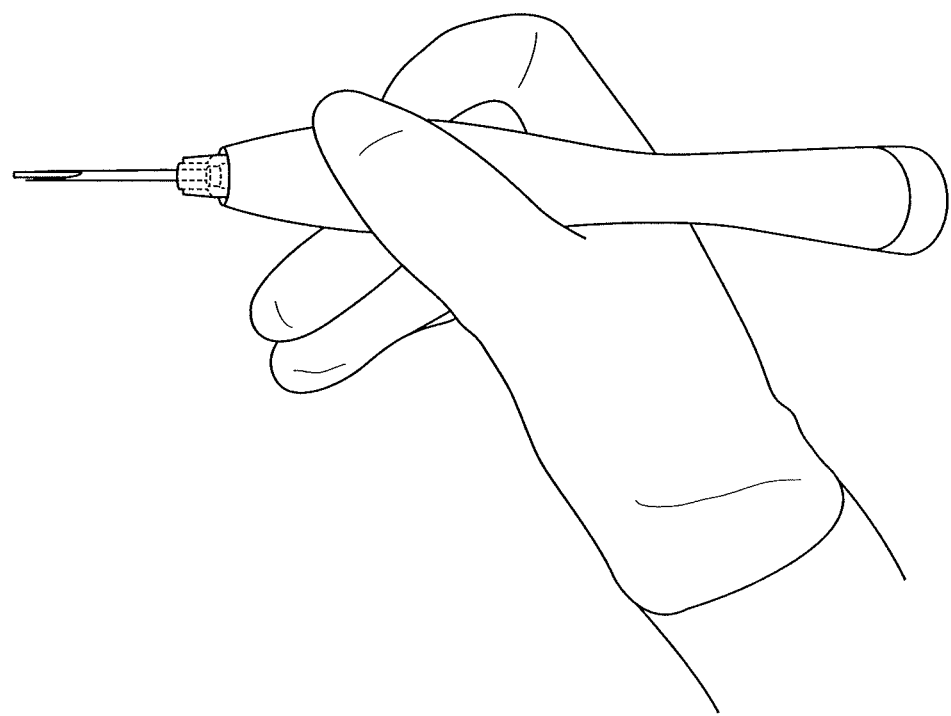
FIG. 17 shows an embodiment of implant delivery device with a contour grip.
Figure 18:
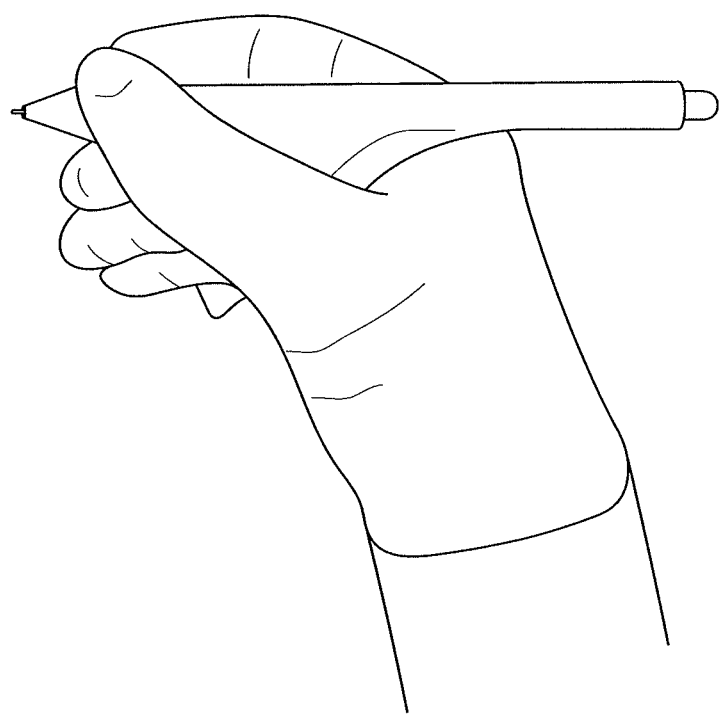
FIG. 18 shows an embodiment of an implant delivery device with another type of handle grip.
Figure 19:
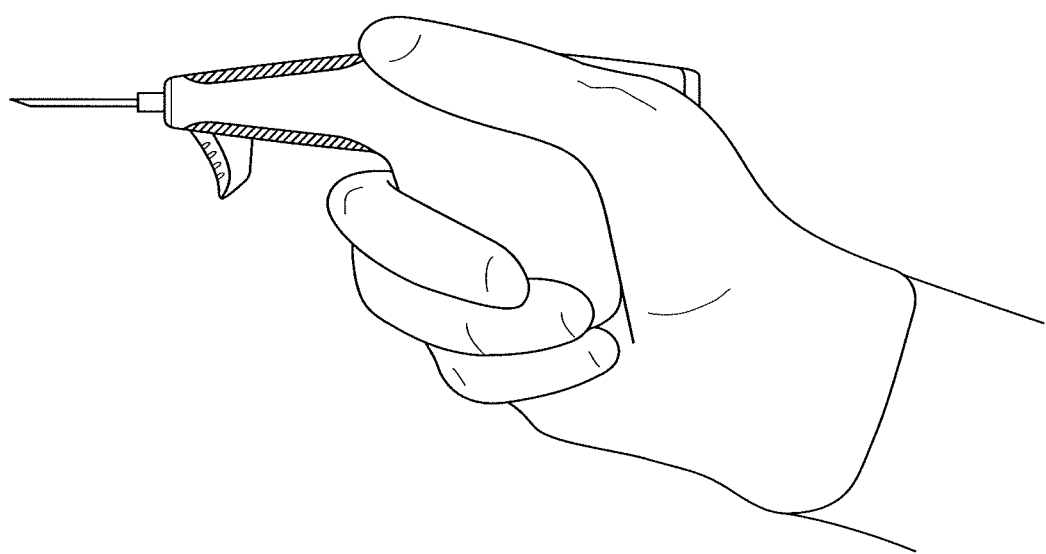
FIG. 19 shows an embodiment of an implant delivery device with another type of handle grip.
Figure 20:
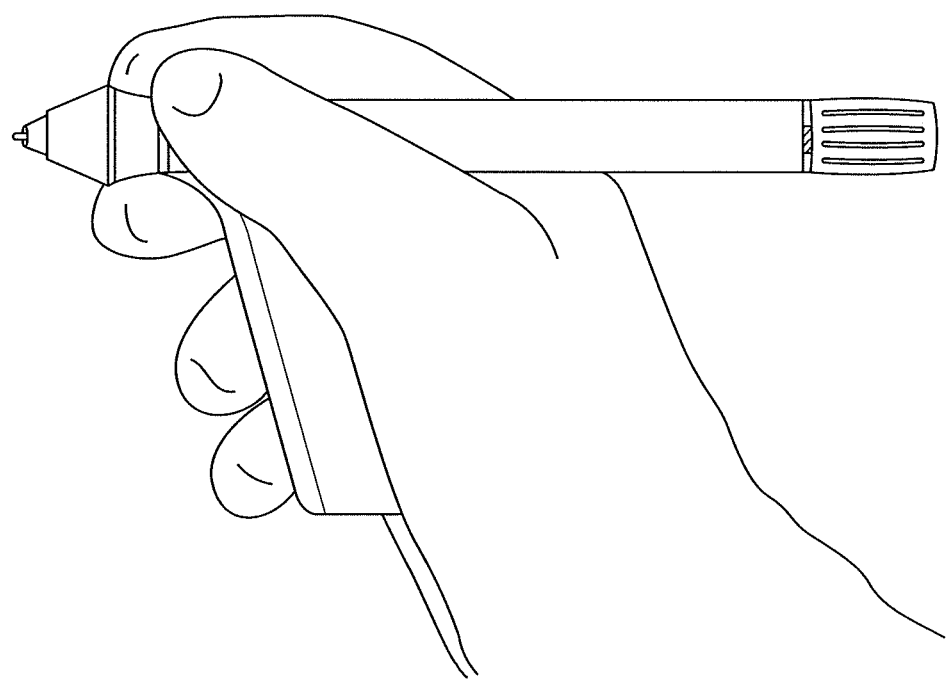
FIG. 20 shows an embodiment of an implant delivery device with another type of handle grip.
Figure 21:
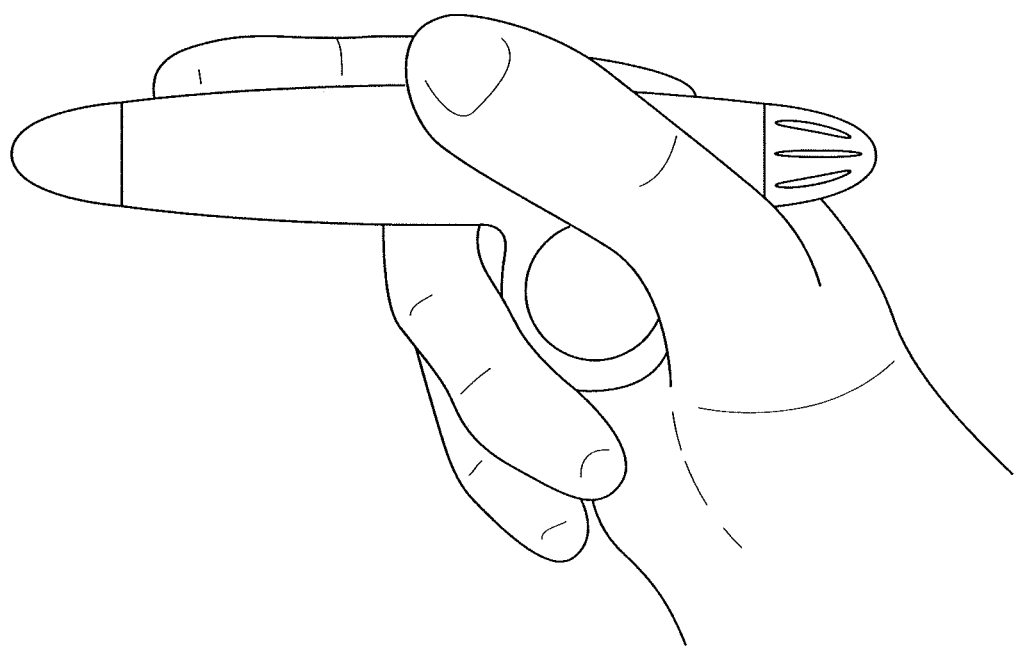
FIG. 21 shows an embodiment of an implant delivery device with another type of handle grip.

FIG. 11 shows another configuration of a nasal implant system 500 with an assembly 501 and a hollow delivery needle 102 (or other hollow delivery conduit) for implanting an implant 104 into a nasal tissue. FIGS. 12A-12C show a similar nasal implant system 520 with a style control knob variation that can be used to push an implant into a needle (e.g. into a proximal end of a needle prior to attachment of the needle to the assembly. Nasal implant system 500 or nasal implant system 520 may include an unsheathing option to thereby more precisely place an implant into a particular nasal tissue. Taken together, FIG. 11 and FIGS. 12A-12C, show the configuration of the system during steps in placing an implant into a nasal tissue. FIG. 11 shows the nasal implant system with delivery needle 102 ready to place for placing an implant into a nasal tissue (not shown). Referring to FIGS. 12A and 12B, implant 104 has a proximal end (closest to the physician or other user; not readily visible in this view) and a distal end 168. Implant 104 had previously been loaded into the proximal end of delivery needle 102 and the proximal end of delivery needle 102 connected with grippable housing 510. Implant 104 had been distally advanced by being pushed through needle 102 with a stylet (e.g. rotation of implant control knob 508 by a physician or other user) to sit close to piercing end 112 of needle 102 under control of implant control knob 508, and held close to piercing end 112 of the needle. Delivery needle 102 with implant 104 held near its piercing end 112 had then been placed in body tissue (e.g. nasal tissue) and advanced through body tissue (e.g. through nasal tissue or surrounding tissue) to place piercing end 112 of needle 102 at a distal-most end of the desired implant location. Once the piercing end 112 of needle 102 was in place, implant 104 had been further distally advanced to be placed at the very distal end of needle 102 (e.g. at the distal end of the bevel). At this point, the implant is ready to be placed into the nasal tissue and the implant can be unsheathed from the needle. A user grabs or holds the hand grip 512. The user places a first finger on (the distal portion) of first trigger member 502 and a second finger on (the distal portion) of second trigger member 504. A user presses safety button 514 to allow needle 102 movement. The user pulls on the first trigger member and second trigger member to thereby withdraw the needle into grippable housing 510 and to unsheath implant 104 in place in the tissue. Assembly 501 is then withdrawn from the nasal tissue, leaving the implant in place.

FIGS. 13A-13C show engineering views of one embodiment of a device similar to that shown in FIG. 11 and FIGS. 12A-12C. FIGS. 14 and 15 shows a side views and inner workings of an embodiment of an assembly similar to the assemblies shown in FIG. 11, FIGS. 12A-12C, and FIGS. 13A-13C. FIGS. 14-21 show various embodiments of grippable housings, hand grips, and triggers, including a single trigger, a double trigger, a "pencil grip" embodiment and a pistol grip embodiment. In some embodiments, a double trigger and pistol grip are combined. In some embodiments, the assembly/handgrip is configured to allow a single person to perform various actions (e.g. inserting the needle and implant into tissue, unlocking the needle safety, unsheathing the implant/withdrawing the needle from the tissue, and withdrawing the assembly from the nasal tissue.). In some embodiments, the assembly/grip is configured to be usable by either a right-handed or a left-handed person (e.g., without making any changes to the assembly/handgrip). In some embodiments, the assembly is configured to place the implant with no more than 10 N. In some embodiments, the assembly is configured to retract with no more than 10 N.

Another aspect of the invention provides systems, assemblies, and implants and methods for shaping an implant in a tissue in the body. Shaping an implant in vivo may allow the shape of the implant to be custom fit (sized and shaped) to the nasal anatomy to better address the condition that is being corrected by the implant. Shaping an implant in vivo (e.g. to a non-linear shape) may also reduce tissue damage by, for example, allowing a smaller needle to be used for implant insertion. Use of a custom shaped implant may provide an advantage such as providing a larger reshaping surface, providing an increased level of support to a tissue in need of support, reducing the likelihood of extrusions (e.g., the implant being pushed out of place), or reducing the likelihood of the explant being externally visible. Although a custom formed implant may provide an advantage, there are a number of obstacles to generally providing an in vivo custom formed implant. One obstacle is how to provide energy to an implant so that the implant becomes responsive to being shaped. Another obstacle is how to minimize tissue damage that might be due to a system or device used for shaping or delivering energy. Another obstacle is how to prevent nasal tissue from being damaged by an energy provided for shaping an implant. Another obstacle is how to remove any energy delivery elements or shaping devices while preventing or minimizing damage to nasal tissue. Another obstacle is how to reshape implant that is disposed inside a nasal tissue when the implant is not readily accessible to a physician or other individual. Another obstacle is what to do if an implant is initially formed into an undesired shape.

An implant may be heated by external heating/conduction heating. After implant insertion, heat is applied through conduction directly to the patient's nose with a heater tool either from inside the nostril, outside the nostril, or both simultaneously. A heater tool may be used to apply force to shape the implant. An implant may be heated by external heating/alternate heating in which heat is applied directly to the patient's nose with a heater tool either from inside the nostril, outside the nostril, or both simultaneously. The source of heat may be, for example, ultrasonic or microwave. An implant may be heated with a pre-heated cannula heater, as described below. After insertion the needle tip is heated. This heats the implant and the local tissue to reduce cooling of the implant. The needle is removed and the implant is quickly shaped (freeform shaping). An implant may be heated by internal heating/cannula heater as described below. After insertion, the needle is retracted exposing a heater at the end of a cannula. This heats the implant at the end of cannula. The heater is pulled off the implant as it is shaped. An integrated insertion tool and heater tool may be used; shaping can occur simultaneously with implantation. An implant may be heated with a flexible heater/ribbon heater as described below. A flexible heater element encapsulates the implant. Both components are inserted together into the patient. After needle retraction, the flexible heater is heated and the implant shaped. The flexible heater is then removed. The heater may be a flexible ribbon heater wrapped around the implant. Insulation material may be present to protect internal tissue. The insertion tool and heater may be integrated together. This may allow for a local implant temperature well above a glass transition temperature, which may allow for simpler bending of the implant. An implant may be heated using internal heating/flexible heater/coiled wire as described below. The flexible heating element may be located in the center of the implant. The heater can be a resistive heater or a thermal conductor. Both components may be inserted together into a patient. After needle retraction, the flexible heater may be heated and the implant shaped.

Any form of energy that allows an implant to be shaped may be used (e.g. heat, microwave, ultrasonic). Any form of energy delivery to the implant that allows or causes a change in the implant may be used. For example, energy may be delivered from outside the nose (such as, e.g., by conduction, or by ultrasonic waves or microwaves. Energy may delivered from inside the nose, such as by a heater heating an end of an implant, a heater heating a side of an implant, a heating an inside of a nose. A system for shaping an implant in a tissue in a body includes a grippable housing comprising a delivery conduit control mechanism; a hollow implant delivery conduit with a piercing end, the conduit connected with and its movement controllable by the delivery conduit control mechanism, the conduit configured to hold an implant, pierce a body tissue with the piercing end, and place the implant in the tissue; an energy delivery element configured to deliver energy to the implant when the implant and the energy delivery element are in place in the tissue; an energy source for delivering energy to the energy delivery element; and an energy source controller configured to control the energy delivered to the energy delivery element from the energy source.

Figure 22:
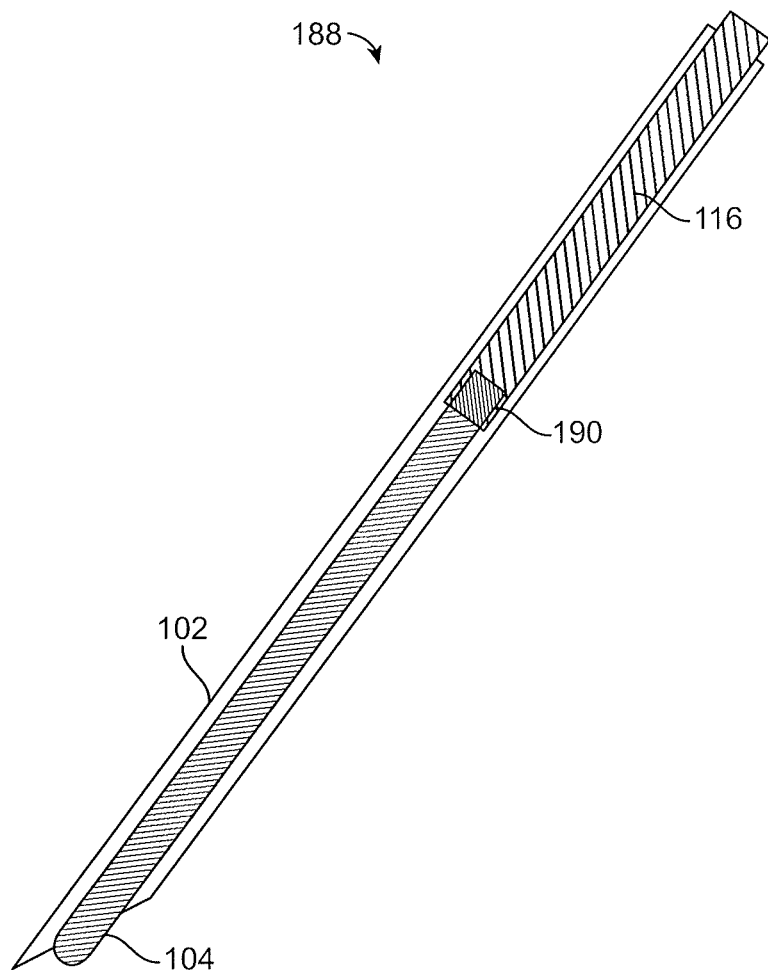
FIG. 22 shows a portion of an embodiment of an implant delivery system for shaping an implant in a tissue in a body.
Figure 23A:
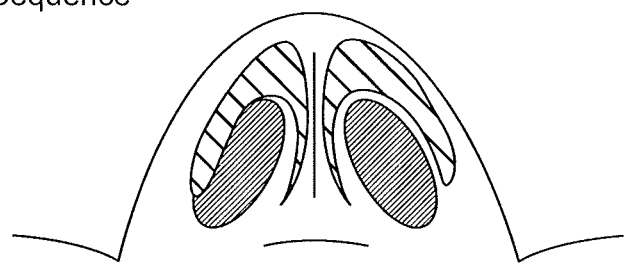
FIGS. 23A-23N show a method of shaping a nasal implant in a tissue using an implant delivery device such as the one shown in FIG. 22 according to one aspect of the disclosure.
Figure 23B:
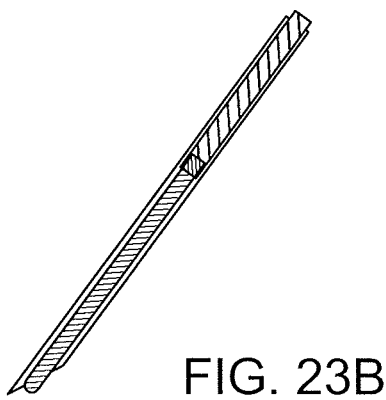
Figure 23C:
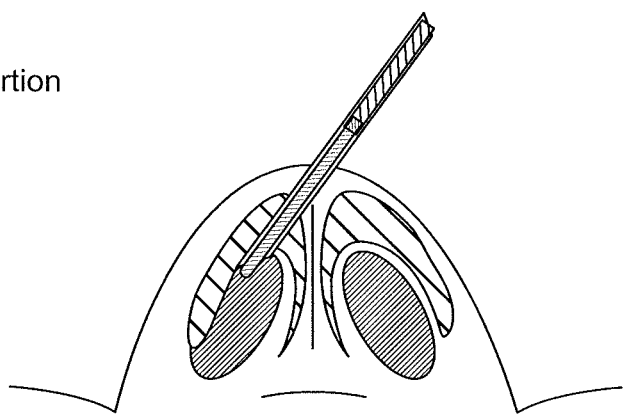
Figure 23D:
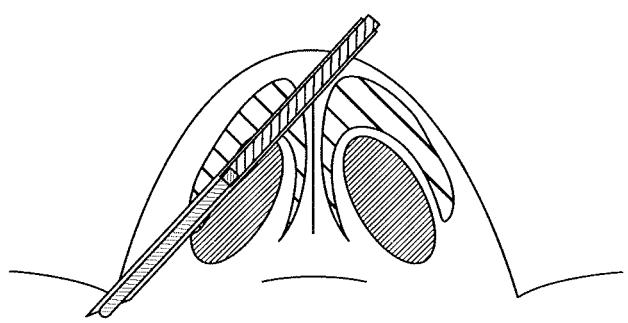
Figure 23E:
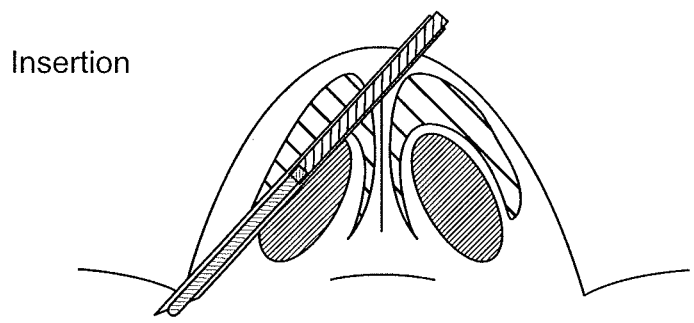
Figure 23F:
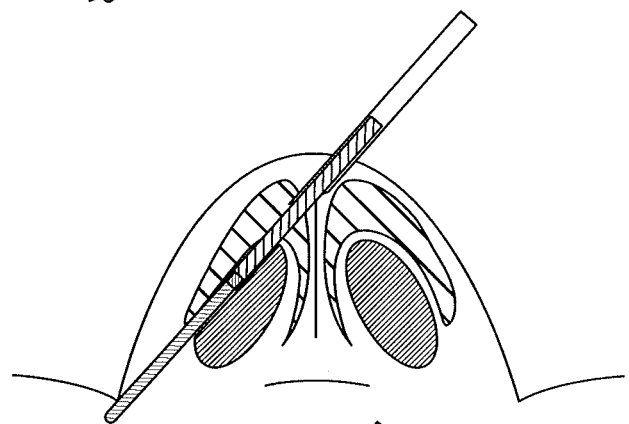
Figure 23G:
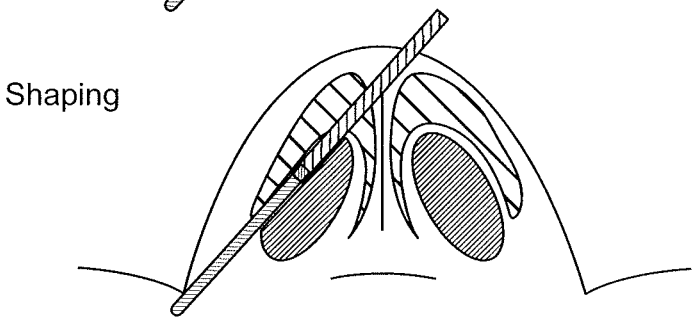
Figure 23H:
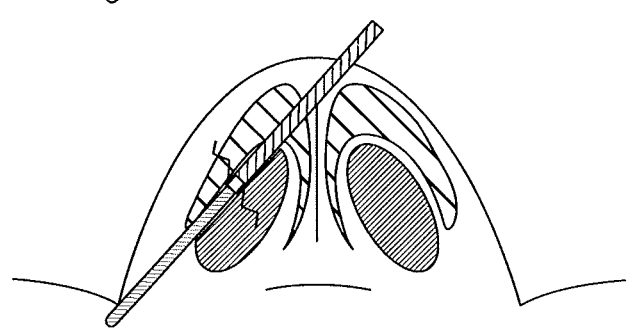
Figure 23I:
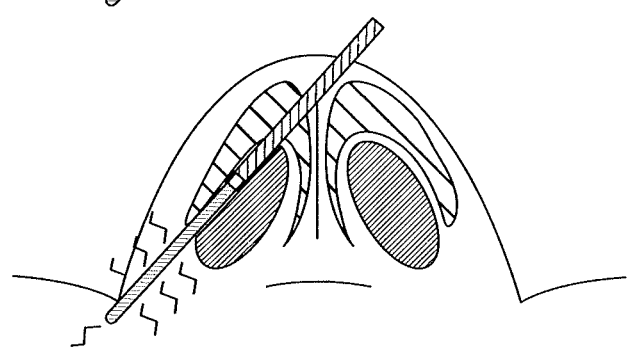
Figure 23J:
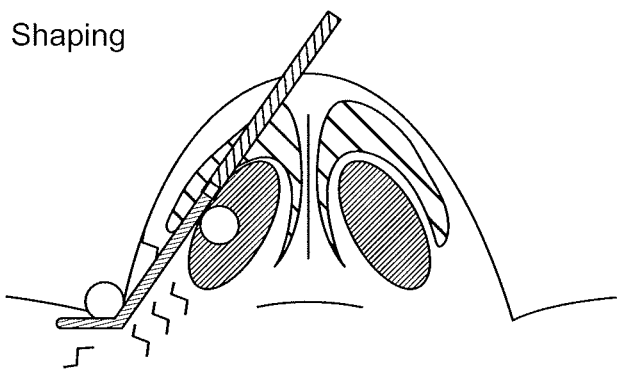
Figure 23K:
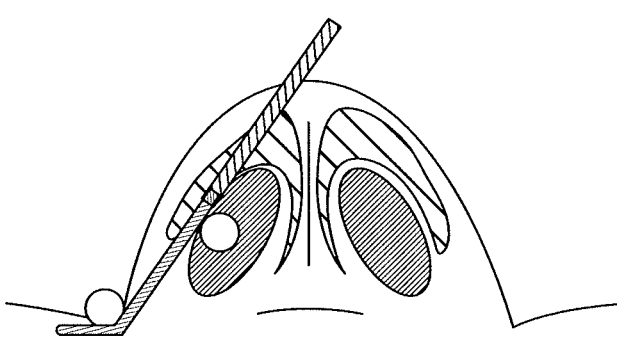
Figure 23L:
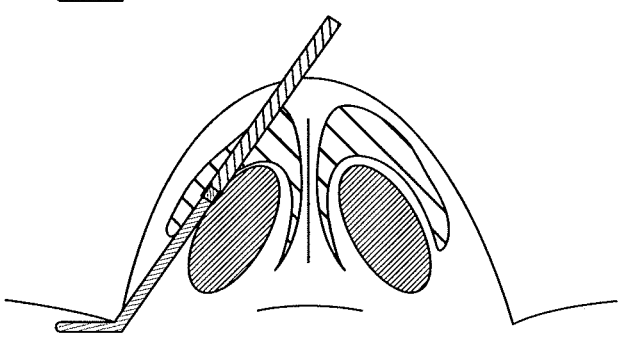
Figure 23M:
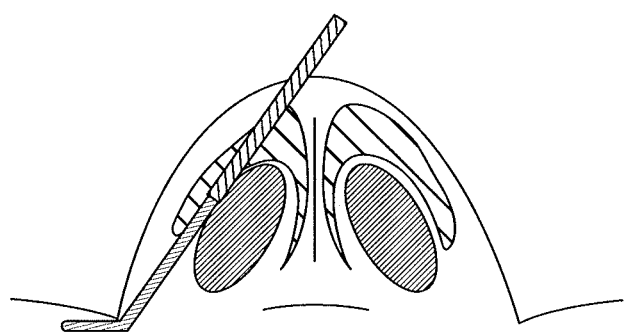
Figure 23N:
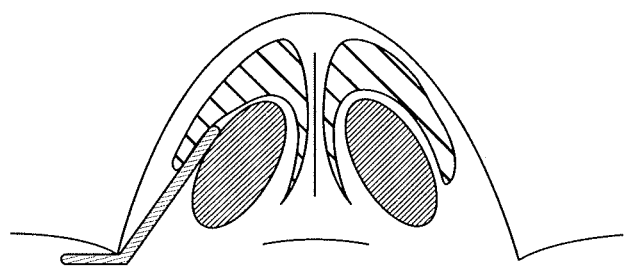

FIG. 22 shows a portion of a system 188 for shaping an implant in a tissue in a body and FIGS. 23A-23C show steps in shaping a nasal implant in a nasal tissue using such a system. The system and method use a heating element between the implant and stylet and carried into the nasal tissue using a delivery needle. Similar to other needles and implants described elsewhere in the disclosure, FIG. 22 shows implant 104 disposed in a needle 102, as they would appear in position in a tissue, ready for unsheathing of the implant by the needle to place the implant in place in the tissue. Implant 104 comprises a heat responsive material (e.g., an energy responsive material), such that implant 104 may become more flexible upon exposure to heat. FIG. 22 additionally shows a heater 190 (an energy delivery element) between the stylet and the implant and configured to provide heat to the implant. FIGS. 23A-23N show steps in inserting a heat responsive implant into a tissue, and changing a shape of the implant. FIGS. 23A-23B show preparation steps. FIG. 23A shows a physician examining the nose to find the optimal position for the implant, and applying anesthesia to the patient near the insertion site. The physician waits for the anesthesia to take effect and cleans the surface of the insertion site with an antiseptic solution. FIG. 23B shows the implantation tool is made ready, removing it from sterile packaging. FIGS. 23C-23I show insertion steps. FIG. 23C shows the needle tip of the implantation tool is inserted into the nose of the patient by the physician. FIG. 23D shows the needle is carefully navigated through the nasal tissue to ensure the path is in the correct position. The depth of the needle is monitored via visual cues integrated on the outside shaft. The depth is dictated by location of implant to bone. The location of the implantation tool can still be slightly altered up, down, right, and left. FIG. 23E shows that once at the correct depth and location, the needle is released and allowed to move relative to the stylet and implant. FIG. 23F shows the needle is removed from around the implant while the implant and stylet remained fixed. FIG. 23G shows the implant remains inside of the nasal tissue with the heating element interfacing with the implant. FIG. 23H shows the heater is activated and allowed to reach the correct temperature. FIG. 23I shows the heater warms the implant to allow it to become softened at the locations that need to be modified. FIGS. 23J-23N show implant shaping. FIG. 23J shows that once the implant is moldable, the implant is shaped by applying pressure with the shaping instrument. FIG. 23K shows that the heater is turned off and the shape of the implant is set by allowing it to cool. FIG. 23L shows the shape of the implant is verified and additional heating and shaping are applied if needed. FIG. 23M shows that with the stylet still engaged, the heating element is removed from around the implant. FIG. 23N shows the stylet and the implantation tool are removed from the patient. The custom shaped implant remains in the nasal tissue. A method of shaping an implant in a tissue may include the steps of placing an energy-response implant having a first shape into a nasal tissue; inserting an energy delivery element into an individual's nose; delivering energy from the energy delivering element to the implant to thereby increase a flexibility of the implant; shaping the implant into a second shape; and removing energy from the implant to thereby hold the implant in the second shape. Using such system or method may allow an implant to conform to a body tissue during shaping to provide a precise fit between an implant and a body tissue.

Figure 24A:
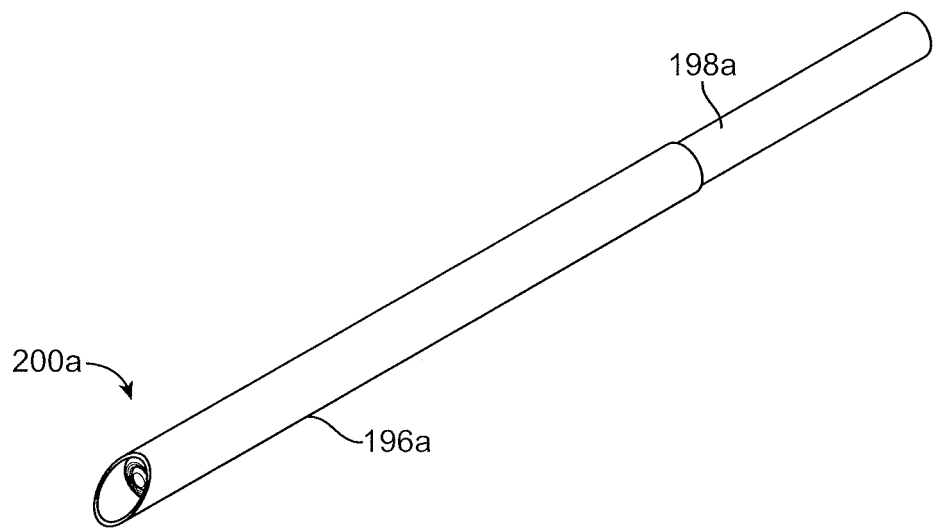
FIGS. 24A-24E show another embodiment of a system using energy for shaping an implant in a tissue in a body.
Figure 24B:
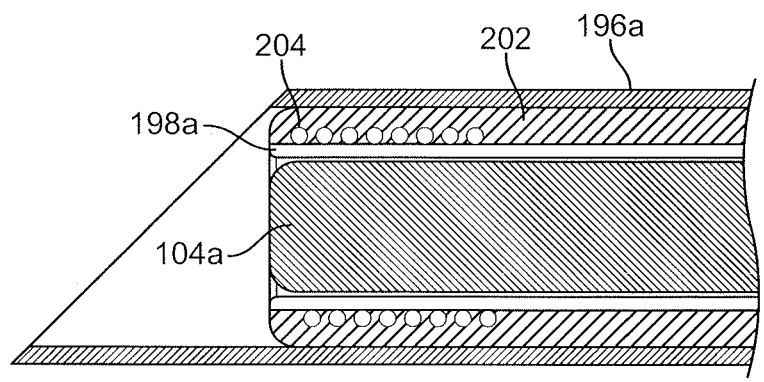
Figure 24C:
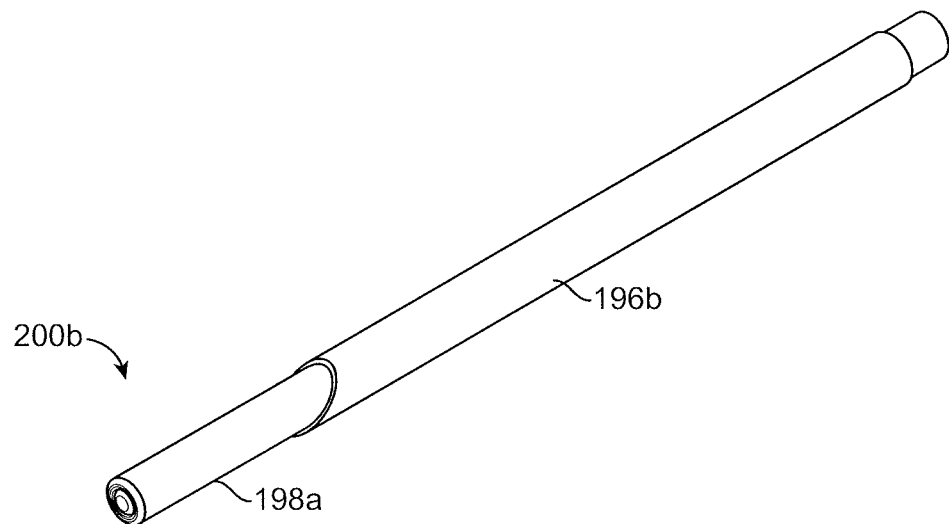
Figure 24D:
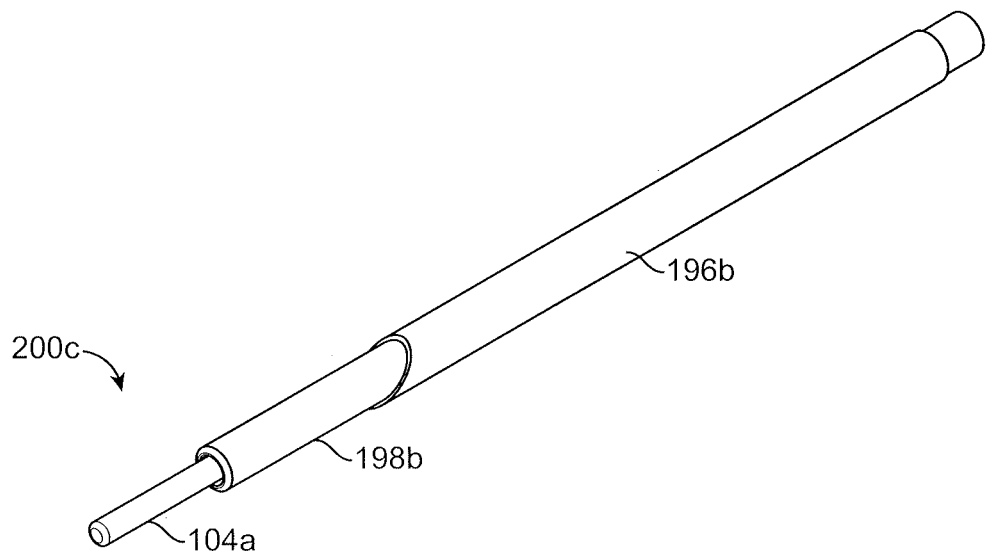
Figure 24E:
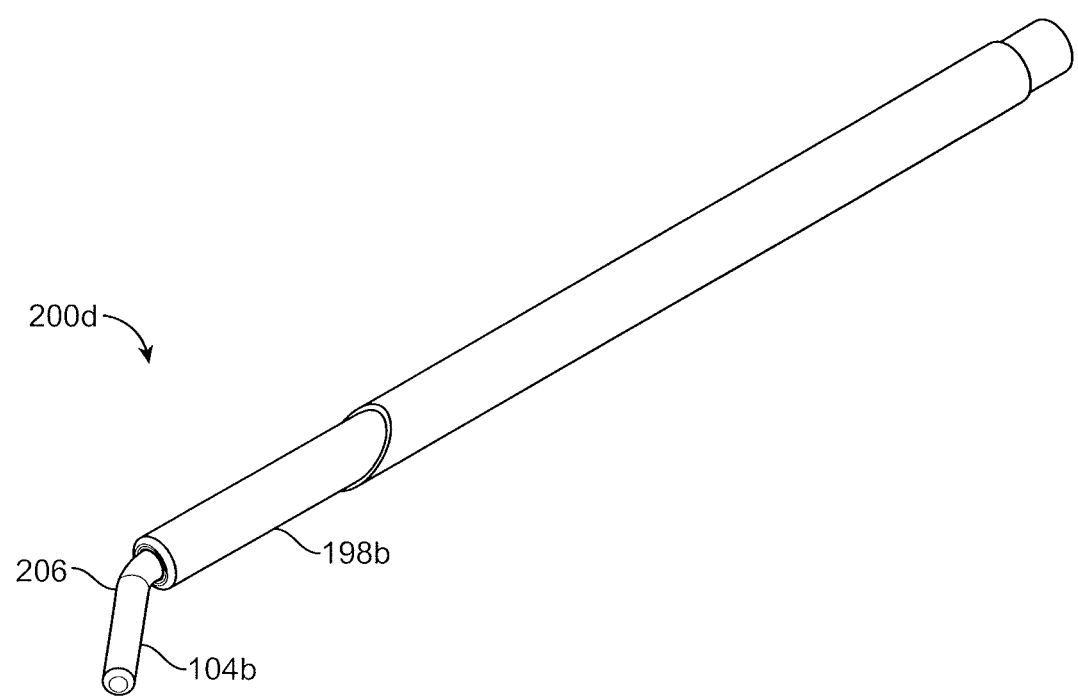

FIGS. 24A-24E shows another embodiment of a system 200 for shaping an implant using energy in a tissue in a body. FIG. 24A shows implant 104(*a*) is disposed inside cannula heating element 198*a* which in turn is disposed inside needle 1196*a* for the needle to deliver the cannula heating element and the implant to a desired implant tissue location for an implant in a nasal tissue. After delivering the implant 104(*a*), cannula 198*a*, and needle 196*b* to the desired location, needle 196*a* is retracted, as shown in FIG. 24C, unsheathing and leaving cannula 198*a* and implant 104*a* surrounded by cannula 198*a* in the desired implant tissue location. After heating the implant but protecting nasal tissue from excess heat with insulation 202, cannula 198*b* may be retracted, unsheathing and leaving heated (flexible) implant 104(*a*) in the desired tissue location. Implant 104*b* may be quickly shaped such as creating implant bend 206. Any external pressure (e.g., a tool pressed against an outside of the nose, or an internal pressure (e.g., a tool pressed against an inside of a nose) may be used to custom shape the implant to the nasal tissue.

In other embodiments, the needle may remain in position around the cannula during the heating steps. In other embodiments, the needle and cannula may comprise a single unit.

Steps in the method of using such a heating element may include: placing a hollow delivery conduit encompassing an implant in the nasal tissue, the implant having a first shape; heating a portion of the delivery conduit to thereby heat the implant; after the heating step, shaping the implant into a second shape; and retracting the conduit from the nasal tissue and from the implant to thereby place the implant in contact with the nasal tissue. In some embodiments, the delivery conduit comprises an internal portion (cannula) comprising insulation, and the method further comprising insulating the nasal tissue from the FIGS. 25A-25C show another embodiment of a system 196 for shaping an implant using energy in a tissue in a body. The system is a central axis heater, configured to deliver energy to an implant from an inside (center) of the implant. Energy responsive implant 198 has a hollow inside for accepting a heating element 204, which may be, for example, a rod or wire (e.g., a resistive wire, a thermally conductive rod). A resistive wire may allow an implant to be uniformly heated across its length. FIG. 25A shows a system 196 during insertion into a nasal tissue with needle 102*a* encompassing implant 198*a* which in turn encompasses heating element 204. (The system maintains the same configuration it had just prior to being inserted into the nasal tissue). As shown in FIG. 25B and as described elsewhere, after insertion into a desired location in a tissue, needle 102*b* is retracted, unsheathing implant 198*a*. The heater is activated until the implant is above Tg. Once above Tg, the implant is freely shaped. When the desired shape is achieved, the heater is deactivated, allow the implant to cool below Tg (which may be less than, for example, 20 seconds).

The heater element inside the heater element is retracted while the back of the implant is held in place, as shown in FIG. 25C. The device is then retracted off the implant.

FIGS. 26A-26D show another embodiment of a system 224 for shaping an implant using energy in a tissue in a body, an integrated implanting and heating system with a central axis heater. The system integrates implanting manipulation functions including needle retraction and heating functions including heating control and heater retraction into a single housing. The system may be used with any implant or heat system, but may be especially useful with an implant system with a central axis heater for heating an implant, such as the one described in FIGS. 25A-25C. FIG. 26A shows a perspective view and FIG. 26B shows a cross-section view of the system during implant delivery and before heating. FIG. 26C shows a section view of the system after retracting the needle, but before heating and shaping are completed.

System 224 has a grippable housing 226. System 224 includes a heater on/off switch 236 for controlling the heat to the heater, a battery 234 (e.g., energy source) for providing heat to the heater, and an LED indicator light 238 to indicate when shaping can occur. System 224 further includes a needle retraction button 228 which controls a slider retraction mechanism 232 for connecting with and retracting the needle away from the implant (desheathing) after the implant has been placed in position in the tissue. System 224 further includes a heater retraction knob 230 connected with a pulley mechanism for retracting the heater. FIGS. 26A and 26B show the steps of inserting needle 102 to a desired location in a nasal tissue; and unlocking needle retraction button 228a. FIG. 26C shows sliding needle retraction button 228b to end of travel to retract the needle and unsheath the implant. FIG. 26C also illustrates the steps of turning on heater on/off button 236, waiting for LED indicator light 238 to turn on, indicating an implant is ready to be shaped from a first shape to a second shape by activating LED indicator light 238, shaping implant into a second shape (not readily seen in this view). FIG. 26D illustrates indicating that an implant is sufficiently cooled (e.g. for an implant to hold its second shape), turning the heater retraction knob 230 to activate pulley retraction mechanism 240 and retracting heater 204a out of implant 104. Finally, the assembly is removed from the nasal tissue.

Figure 27A:
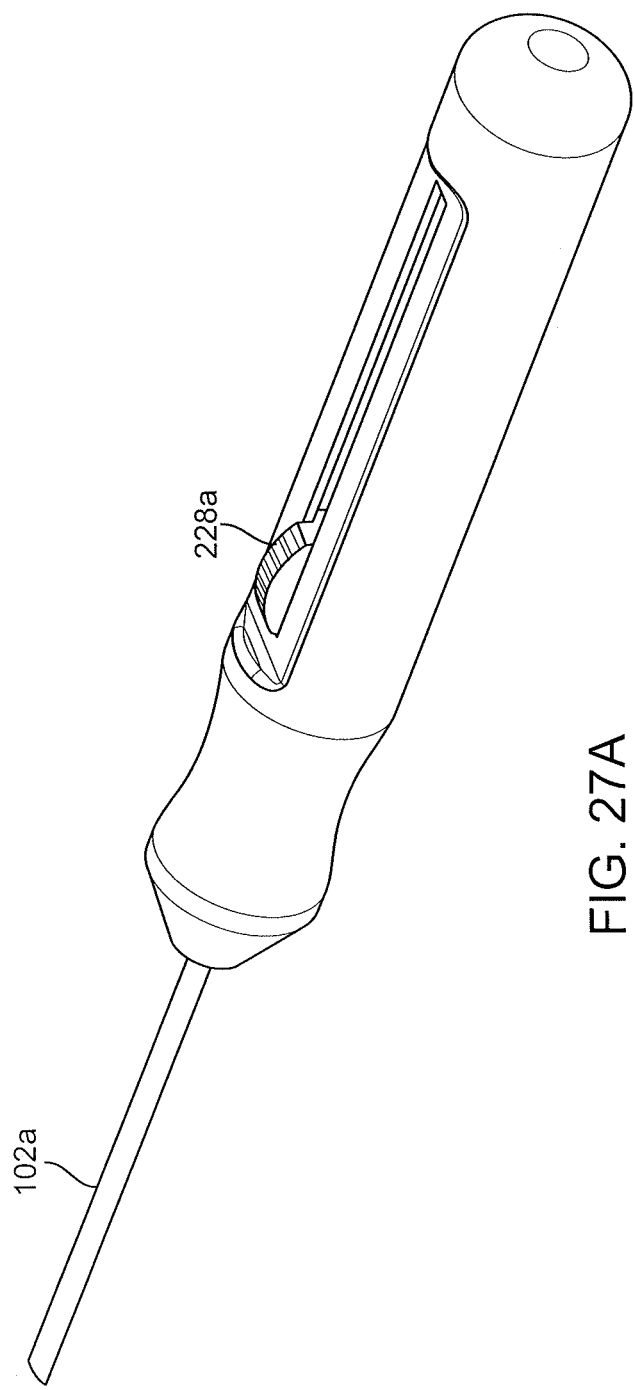
Figure 27D:
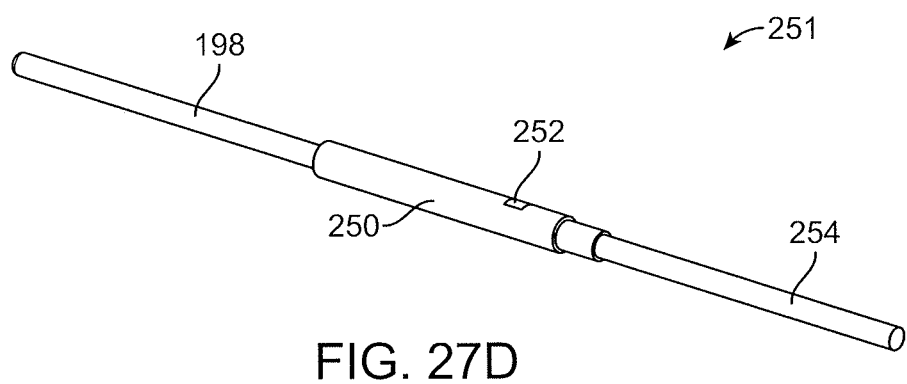
Figure 27E:
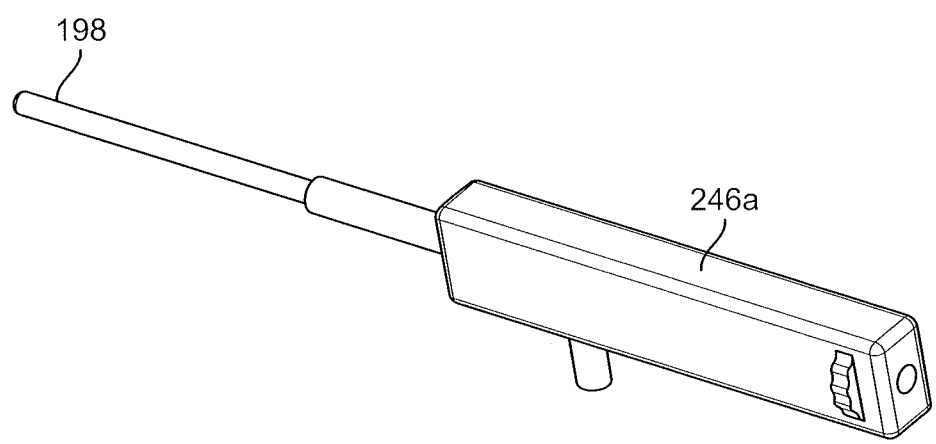
Figure 27F:
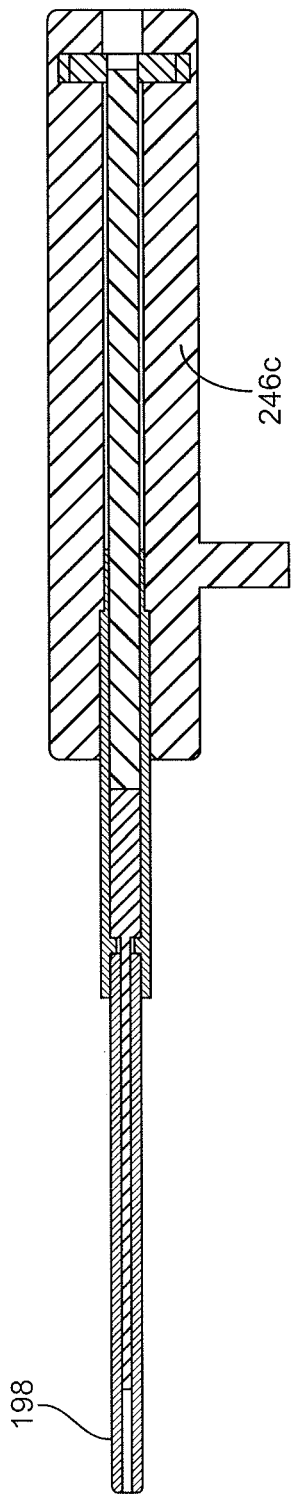
Figure 27G:
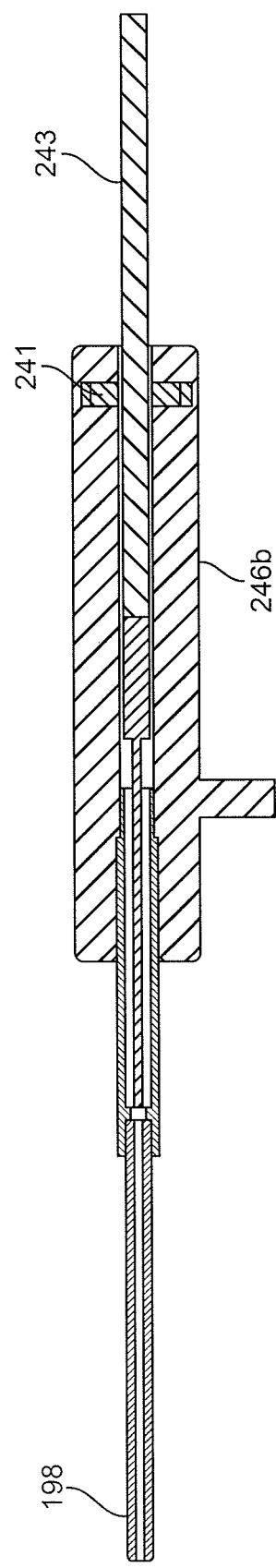
Figure 28:
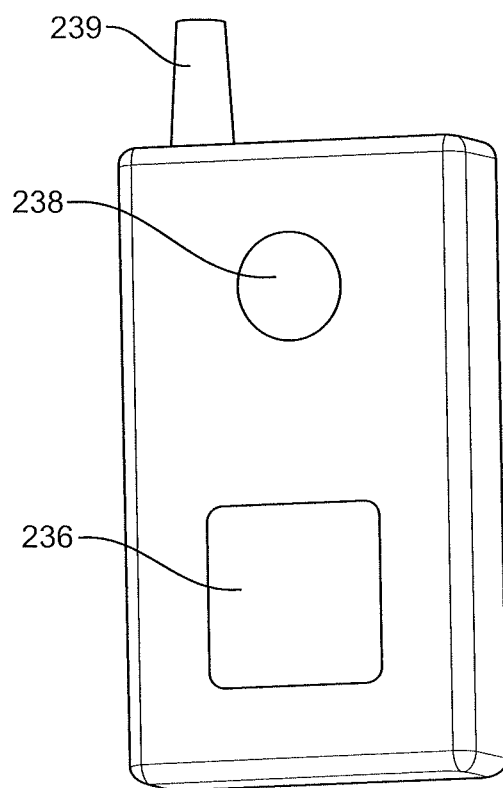
FIG. 28 shows an embodiment of a heating device and battery that can be used with a system using energy for shaping an implant in a tissue in a body, such as the system shown in FIGS. 27A-27G.

FIGS. 27A-27G and FIG. 28 show another embodiment of a system 242 for shaping an implant using energy in a tissue in a body. The system separates implanting manipulation functions including needle retraction in a first housing, heating functions including heating control and heater retraction into a second housing and battery and heat control into a third housing. The system may be used with any implant or heat system, but may be especially useful with an implant system with a central axis heater for heating an implant, such as the one described in FIGS. 25A-25C. FIG. 27A shows a perspective view and FIGS. 27B-27C show cross-sectional views of the needle control housing during use. FIGS. 27D-27G show views of the heating and retraction device during use. FIG. 28 shows a view of the battery and heat control housing.

System 242 has a first grippable housing 244 for controlling a needle. System 242 includes a first grippable housing 244 including a needle retraction button 228 which controls a slider retraction mechanism 232 for connecting with and retracting the needle away from the implant (desheathing) after the implant has been placed in position in the tissue. System 242 includes a second grippable housing 246 including a heating and retracting device. System 242 includes third housing 248 with a heater, a heater on/off switch 236 for controlling the heat to the energy delivery element, a battery 234 for providing heat to the heater, and an LED indicator light 238 to indicate when shaping can occur and when the implant has cooled sufficiently to hold its shape.

FIGS. 27A and 27B show steps of inserting needle 102 into nasal tissue and unlocking needle retraction button 228. FIG. 27C shows the steps of sliding needle retraction button 228 to the end of travel and locking the needle retraction button. FIGS. 27C and 27D show removing the implanting device from the heater and implant by twisting away and leaving energy responsive implant 198 attached to frame 250, including electrical contact 252 and threaded rod 254 for heater retraction. FIGS. 27E and 27F show attaching heating and retraction device 246a to implant and heater 254. FIG. 27G shows a section view of an implant, heater, and retraction device with the heater retracted. It includes a one-direction, torque limiting threaded nut 241 and threaded rod 243 connected to the heater. FIG. 28 shows the third housing with battery pack and heater controller 248 which can be attached by electrical wires 239 to heating and retraction device 246. The third housing with battery pack and heater controller 248 is turned on using heater on/off button 236. Once LED indicator light 238 turns on, implant 198 is shaped (such as described elsewhere). After LED indicator light 238 turns off, a heater retraction knob on the second grippable housing-implant, heating and retraction device 246 is turned to moved threaded rod 254 (shown in FIG. 27D) and retract heater out of the implant, as shown in FIG. 27F.

Any of the above described systems, assemblies, or methods may employ an energy responsive implant. An energy source may raise the temperature of the implant above its glass transition temperature (Tg) so that it can be shaped. When a material is above its Tg, it can be freely shaped. When the material temperature falls below the Tg, a material will hold its shape.

Any of the any of the above described systems, assemblies, or methods may use a heater tool to apply force to shape an implant. After shaping, the heating tool may be removed.

Figure 29:
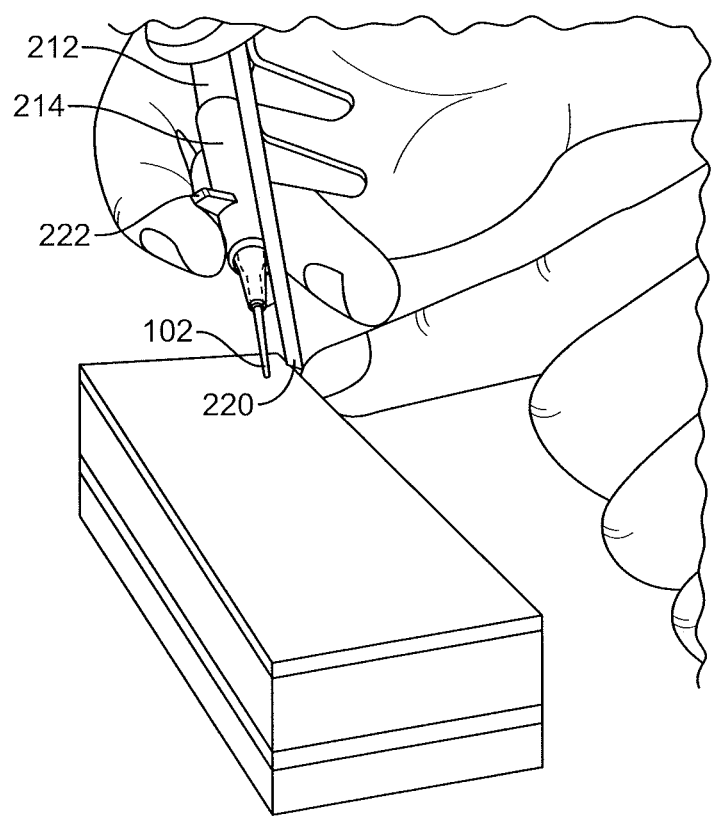
FIG. 29 shows an embodiment of an assembly with a support member useful for holding an implant delivery device in place during use.
Figure 30:
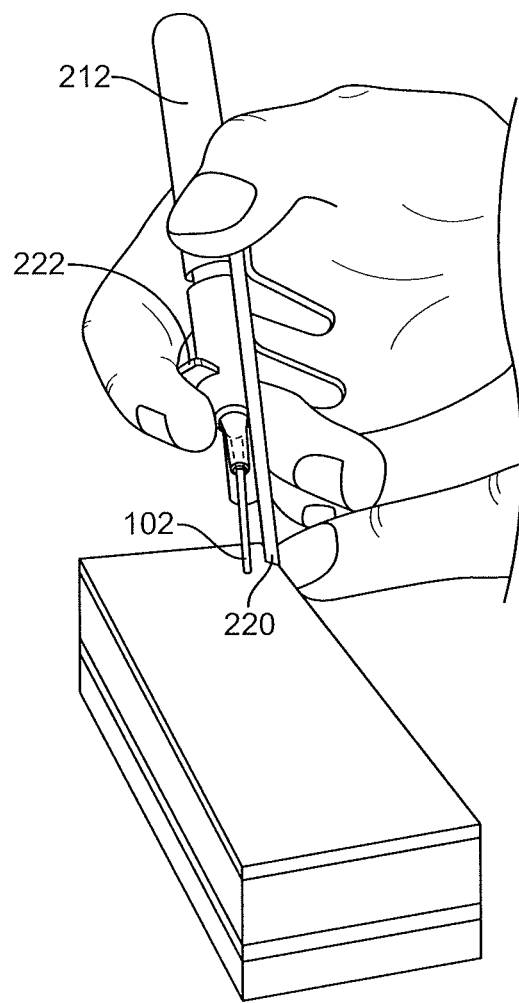
FIG. 30 shows another view of an assembly with a support member useful for holding an implant delivery device in place during use.
Figure 31:
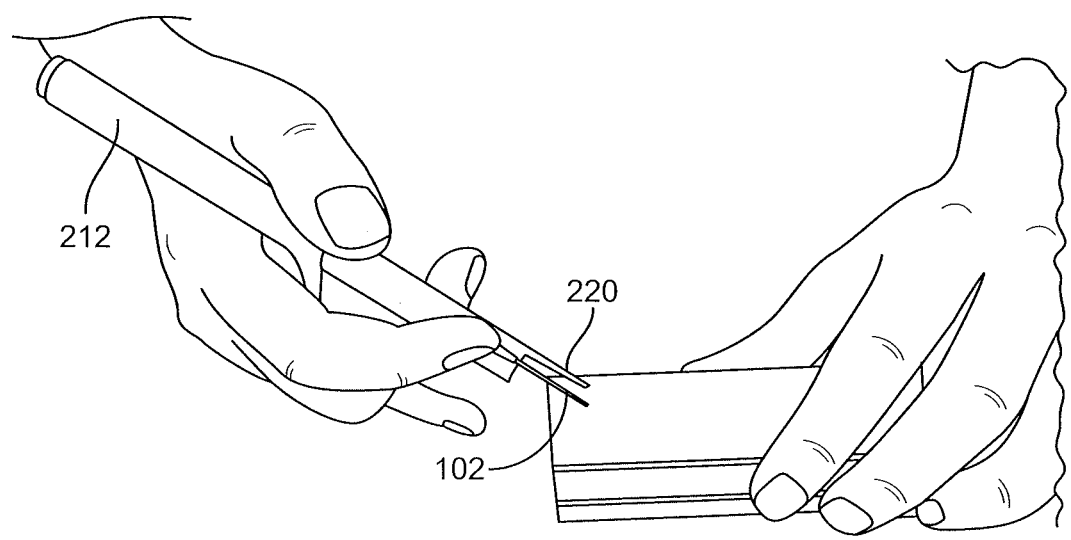
FIG. 31 shows another view of an assembly with a support member useful for holding an implant delivery device in place during use.

FIGS. 29-31 show an assembly 212 including a housing support member 216 connected with grippable housing 214, with distal end 220 of support member configured to abut a patient's face during support member use. Such a housing support member may help hold assembly 212 in place (e.g. with minimal or essentially no movement) on the patient's face during assembly use, such as while retracting the needle away from the implant; this keeps the implant in a desired implant location during needle retraction. In some embodiments, a housing support member may be an extension from the distal face of the assembly. In some embodiments a housing support member may be slidable from the body of the delivery tool. In some embodiments, a housing support member may be spring loaded (e.g., comprising a rigid spring). In some embodiments, steps in using a housing support member may include moving the housing support member to contact a face of a patient, and locking the housing support member in place. In some embodiments, steps in using a housing support member may include moving the housing support member to contact a face of a patient, and sliding the housing support member proximally while inserting the needle in the nasal tissue. In some embodiments, wherein the grippable housing is connected with a housing support member, a method of implanting an implant into a nasal tissue of a patient may include the step of contacting the housing support member with a face of a patient to thereby hold the housing in place on the face of the patient during the retracting the delivery conduit from the implant step. In order to place the implant (not visible in these figures) in the tissue, a physician or other user may pull on trigger 222 to retract needle 102 (e.g., retract needle 222 proximally) out of the tissue. The needle may be retracted relative to housing 214 and relative to housing support member 216. Housing 214 and housing support member 216 may remain stationary (e.g., not move relative to one another) during the needle retraction step.

An assembly for placing an implant in a nasal tissue, such as described herein, may further comprise a support member connected with the housing, the support member configured to abut a portion of a face of a patient when an assembly is in use on the patient.

FIGS. 32A-32D show a nasal implant system 3200 according to yet another embodiment of this invention. The system has a grippable housing 3204 supporting an implant holder 3206. An implant 3202 such as, e.g., one of the implants described with respect to FIGS. 10A-10N above, is loaded into the implant holder 3206, and a needle 3208 (such as, e.g., a 16 g beveled hypodermic needle) is attached to the housing over the implant via internal threads on needle actuator 3220.

Figure 32A:
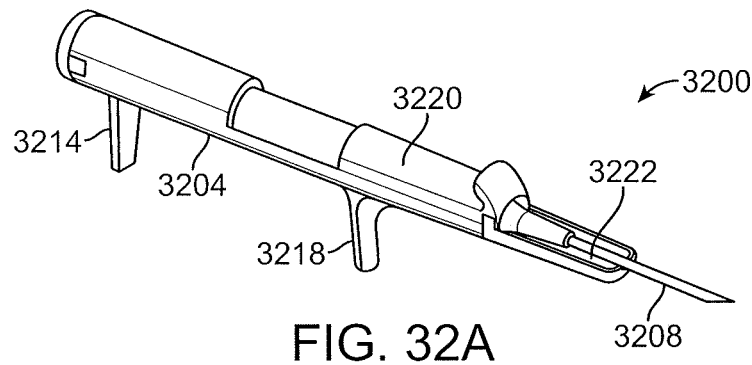
FIGS. 32A-32D show different views of another embodiment of a nasal implant system that may be useful for holding an implant in position in a tissue during needle retraction.
Figure 32B:
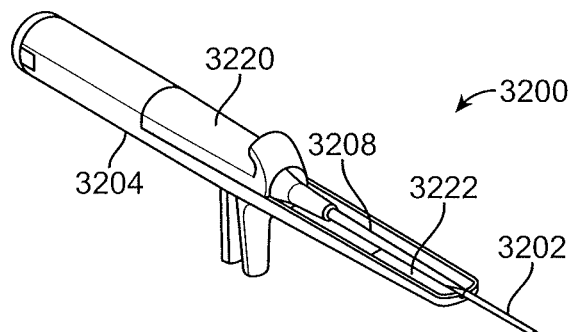
Figure 32C:
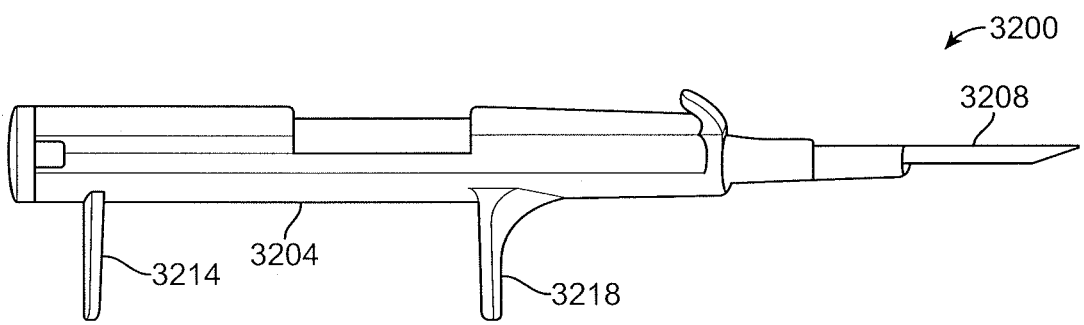
Figure 32D:
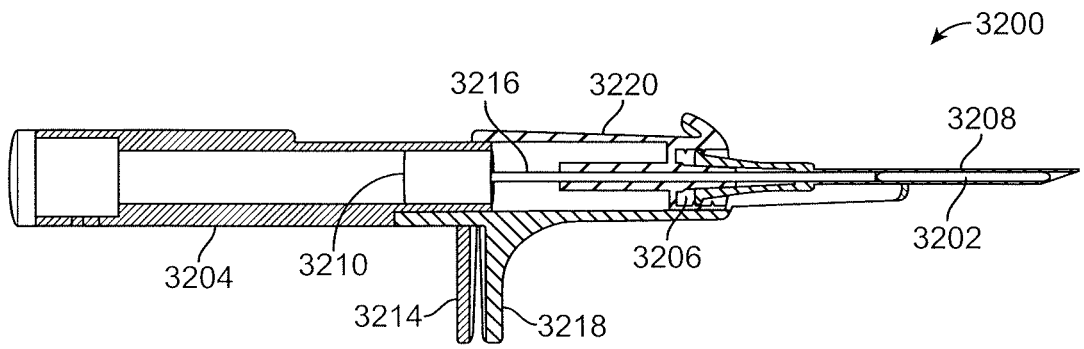

A piston 3210 is slidably disposed within a bore 3212 of housing 3204, and a handle 3214 extends from piston 3210 to the underside of housing 3204. A pusher 3216 extends from piston 3210 into implant holder 3206. Movement of handle 3214 toward a stationary handle 3218 advances the pusher 3216 through the implant holder 3206 to push the implant 3202 distally into needle 3208. When the two handles meet, the distal end of implant 3202 is at the beveled opening of needle 3208, as shown in FIG. 32D. In use, after the needle has been inserted into the desired location in the patient's nose, the needle 3208 may be retracted from the implant 3202 by moving the needle actuator 3220 proximally to the position shown in FIG. 32B. The pusher holds the implant in position while the needle is retracted. In some embodiments, handle 3214 may be moved further distally after insertion of the needle into nasal tissue but before retraction of the needle to push the implant further distally, e.g., to the distal end of the needle's beveled opening. An opening 3222 in the distal portion of the housing enables the user to observe and confirm needle retraction.

Figure 33A:
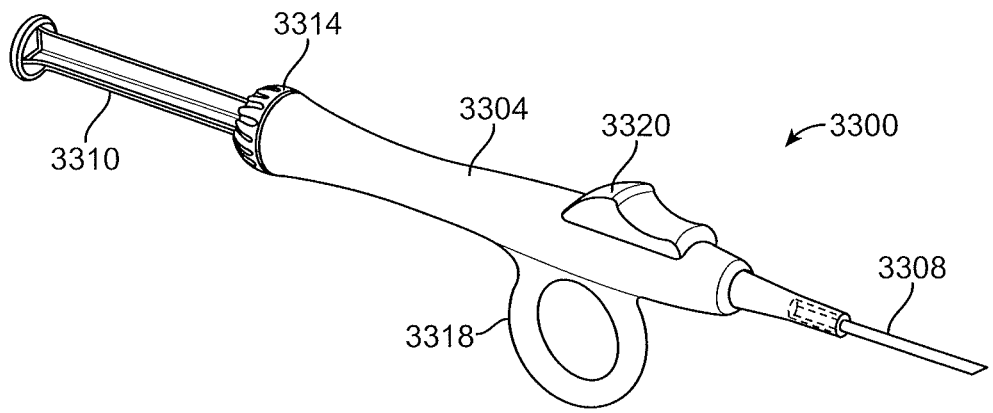
FIGS. 33A-33C show different views of another embodiment of a nasal implant system that may be useful for holding an implant in position in a tissue during needle retraction.
Figure 33B:
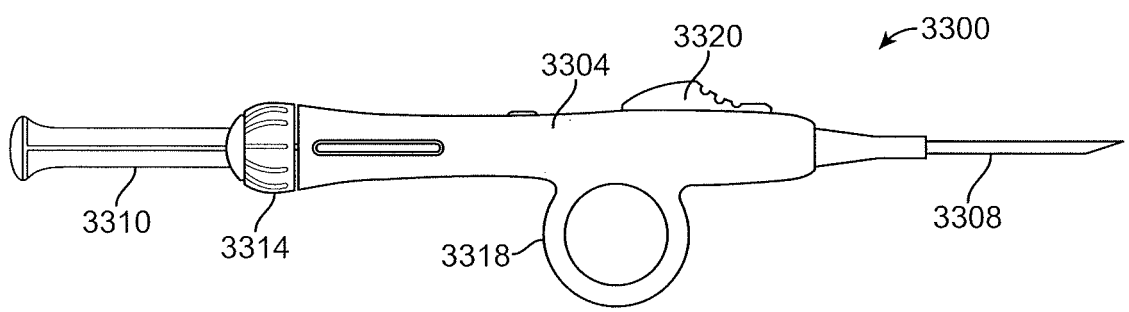
Figure 33C:
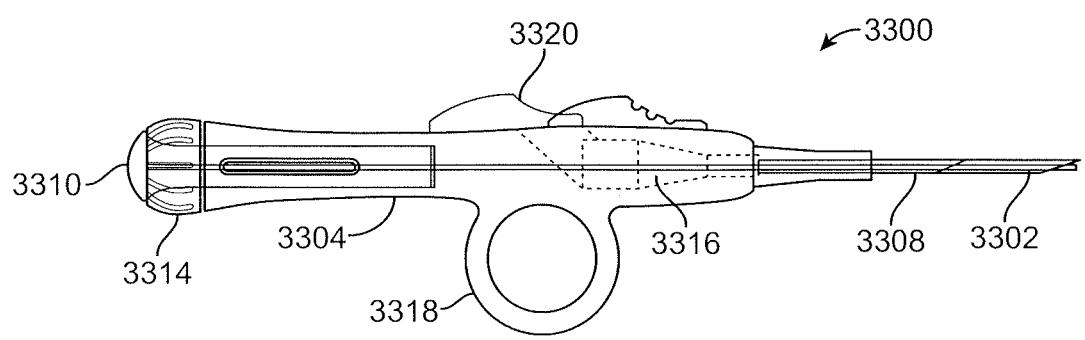

FIGS. 33A-33C show a nasal implant system 3300 according to another embodiment of this invention. The system has a housing 3304 supporting an implant holder (not shown). An implant 3302 such as, e.g., one of the implants described with respect to FIGS. 10A-10N above, is loaded into the implant holder, and a needle 3308 (such as, e.g., a 16 g beveled hypodermic needle) is attached to the housing over the implant via internal threads on needle actuator 3320.

As shown in FIGS. 33A and 33B, an implant actuator 3310 extends proximally from the housing. A pusher 3316 extends distally from the implant actuator 3310 through the housing to the implant holder. Distal movement of the implant actuator 3310 toward the housing moves the pusher toward the implant and the implant out of the implant holder and into the needle to place the distal end of the implant at the beveled opening of the needle. Thereafter, proximal movement of the needle actuator 3320 retracts the needle from the implant while the pusher holds the implant stationary, as shown in FIG. 33C. In some embodiments, a rotary dial 3314 may be turned after insertion of the needle into nasal tissue but before retraction of the needle to push the implant further distally, e.g., to the distal end of the needle's beveled opening. A ring grip 3318 extending from the housing assists in holding the housing stably.

Figure 34A:
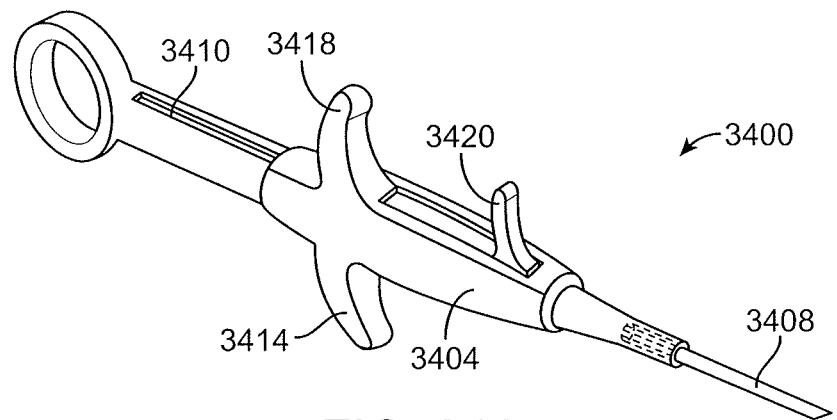
FIGS. 34A-34C show different views of another embodiment of a nasal implant system that may be useful for holding or pushing an implant in position in a tissue during needle retraction.
Figure 34B:
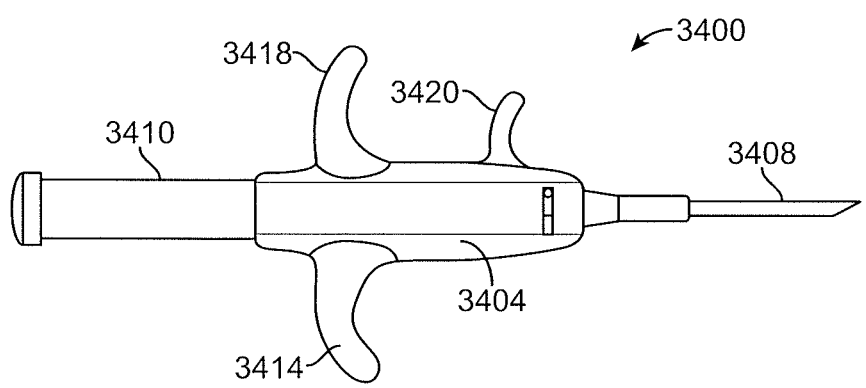
Figure 34C:
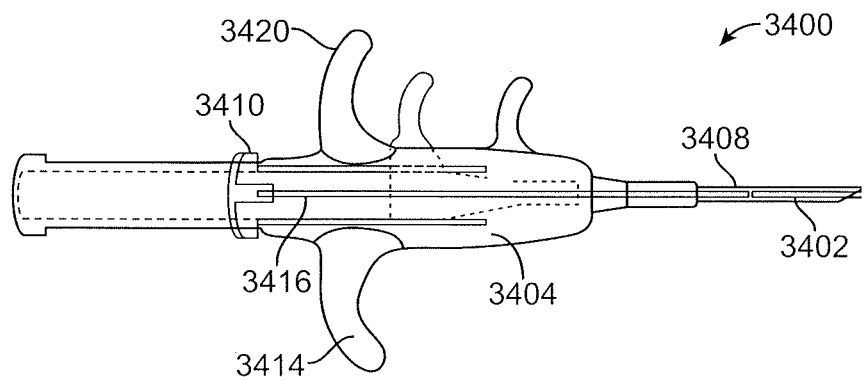

FIGS. 34A-34C show a nasal implant system 3400 according to yet another embodiment of the invention. The system has a housing 3404 supporting an implant holder (not shown). An implant 3402 such as, e.g., one of the implants described with respect to FIGS. 10A-10N above, is loaded into the implant holder, and a needle 3408 (such as, e.g., a 16 g beveled hypodermic needle) is attached to the housing over the implant via internal threads on needle actuator 3420.

As shown in FIGS. 34A and 34B, an implant actuator 3410 extends proximally from the housing. The implant actuator may have, e.g., a ring or cap at is distal end as shown in FIGS. 34A and 34B, respectively. A pusher 3416 extends distally from the implant actuator 3410 through the housing to the implant holder. Distal movement of the implant actuator 3410 toward the housing moves the pusher toward the implant and the implant out of the implant holder and into the needle to place the distal end of the implant at the beveled opening of the needle, as shown in FIG. 34C. Thereafter, proximal movement of the needle actuator 3420 retracts the needle from the implant while the pusher holds the implant stationary, as shown in FIG. 34C. In some embodiments, the implant actuator may be moved further distally after insertion of the needle into nasal tissue but before retraction of the needle to push the implant further distally, e.g., to the distal end of the needle's beveled opening. Handles 3414 and 3418 extend from the housing to assist in holding the housing stably.

Figure 35A:
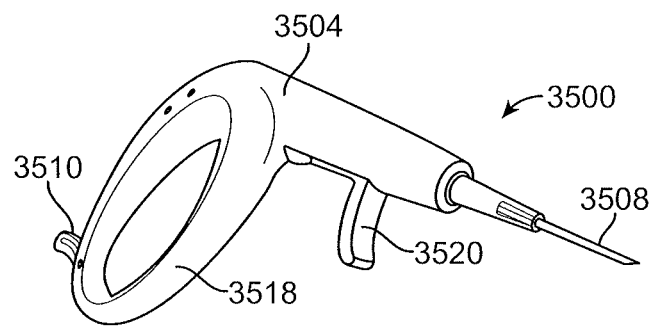
FIGS. 35A-35C show different views of another embodiment of a nasal implant system that may be useful for holding or pushing an implant in position in a tissue during needle retraction.
Figure 35B:
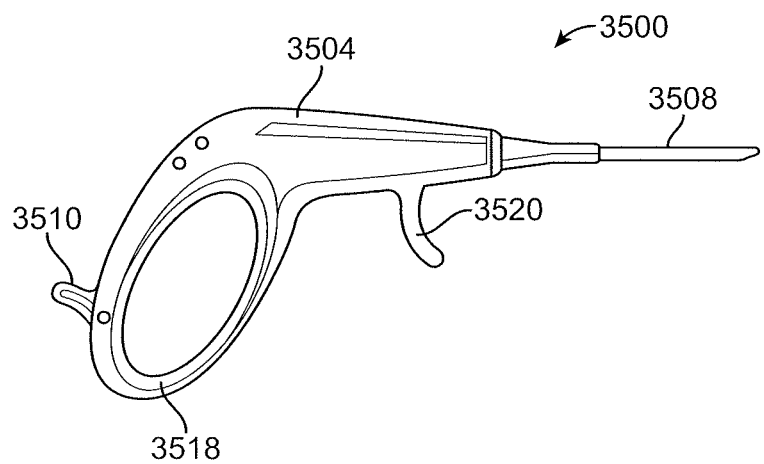
Figure 35C:
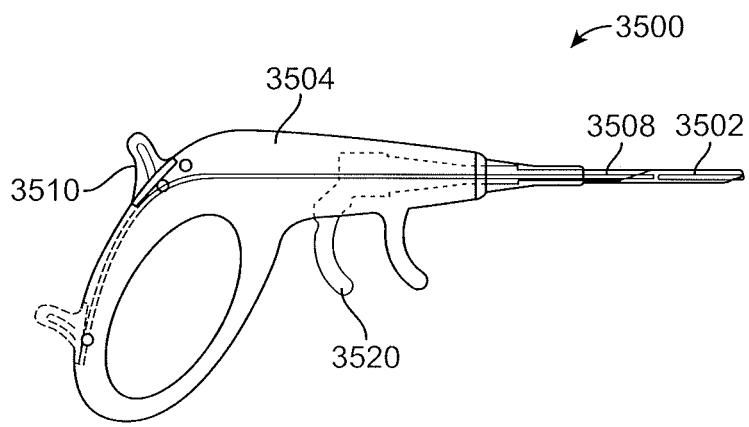

FIGS. 35A-35C show a nasal implant system 3500 according to still another embodiment of the invention. The system has a housing 3504 supporting an implant holder (not shown). An implant 3502 such as, e.g., one of the implants described with respect to FIGS. 10A-10N above, is loaded into the implant holder, and a needle 3508 (such as, e.g., a 16 g beveled hypodermic needle) is attached to the housing over the implant via internal threads on needle actuator 3520.

As shown in FIGS. 35A and 35B, an implant actuator 3510 extends proximally from the housing. A pusher 3516 extends distally from the implant actuator 3510 through the housing to the implant holder. Sliding movement of the implant actuator 3510 within a track in the housing to the position shown in FIG. 35C moves the pusher into and the implant out of the implant holder and into the needle to place the distal end of the implant at the beveled opening of the needle. Thereafter, proximal movement of the needle actuator 3520 retracts the needle from the implant while the pusher holds the implant stationary, as shown in FIG. 35C. In some embodiments, the implant actuator may be moved further within the track in the housing after insertion of the needle into nasal tissue but before retraction of the needle to push the implant further distally, e.g., to the distal end of the needle's beveled opening. A ring or handle 3518 extends from the housing to assist in holding the housing stably.

Figures 36A, 36B, 36C, 36D, 36E, 36F:
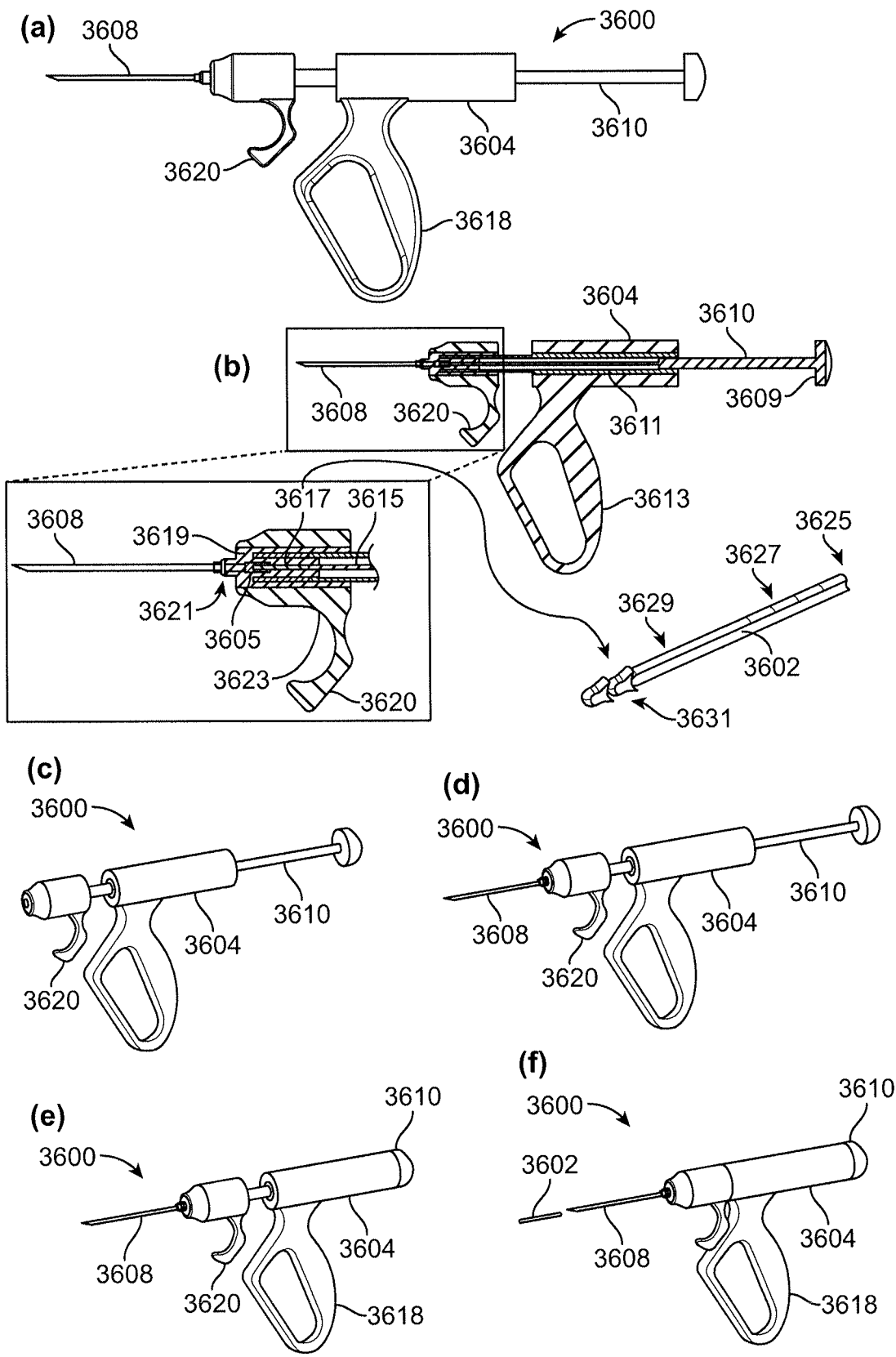
FIGS. 36A-36F show different views of another embodiment of a nasal implant system for holding or pushing an implant in position in a tissue and for holding an implant in an expanded configuration.

FIGS. 36A-36F show a nasal implant system 3600 according to another embodiment of the invention. The system has a housing 3604 supporting an implant holder (not shown) and a pistol grip 3613 having a proximal pistol grip skin 3613 and a distal trigger skin 3623. An implant 3602 is loaded into the implant holder, and a needle 3608 (such as, e.g., a 16 g beveled hypodermic needle) is attached to the housing over the implant via internal threads on needle actuator 3620, such as via luer 3621. The implant 3602 may be formed from a bio-absorbable material that may include various combinations of PLA, PDLA, PDS, PLC, PGA, PLG or similar. As shown in FIG. 36B, implant 3602 is substantially round in cross section and approximately 25 mm in length. There are convex or concave ring features on the proximal end of the rod (spaced, e.g., every 1 mm, 2.5 mm, or 5 mm from the end) to show the user positions to cut the rod to achieve a specific length. The implant has barbed or tined features 3631 at the distal end. These features may be made by cutting into the implant with a blade at a 30-45 degree angle, then bending the outer portion of the implant material to its plastic deformation point. These barbs would be flexible enough to collapse inward (i.e., into the original position prior to barb formation) when introduced into needle 3608 and resilient enough to expand when the implant is released from the needle into nasal tissue. The barbs will engage the surrounding nasal tissue to prevent migration of the implant back out through its implantation path so that it maintains its therapeutic position, e.g., overlaying the maxillary interface. Implant 3602 also has proximal length markers 3627 and a proximal cup face 3625.

A plunger-shaped implant actuator 3610 extends proximally from the housing. A pusher 3616 extends distally from the implant actuator 3610 through the housing to the implant holder (through the proximal handle core 3611). The distal face of the pusher 3616 is concave to mate with the rounded proximal end of the implant to, e.g., center the implant on the pusher. Distal movement of the implant actuator 3610 (such as with plunger head 3609) toward within the housing from the position shown in FIG. 36A to the position shown in FIG. 36E moves the implant out of the implant holder and into the needle to place the distal end of the implant at the beveled opening of the needle. Thereafter, proximal movement of the needle actuator 3620 retracts the needle from the implant while the pusher holds the implant stationary, as shown in FIG. 36F. A handle 3618 extends from the housing to assist in holding the housing stably.

A window 3605 in housing 3604 permits the barbs to remain extended until the implant is loaded into the needle. This feature enables the implant to remain in the system for an extended period of time (e.g., during packaging, sterilization, transportation and inventory storage) without an adverse effect on the position and resilience of the barbs due to polymer creep.

Figure 37A:
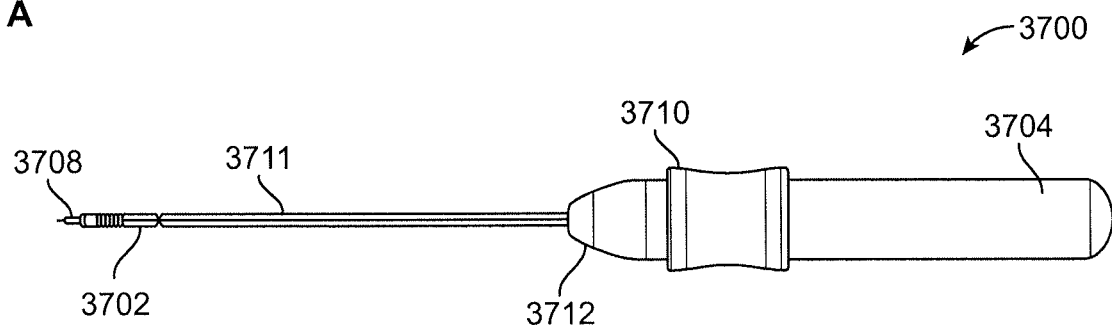
FIGS. 37A-37C show different views of another embodiment of a nasal implant system useful for delivering a hollow implant to a nasal tissue.
Figure 37B:
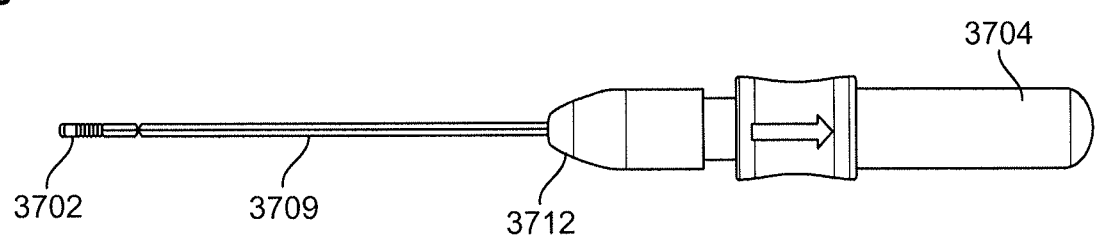
Figure 37C:
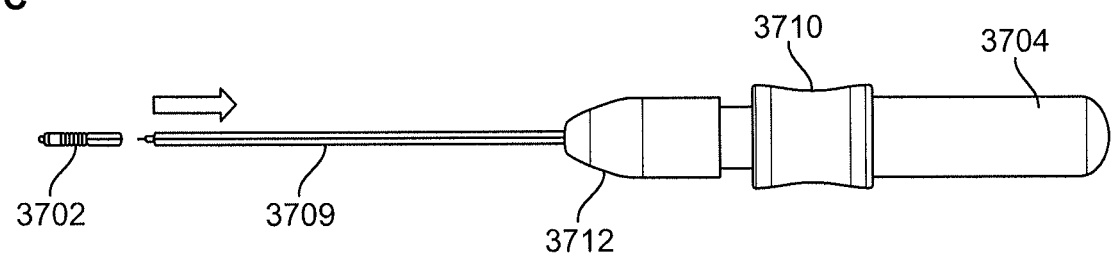

FIGS. 37A-37C show a nasal implant system 3700 according to yet another embodiment of the invention. System includes a substantially cylindrical main body 3704, a slidable ring trigger 3710, a rod-like piercing element 3708 extending through a tool shaft 3709, and a hollow implant 3702. This nasal implant delivery tool is configured to deliver the hollow rod implant 3702 to the nasal anatomy in a similar manner to the systems discussed above. In this embodiment, however, the piercing element 3708 extends through the hollow implant 3702 and retains the implant with a friction fit. The proximal end of the implant rests against the distal surface of the tool shaft. Once the implant and supporting piercing element are inserted into the nasal anatomy and positioned, e.g., against the maxilla, the entire tool (or, alternatively, the inner piercing element alone) may be retracted to deposit the implant at its target location. The implant 3702 may have barbs, as discussed above that interact with nasal tissue to maintain the implant in position as the delivery tool is retracted. In use, the tool and implant are inserted into nasal tissue in the configuration shown in FIG. 37A. Once in the desired location, the trigger ring 3710 is retracted, as shown in FIG. 37B, thereby releasing the implant 3702. The tool shaft and piercing element are thereafter withdrawn from the implant and the nasal tissue, as shown in FIG. 37C.

The nasal implants of this invention may be formed in larger bodies made up of a plurality of individual implants. For example, as shown in FIG. 38, a sheet 3800 is made up of multiple implants 3802 connected by offset bridges 3804. An implant 3802 may be separated from the sheet 3800 by severing the bridges connecting it to the adjacent implant 3802. The implant material may be PLA, PDLA, PDS, PLC, PGA, PLG or similar bio-absorbable material.

FIGS. 39A-39D show a delivery tool 3900 with a feature enabling it to separate individual implants from a sheet of implants, such as the sheet 3800 shown in FIG. 38. Delivery tool 3900 has a two part body, a proximal main body 3904 and a distal trigger body 3906. A opening or window 3908 in trigger body is size to accept a sheet 3910 formed of multiple implants 3912 so that the first implant segment lines up with the inner bore of introducer needle 3914, as shown in FIGS. 39B and 39C. A cutting element 3916 has a sharp edge extending towards the implant sheet and lining up with the bridges holding the first implant on the sheet to the rest of the sheet, as shown in FIG. 39C. Distal movement of a push rod plunger or actuator 3928 moves a push rod 3930 distally so that sheet 3910 moves toward cutting element 3916. As it advances, the cutting element shears the bridges holding the first implant to the rest of the sheet, and the implant is advanced into the bore of needle 3914, as shown in FIG. 39D. The push rod 3930 continues to advance the single implant 3912 to the distal end of needle 3914, as discussed in connection with other embodiments above.

Figures 40A, 40B, 40C:
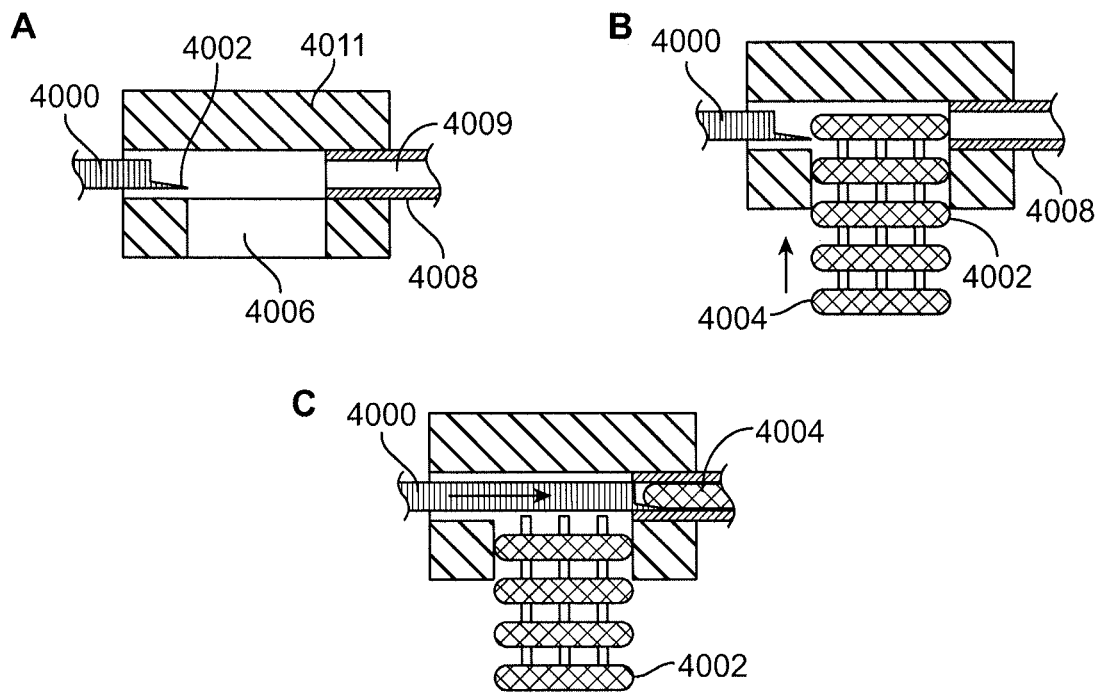
FIGS. 40A-40C show another embodiment of a delivery tool for separating an implant from a sheet of implants, such as the sheet shown in FIG. 38, using a pusher and for delivering the implant to a nasal tissue.
Figures 41A, 41B, 41C, 41D:
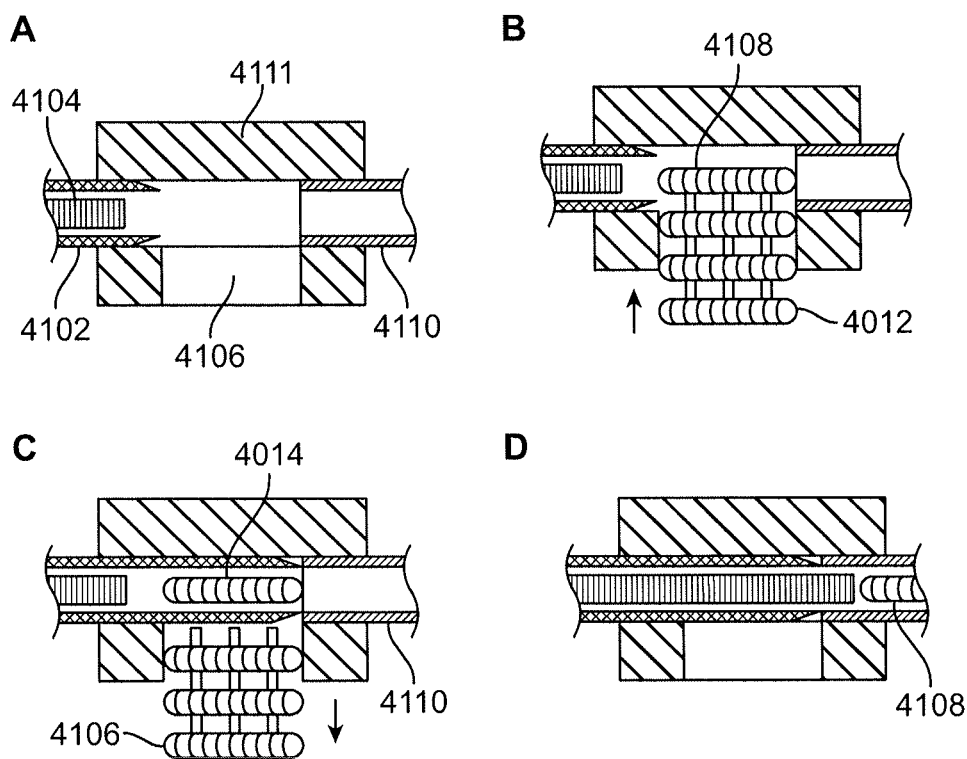
FIGS. 41A-41D show another embodiment of a delivery tool for separating an implant from a sheet of implants, such as the sheet shown in FIG. 38, for shearing the implant, shaving the outer surface of the implant, for delivering the implant to a nasal tissue.

FIGS. 40A-40C show portions of another embodiment of a delivery tool with features enabling a single implant to be cut from a sheet of implants. The tool may be formed similar to tool 3900 described above with a distal trigger housing 4009. Instead of a stationary cutting tool extending toward the sheet of implants, the pusher 4000 in the embodiment of FIG. 40 has a sharp distal edge 4002. A sheet 4002 of individual implants 4004 connected by bridges is advanced into the delivery tool through a window 4006 in the tool body so that the first implant lines up with the bore of introducer needle 4008 (with needle inner bore 4009). Distal movement of the pusher 4000 and sharp distal edge 4002 causes the first implant to shear from the sheet and move into the bore of needle 4008, as shown in FIG. 40C.

In yet another alternative embodiment shown in FIGS. 41A-41D with distal trigger housing 4111, the cutting may be annular so that it both shears the single implant from the sheath and shaves the outer surface of the single implant to ensure that it fits cleanly within the bore of the needle. The cutting tool 4102 and the pusher 4104 may be separate elements, with the annular cutting tool 4102 (such as a hypotube) being advanced over the pusher 4104 to perform the shearing and shaving operations to remove implant 4108 from sheet 4012, and the pusher moving distally to advance the implant 4106 into the needle 4110. The cutting tool has an implant side window 4106.

Figure 42:
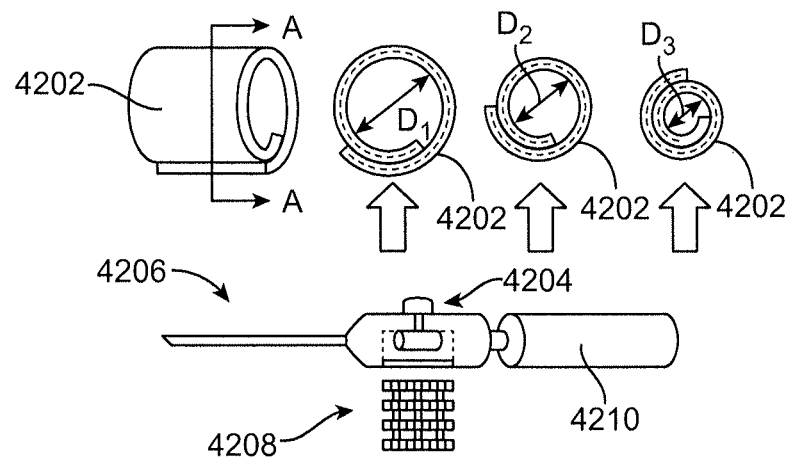
FIG. 42 shows an embodiment of an adjustable delivery tool adjustable useful for handling different sizes of implants.
Figures 43A, 43B, 43C, 43D, 43E:
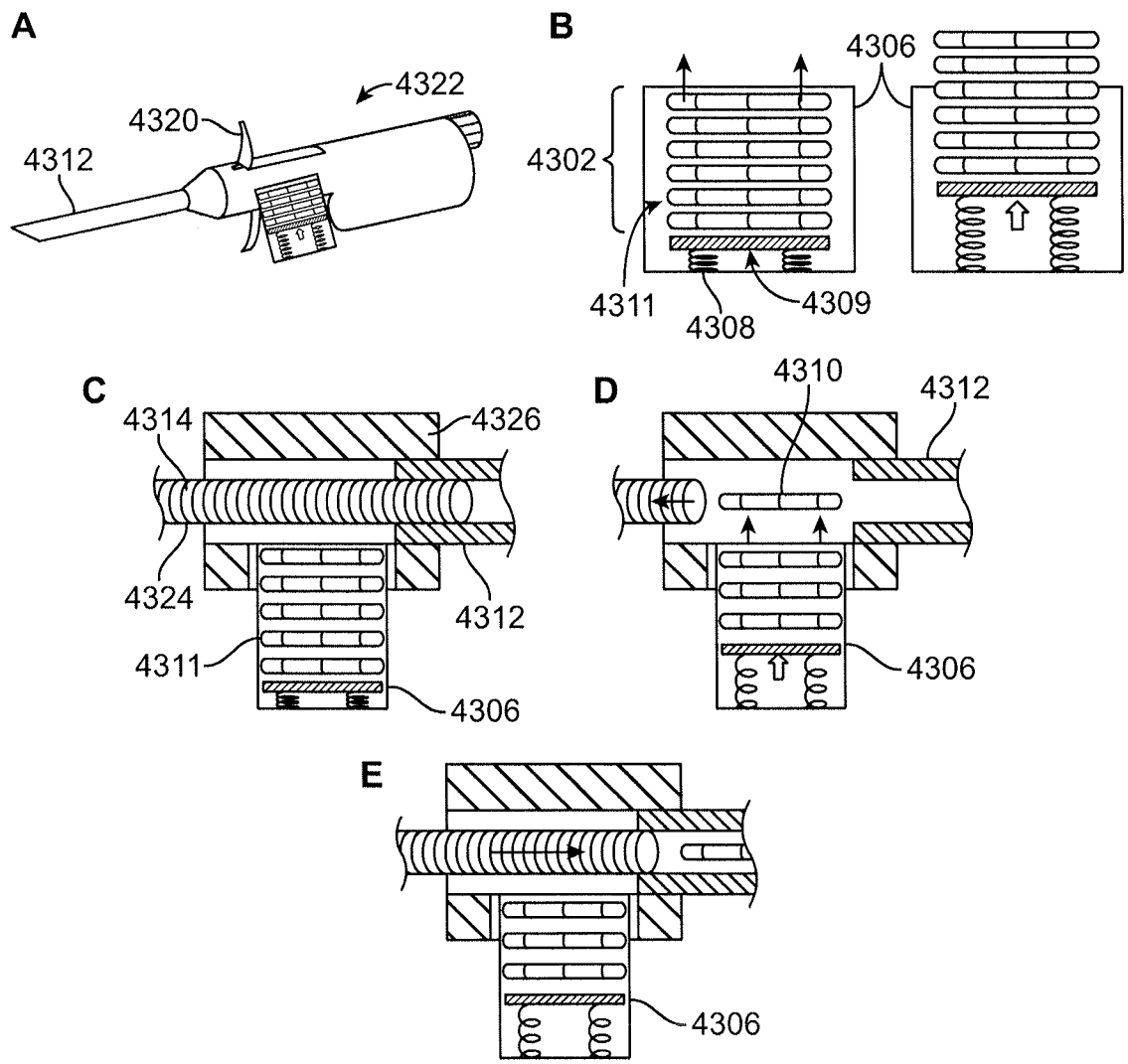
FIGS. 43A-43E show an embodiment of a delivery tool with a spring loaded clip for storing a multiple implants or a sheet of implants.
Figures 44A, 44B, 44C, 44D, 44E, 44F:
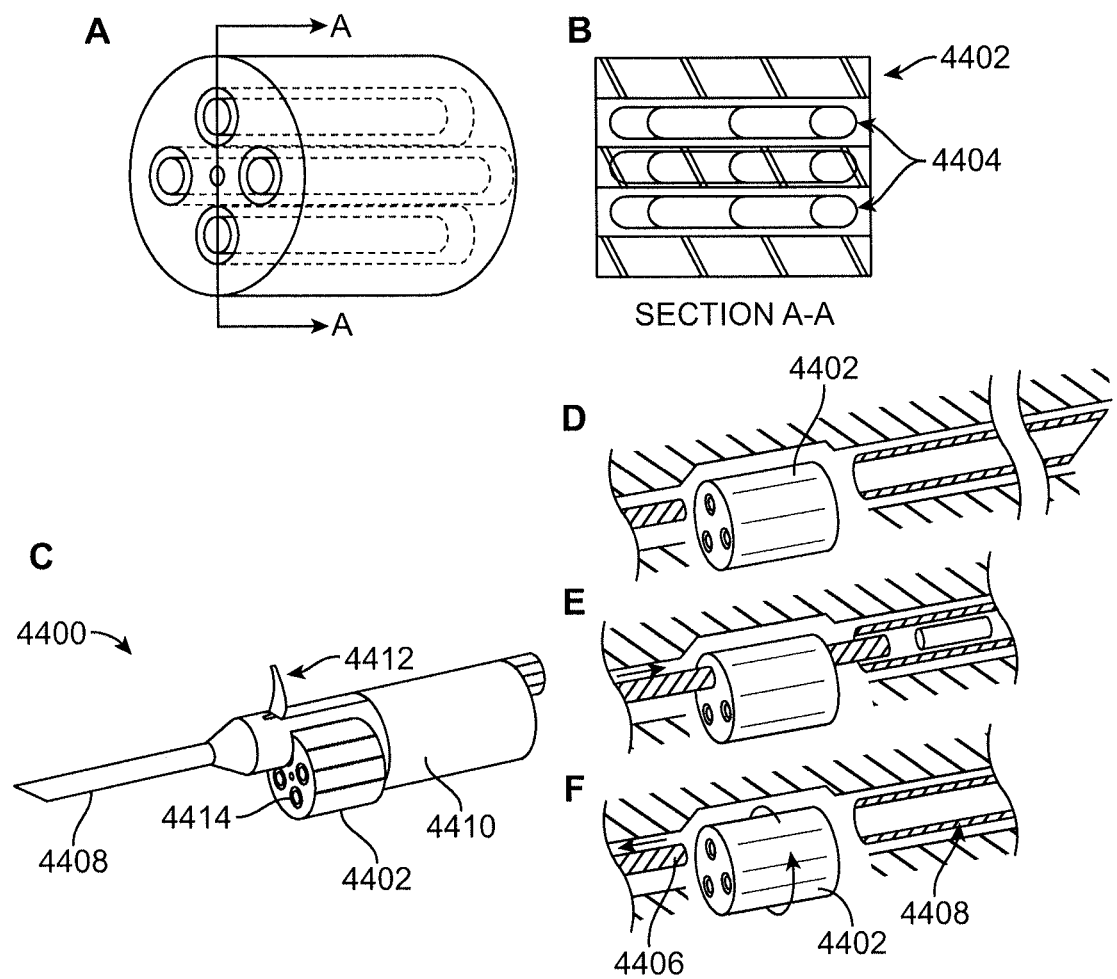
FIGS. 44A-44F show another embodiment of an implant delivery tool with a revolvable cylindrical housing for holding multiple implants.
Figures 45A, 45B, 45C, 45D:
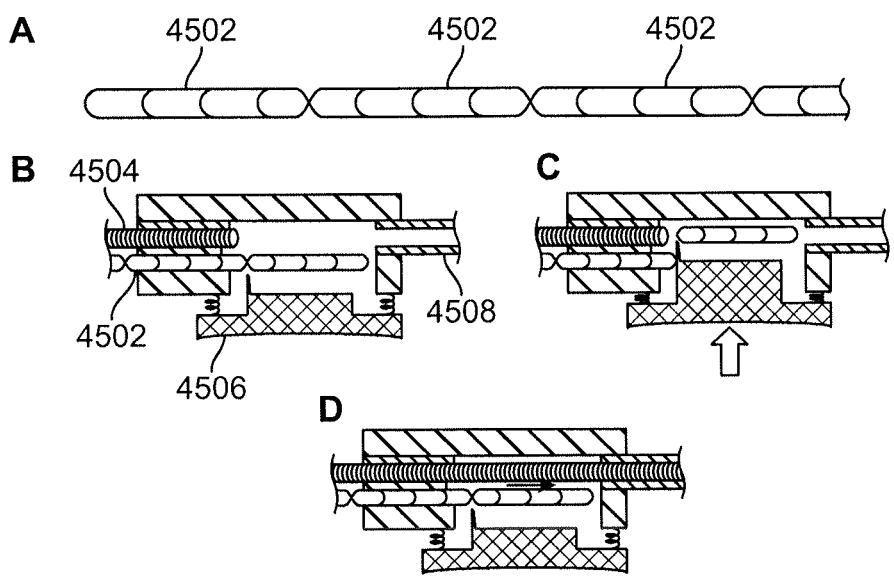
FIGS. 45A-45D show another embodiment of an implant delivery tool for holding multiple implants end-to-end.

In still another embodiment, illustrated in FIG. 42, the diameter of the cutting tool 4202 can be adjusted by, e.g., depressing a button 4204 on the tool body to apply a force to a cutting tool 4202 formed as a split cylinder. This feature enables the use of smaller implants introduced through smaller needles. Cutting tool 4202 has main tool body 4210. A sheet of implants 4208 is fed into the tool. Cutting tool 4202 also includes delivery needle 4206.

FIGS. 43A-43E illustrates a spring-loaded implant clip. In this embodiment, as in the embodiments above, a column of implants 4302 is loaded into the delivery tool through a window 4304. The sheet 4300 is loaded into a storage clip 4306. One or more springs 4308 and a lift platform 4309 on one side of storage clip 4306 pushes the sheet 4300 inward so that the innermost implant 4310 in the clip lines up with the bore of the introducer needle 4312. A pusher 4314 (with outer surface 4324) advances implant 4310 into needle 4312, as described above. The delivery tool body 4322 can be hand-held and controlled by trigger 4320.

Alternatively, a sheet of implants 4311, such as that described above with respect to FIGS. 38-42, can be loaded into the clip 4306. In this case, a shearing element, such as those discussed with respect to FIGS. 39-42, can be added to the assembly. The delivery tool body includes a handle distal core 4326.

FIGS. 44A-44F illustrates yet another way of loading multiple implants into a delivery tool. Delivery tool 4400 has a revolvable cylindrical housing 4402 having multiple implant chambers in which single implants 4414 are disposed. Housing 4402 is rotated to a position (possibly indicated with detents) in which an implant chamber lines up with the pusher 4406 and bore of needle 4408. The pusher 4406 then advances the implant 4404 into the needle as described above. The delivery tool may be hand-held by the main tool body 4410. Needle 4408 may be controlled by trigger 4412.

Figure 46A:
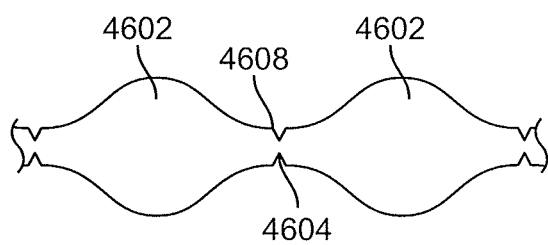
FIG. 46A is an end view of a sheet of nasal implants connected by bridges.
Figure 46B:
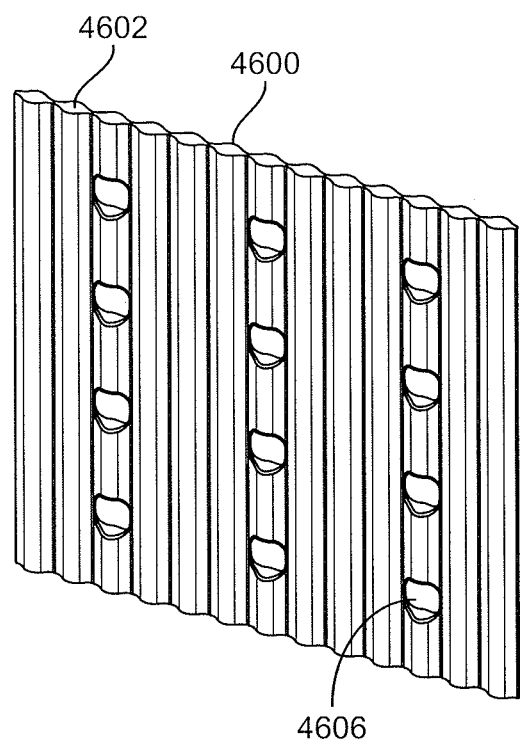
FIG. 46B is a perspective view of the sheet.

FIGS. 45A-45D illustrates still another embodiment in which multiple implants may be loaded into the delivery tool and delivered separately. In this embodiment, multiple implants 4502 are connected end to end and loaded into the delivery tool parallel to the pusher 4504. A cutting button 4506 in line with the distal-most implant segment in the line of implants can be depressed inwardly to cut one implant segment from the line and advance it into the delivery tool chamber in line with the pusher and the bore of the needle 4508. FIG. 46A is an end view and FIG. 46B is a perspective view of a sheet 4600 of nasal implants 4602 connected by bridges 4604. Through holes 4606 are dimensioned to replicate Lactosorb® sheets (~2 mm) to allow suturing. Slots 4608 provide cut guides for separating individual implants.

Figure 47A:
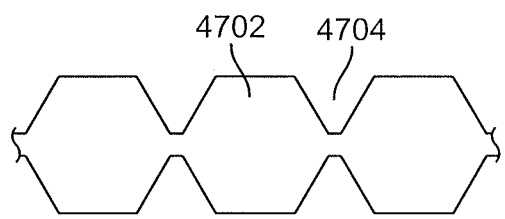
FIG. 47A is an end view of another sheet of nasal implants connected by bridges.
Figure 47B:
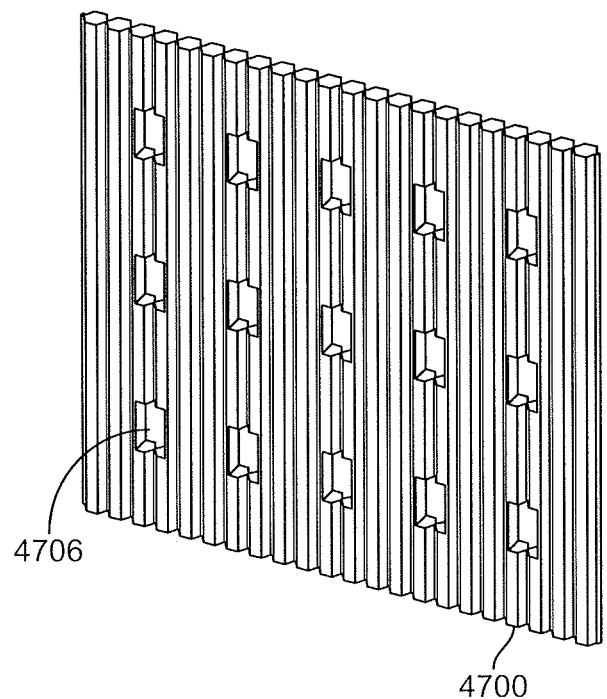
FIG. 47B is a perspective view of the sheet.

FIG. 47A is an end view and FIG. 47B is a perspective view of a sheet 4700 of nasal implants 4702 connected by bridges 4704. Through holes 4706 are dimensioned to replicate Lactosorb® sheets (~2 mm) to allow suturing. The bridge sections are designed to break without the need to cut with a scalpel.

Figure 48A:
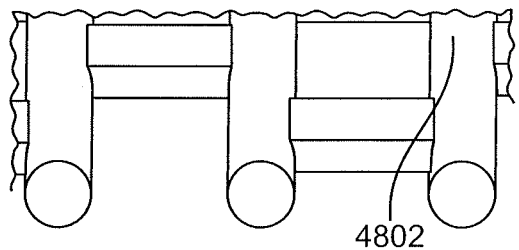
Figure 48B:
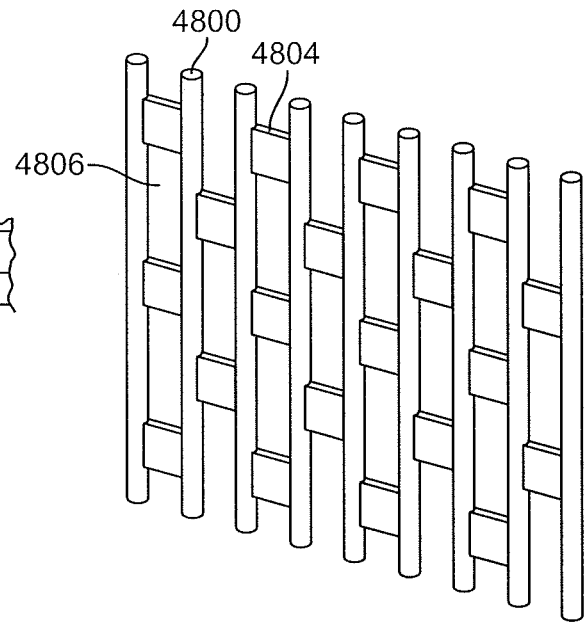
FIG. 48B is a perspective view of the sheet.

FIGS. 48A and 48B show a sheet 4800 of individual nasal implants 4802 connected by bridges 4804. The openings 4806 in the sheet are larger than in the embodiments of FIGS. 46 and 47 to allow for a needle and suture to pass through.

Figure 49A:
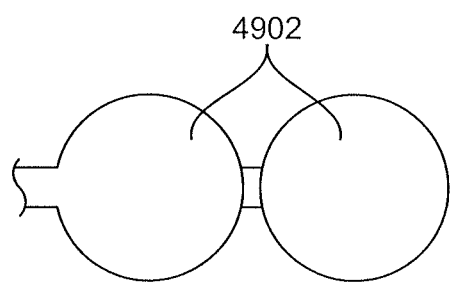
FIG. 49A is a partial end view of another sheet of nasal implants separated by a large sheet section with holes.
Figure 49B:
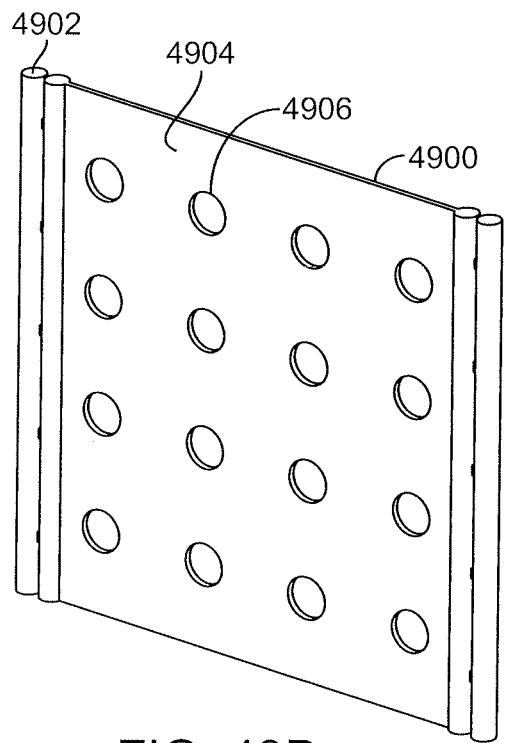
FIG. 49B is a perspective view of the sheets.

FIG. 49A is a partial end view and FIG. 49B is a perspective view of a sheet 4900 of nasal implants 4902 separated by a large sheet section 4904 having holes 4906 formed therein.

Figure 50A:
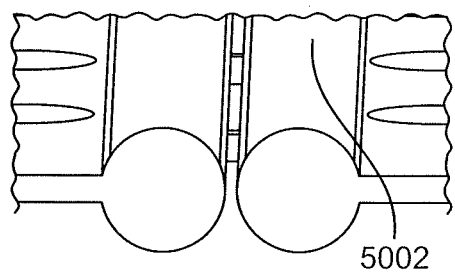
FIG. 50A is a partial end view of another sheet of nasal implants aligned in pairs.
Figure 50B:
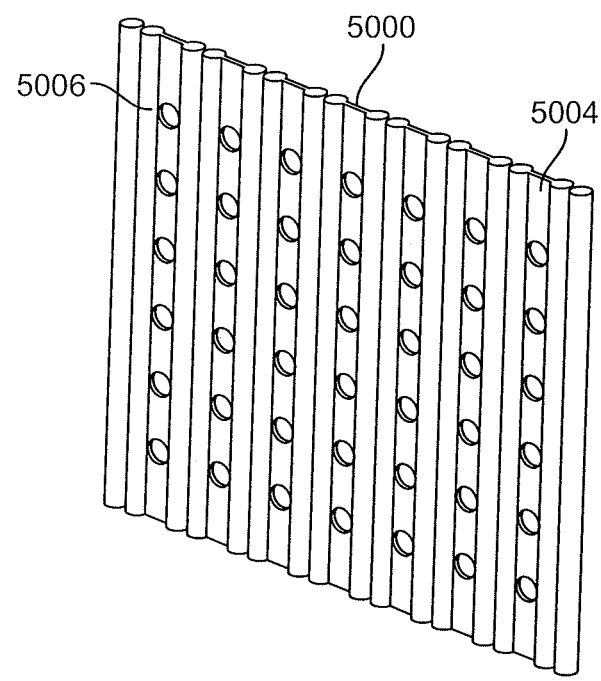
FIG. 50B is a perspective view of the sheet.

FIG. 50A is a partial end view and FIG. 50B is a perspective view of a sheet 5000 of nasal implants 5002 aligned in pairs. Holes 5006 are formed in bridge sections 5004 between pairs of implants.

Figure 51A:
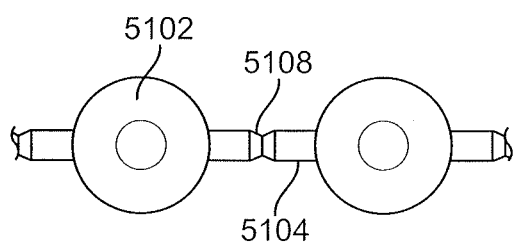
FIG. 51A is a partial end view of another sheet of nasal implants having rounded ends and connected by bridges with openings.
Figure 51B:
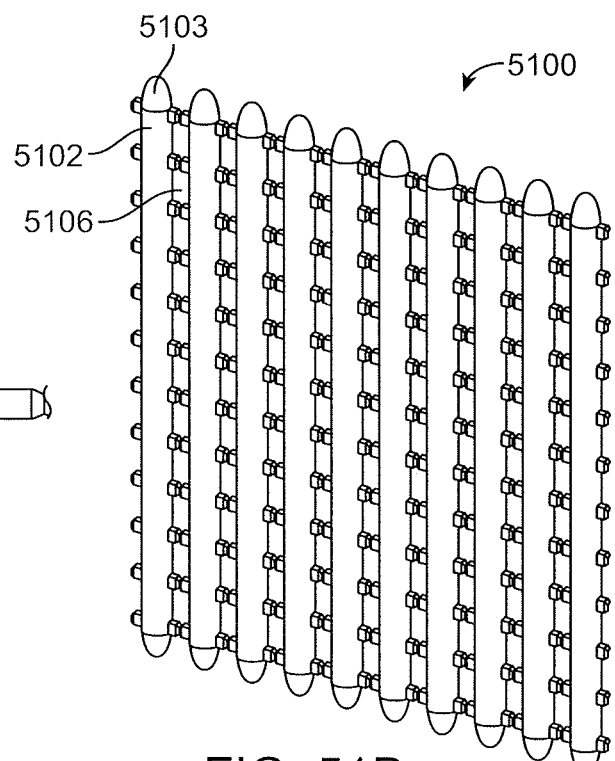
FIG. 51B shows a perspective view of the sheet.

FIG. 51A is a partial end view and FIG. 51B is a perspective view of a sheet 5100 of nasal implants 5102 having rounded ends 5103. The implants are connected by bridges 5104 having openings 5106 between them. Cutting guide slots 5108 may be formed in the bridges.

FIGS. 52A-52H show details of a sheet 5200 of nasal implants 5202 connected by bridges 5204.

EXAMPLES

Example 1

Material samples testing Table 1 shows material property test results of candidate implants made into various shapes and sizes with the indicated inner diameter (ID) and outer diameter OD) from the indicated materials. The modulus of elasticity (E), cross-sectional inertia of the sample (I), and flexural rigidity (E•I) which represents the strength of the sample when bending, are indicated. The PLLA and PLLA-PGA samples were flexurally stronger than the other samples, presumably due to the strength of the PLLA and the rod shape of the PLLA-PGA sample. The PLLA-PDLA sample was weak in bending, presumably due to its thin-wall, tube shape. The PLLA-PCL sample was very flexible, presumably because it was in a glassy stage as its glass transition temperature is below room temperature; overall it did not behave like a typical solid material.

Example 2 Table 2 Shows Moldability with Temperature and Brittleness

Testing performed on the material samples. Samples were cut to 15 mm length. Samples were tested at room temperature and heated to several temperatures in an oven and left to sit to ensure the materials were a consistent temperature throughout the sample. Each sample was tested by removing it from the oven and immediately bending it by hand to 90 degrees (if possible). Observations of how much force was required, whether the material held the shape, cool off time, and material brittleness were recorded and summarized.

Example 3

Figure 53A:
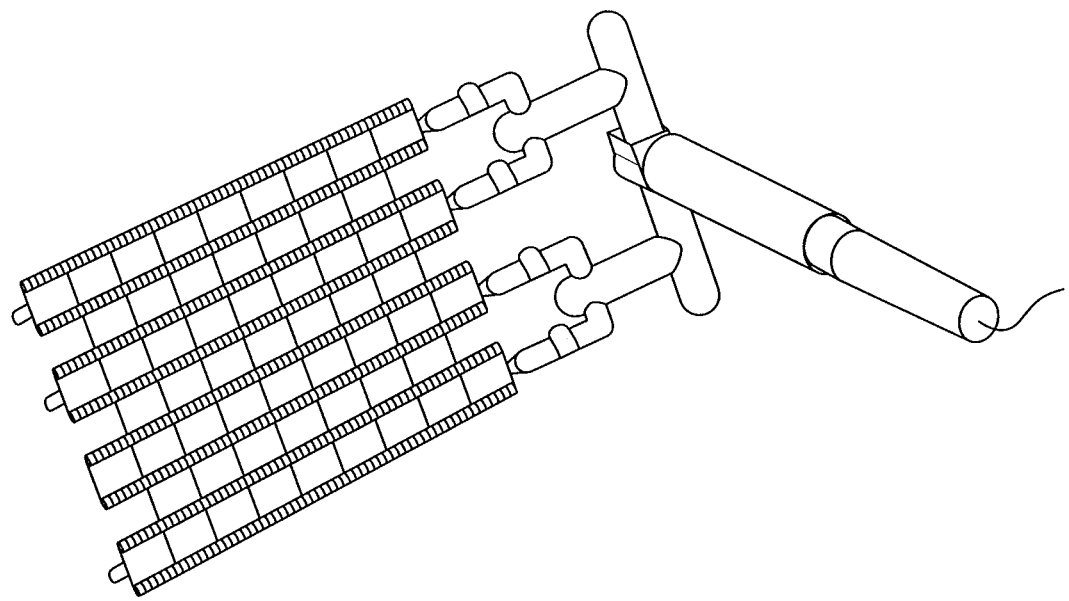
FIGS. 53A and 53B show an implantable sheet being cut.
Figure 53B:
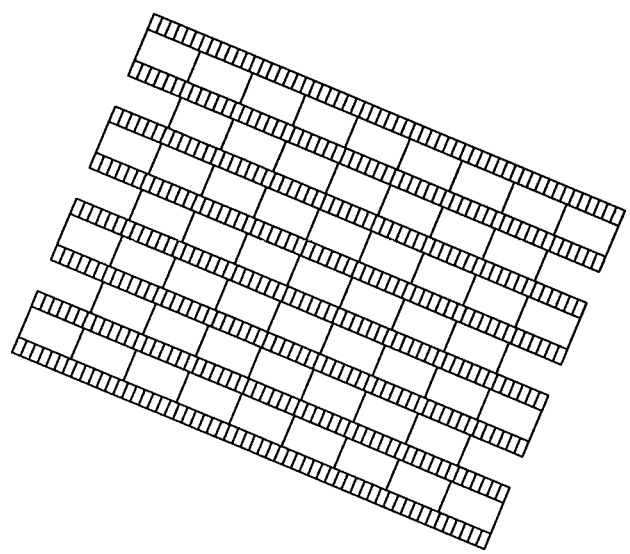

An implantable sheet was cut and tested for fitting into a 16 gauge syringe. Samples fit through. When a scalpel is place accurately through the bridge trough, the sheet could be cut relatively easily. FIG. 53A and FIG. 53B show results from cutting an implantable sheet.

Example 4 Implant-Dimension Protocol

| Results | Test Methodology |
|---|---|
| 20.09 mm | Measured using Micro-Vu Vision System |
| 24.73 mm | Measured using Micro-Vu Vision System |
| 0.00 mm 0 degrees | Measured height of the implant on both ends |
| Average width (mm): 1.92 | Measured and average 4 void from the sheets |
| Average length (mm): 2.38 | |
| Rod average length (mm): 1.26 | Measured and averaged four bridge lengths using Micro-Vu vision system |
| Bridge average length (mm): 2.93 | |
| Rod groove width (mm): 0.45 | Measured and averaged four bridge widths using Micro-Vu vision system |
| Bridge average width (mm): 1.93 | |

Example 5 Implant Flexural Rigidity Protocol

Two implant rods were soaked in water heated to 37 degrees C. for 1 hour. They were then flexed from 180 degrees to 7 mm. The samples had a flexural rigidity of 114 N-mm$^2$ and 105 N-mm$^2$. Results are shown in FIGS. 54A-54C.

Example 6 Implant Migration Protocol

Implant is inserted into tissue sample using cannula. Implant is placed into test fixture and run for 1000 cycles. Implant location compared before and after. Result was less than 0.5 mm vertical and horizontal travel for all tests. The implant migration after manually flexing tissue for 5 minutes. FIGS. 55A-55B show results from a 1000 cycle test using a test fixture. In another case, implant migration was tested after manually flexing tissue for 5 minutes. None to minor migration was observed. Results are shown in FIGS. 56A-56B.

Figure 59A:
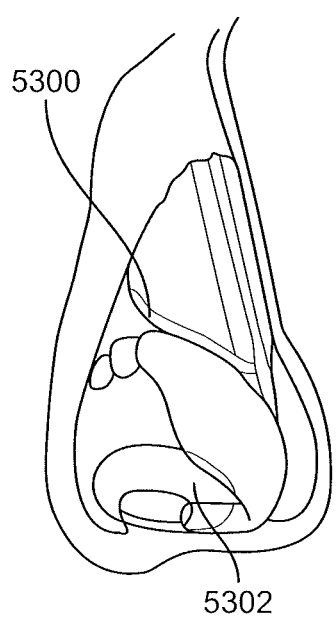
FIGS. 59A and 59B show different views of the anatomy of the nose including the external nasal valve and internal nasal valve.
Figure 59B:
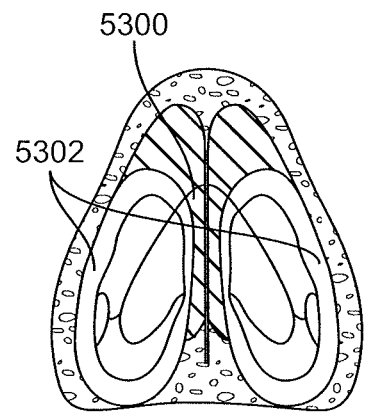
Figure 60A:
FIGS. 60A and 60B show a collapsed nasal valve upon inhalation.
Figure 60B:

Various regions of airway tissue can impact airflow to the lungs. One major impact on airflow is from airflow resistance from the nose. The highest resistance structures in the nose may be the narrowest regions, such as the external nasal valve 5302 and the internal nasal valve 5300, shown in FIGS. 59A-59B. During normal inspiration, nasal valve cartilage around these valves prevents or reduces valve collapse and helps maintains airway patency. Incompetent internal valves and/or external valves can collapse and obstruct airflow during inhalation, as shown in FIGS. 60A-60B. FIG. 60A shows a valve at rest and FIG. 60B shows valve collapse upon inhalation. Problems with the nasal septum, nasal turbinates, lateral cartilage, or other structures due to, for example, aging, poorly formed or weak cartilage, surgery (e.g., rhinoplasty, septoplasty) and/or trauma can lead to nasal valve problems and impact airflow such as difficult breathing, snoring, sleep apnea and reduction in quality of life. Provided herein are less-invasive surgical treatments for nasal valve collapse. Such treatments may be effective, minimally invasive, outpatient treatments and may result in reduced pain and a rapid recovery, and may be a lasting solution.

Surgical treatments (e.g., submucosal resection of turbinates, septoplasty) have been used in the past to reduce the size of the turbinates or correct deviated septum or to repair the nasal wall in order to improve the nasal valves and airflow. These surgical treatments are invasive, uncomfortable and require significant time to recuperate. Furthermore, they do not readily address problems with the lateral cartilage wall. The lateral cartilage wall has been repaired, for example, by cartilaginous graft techniques using additional material (cartilage) from the nose or ear. In addition to the above mentioned limitations, these techniques are expensive (e.g. thousands of dollars), highly invasive, require a high level of surgical experience, have long, painful recovery times (e.g. 3 weeks of downtime), do not always work well and require a second surgical invasion site (into the nasal area or ear to obtain cartilage). Invasive nasal surgery is complicated by the ongoing need to use the surgical site for breathing. Thus, invasive surgical approaches are far from ideal. Non-surgical approaches for nasal valve collapse include strips or stent-like materials (e.g., "BreathRight", Breathe with EEZ, Nozovent") that are placed on or around the nose. These temporary, suboptimal approaches suffer from limited efficacy and poor cosmesis.

Provided herein are implants, assemblies, systems, and methods for improving and repairing a nasal valve. Such valve repair materials and methods may be used in minimally invasive procedures, outpatient procedures and may result in minimal pain and rapid recovery, especially compared with previous surgical interventions.

Figure 61A:
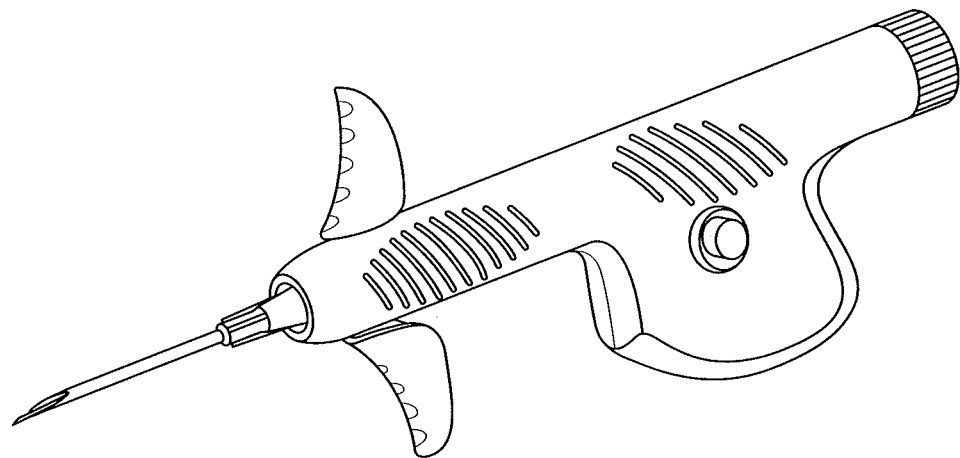
FIGS. 61A-61D show a delivery system with different views of a delivery tool (FIGS. 60A and 60B) and implants (FIGS. 60C and 60D) that may be delivered using the delivery tool.
Figure 61B:
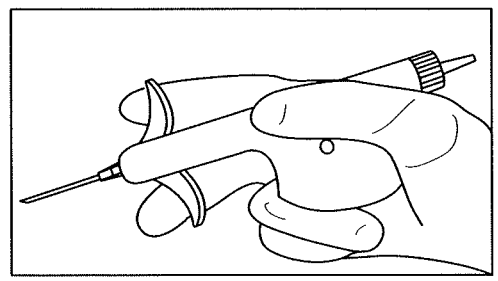
Figure 61C:
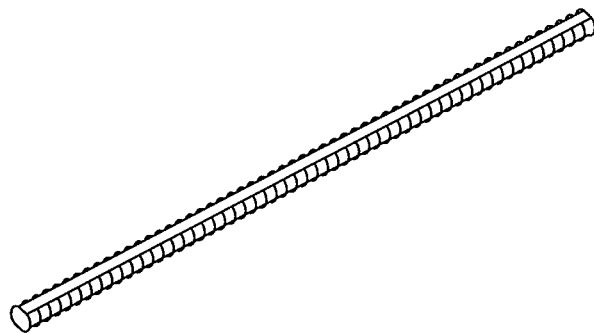
Figure 61D:
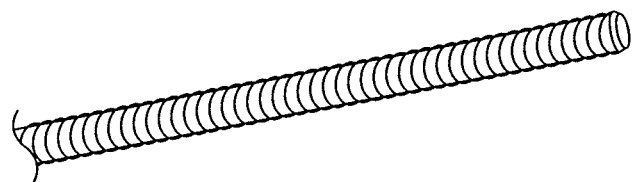

Another aspect of the invention provides a delivery system such as shown in FIGS. 61A-61D including a delivery assembly with a delivery tool (FIG. 61A) and one or multiple nasal implants (FIGS. 61C-61D).

In some embodiments, an implant may comprise an absorbable, biocompatible polymer or copolymer such as known in the art (e.g. poly-L-lactic acid (PLLA), poly(D-lactic acid (PDLA) etc.). In a particular embodiment, a copolymer may include both PLA and PDLA, such as in a 70:30 PLLA/PDLA ratio. An implant may have favorable stress/strain mechanics.

An implant may be sized by a physician. An implant may comprise a polymer configured to absorb quickly or more slowly when in position in a nasal tissue. An implant may be configured to remain substantially intact for at least 3 months, at least 6 months, at least 9 months, or at least 12 months. An implant may be configured to be substantially completely resorbed in 18 months.

An implant may be chosen to have tough but favorable stress/strain mechanics. An implant may have a strength similar to a cartilage strength. An implant may be shapeable without fracturing. An implant may a flexure similar to a flexure of cartilage. An implant may be configured to have a flexural rigidity stronger than cartilage when in place in a nasal tissue for longer than 6 months.

An implant may be any size that provides a therapeutic or cosmetic benefit and/or facilitates implantation or bioabsorption. An implant may be sized to fit into a needle, such as an off-the-shelf needle (e.g. larger than 10 gauge, 10, 11, 12, 13, 14, 15, 16, 17, 18, 19, 20, 21, 22, 23, 24, 25, 26, 27, 28, 29, 30, 31, or 32 gauge, or smaller than 32 gauge). An implant may be held in a needle by any means, such as a tight (friction fit), a tab, a mating mechanism, etc. An implant may have features (e.g. ridges, bumps, etc.) and may contact an internal surface of a needle when in place in a delivery assembly.

An implant may be any shape that provides a therapeutic or cosmetic benefit and/or facilitates implantation or bioabsorption. An implant may have one or more substantially flat side(s) and ribs that allow for a maximized rod diameter and rib height without excessive friction when in place in a needle. A ribbed configuration may eliminate implant migration.

Another aspect of the invention provides a plurality of interconnected implants such as shown in FIGS. 62A-62D. FIGS. 62A-62B show rod implants and FIG. 62C shows a detail view of the section "A" indicated in FIG. 62B. Two or more than two implants may be formed as a long structure. Two or more than two implants may be molded together, such as injection molded in a perforated sheet. Implants may be separated, such as with a cutting instrument. An implant, such as those shown in FIGS. 62A-62D may have an anti-migration feature. For example, an implant with an anti-migration feature may have an increase (e.g., 5X) in acute longitudinal stability relative to a smooth implant. An implant with an anti-migration feature may be easier to injection mold. Such an implant may have predictable degradation. An implant may represent nasal cartilage mechanics. An implant may have a flexural rigidity value stronger than cartilage for a time period (e.g., 6 months) after being implanted. An implant may be shapeable without fracturing. An implant may have an average acute flexibility similar to reconstruction plate products. An implant may have flat sides to allow for maximized rod diameter and rib height without excessive friction in needle bore.

Another aspect of the invention provides a delivery tool assembly configured to delivery an implant into a nasal tissue. A delivery tool assembly may include a needle configured to house an implant and a stylus configured to push an implant out of the needle and into nasal tissue during implant delivery (such as to a nasal valve region).

A delivery tool assembly may include an implant positioning knob configured to move an implant to a desired (distal) staging area. A distal staging area may be near or at a tip of a needle.

A delivery tool assembly may include a trigger lock mechanism to prevent undesired needle movement.

A needle of a delivery tool assembly may be configured to pierce a nasal mucosa and position an implant in a desired location in a nasal tissue. An implant may be configured to be pushed out of a needle at the same time that a needle is removed from the tissue. In some cases, simultaneous pushing of an implant from a needle and removal of a needle from nasal tissue may result in undesired implant movement or implant repositioning.

Figure 63A:
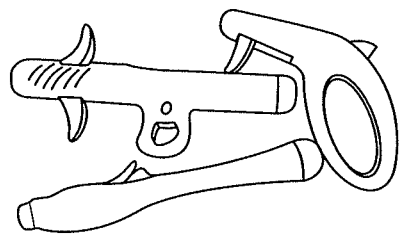
Figure 63B:
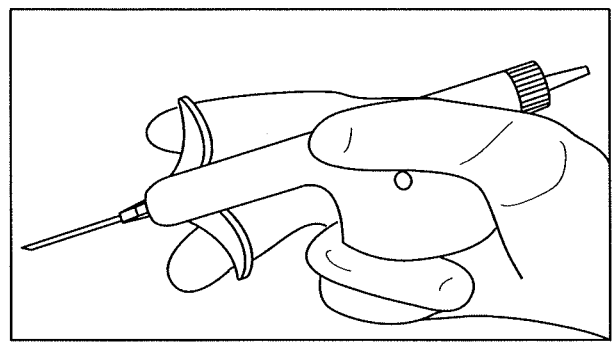
Figure 63C:
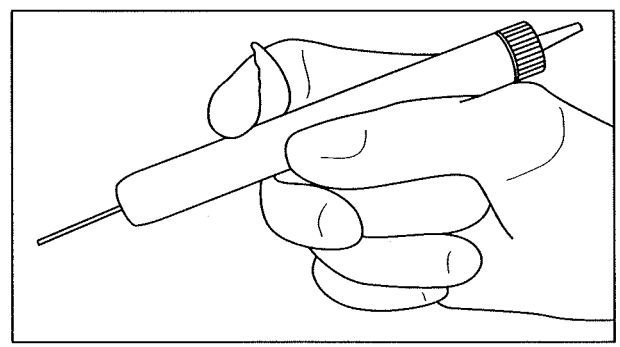
FIG. 63C shows a detail view of the section indicated by "A" in FIG. 62B.

In some embodiments, a delivery tool may be configured to be held in a hand (e.g. may have an ergonomic design) as shown in FIGS. 63A-63C. A delivery device may be designed to pierce mucosa and position an implant in a desired position.

Figure 64A:
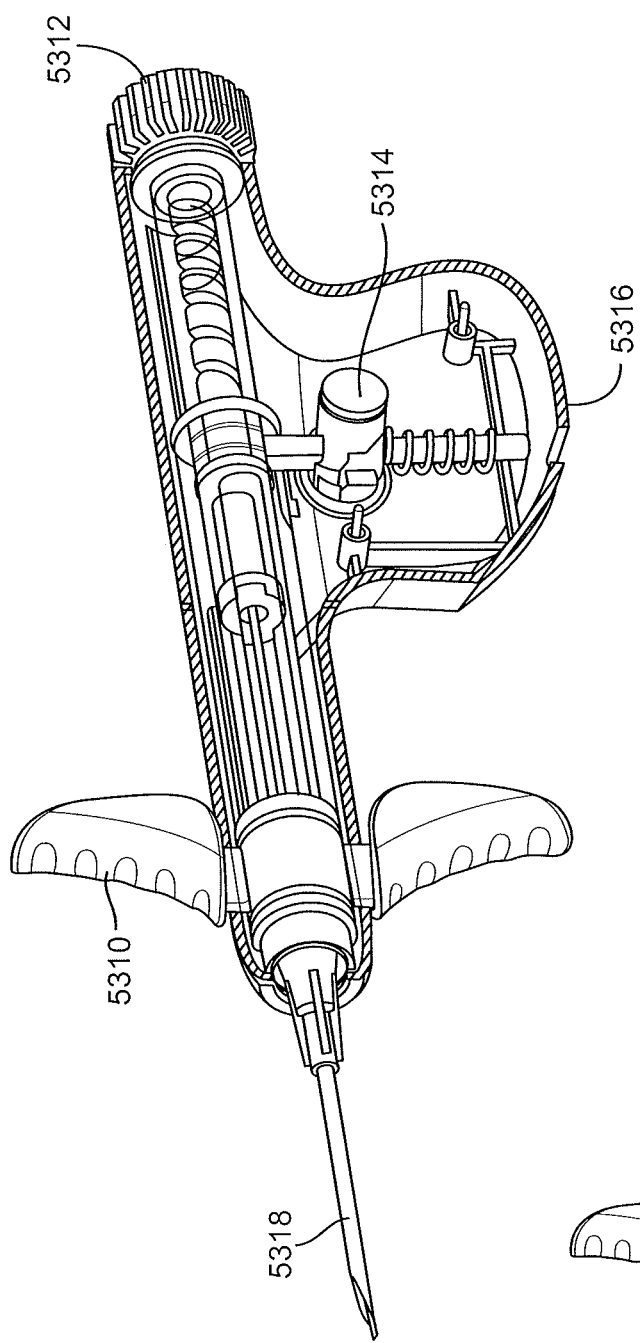
FIGS. 64A and 64B show a delivery tool with the needle advance (FIG. 64A) and retracted (FIG. 64B) according to one aspect of the invention.
Figure 64B:
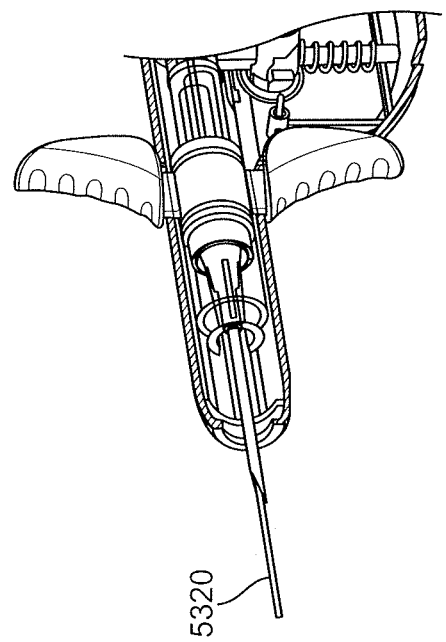

In some embodiments, a delivery tool may have a needle advance position (FIG. 64A) and a needle retracted position (FIG. 64B). A delivery tool may have a body, a grip (e.g. a half-grip 5316), a trigger, a trigger lock 5314, a needle 5318, an implant positioning knob 5312, and an implant plunger 5320 or stylus such as shown in FIGS. 64A-64B. An over-under trigger 5310 mechanism configured to provide axial stability during needle placement, implant placement, and/or needle retraction. The implant positioning knob 5312 advances the implant to the distal staging area at the needle tip. The needle (e.g., a 16 gauge hypodermic needle) may make a small entry site with minimal tissue dissection and pain. The implant plunger 5320 injects the implant. It may have a front-end "bone prep" feature (e.g., a drill bit). A trigger lock 5314 may provide safety during needle placement. A half-grip may maintain a low profile grip arm.

A delivery tool assembly may comprise multiple implants. Multiple implants may be loaded at one time. Alternatively, an implant may be loaded, implanted, and the delivery tool assembly reloaded with another implant for delivery.

A delivery tool assembly may include a bone prep feature (e.g. a drill bit).

Tactile clues may be used for placing an implant in a nasal tissue. One such tactile clue may include palpating a nasal region (e.g. palpating an implant or a needle from an outside surface of the nose). Another such tactile clue may include sensing a resistance from a delivery tool assembly in place in a nasal tissue wherein the resistance is indicative of the delivery tool assembly contacting a bone.

One method of placing an implant in a nasal valve includes the steps of placing a delivery tool assembly in contact with a nasal tissue, the delivery tool assembly comprising a needle housing an implant, advancing the needle and implant into a nasal tissue until the needle contacts a bone, releasing a needle safety lock on the delivery tool assembly, and unsheathing the implant by retracting the needle proximally to thereby place the implant adjacent the bone. For example, the implant remains in a desired position while the needle is retracted away from the implant.

In some embodiments, an implant is placed in a nasal tissue such that most or all of the implant is surrounded by nasal tissue and/or tissue overlying the maxilla. Nasal tissue may form a support, such as a tight support, around the implant.

Figure 65:
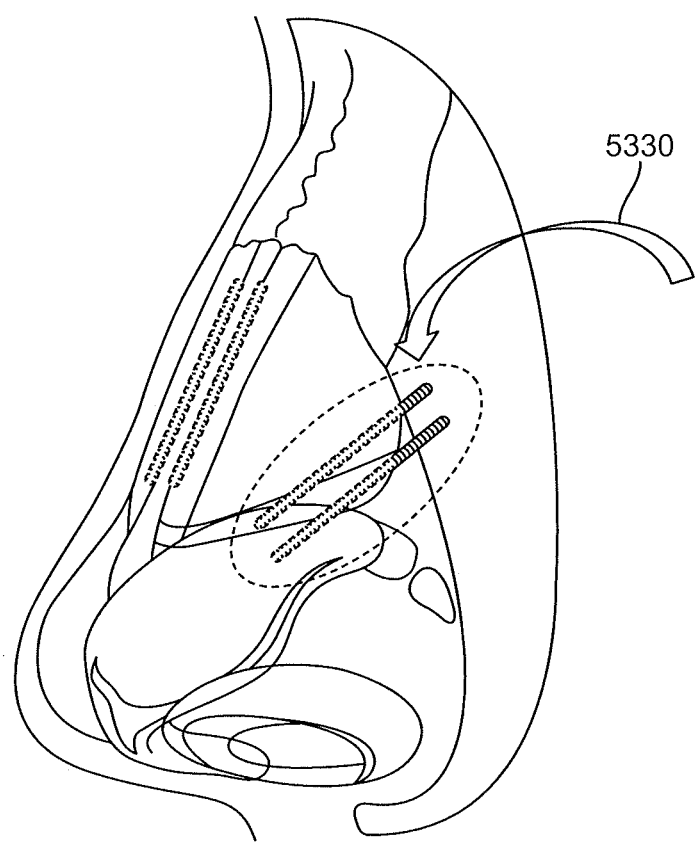
FIG. 65 shows examples of nasal implants implanted in nasal tissue according to one aspect of the invention.

FIG. 65 shows implants 5330 placed in a lateral wall of a nasal valve, such as to strengthen the valve. One, two, or more than two implants may be placed. The implants may be parallel to each other or may be obliquely oriented relative to one another. An implant may be placed to endonasally pierce through mucosa, may be lateral to mucosa, medial to lateral cartilage and/or superficial to the maxilla.

Figure 66A:
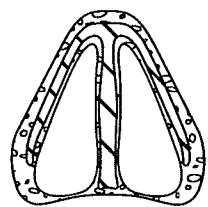
FIGS. 66A-66C show examples of nasal implants implanted in nasal tissue according to one aspect of the invention.
Figure 66C:
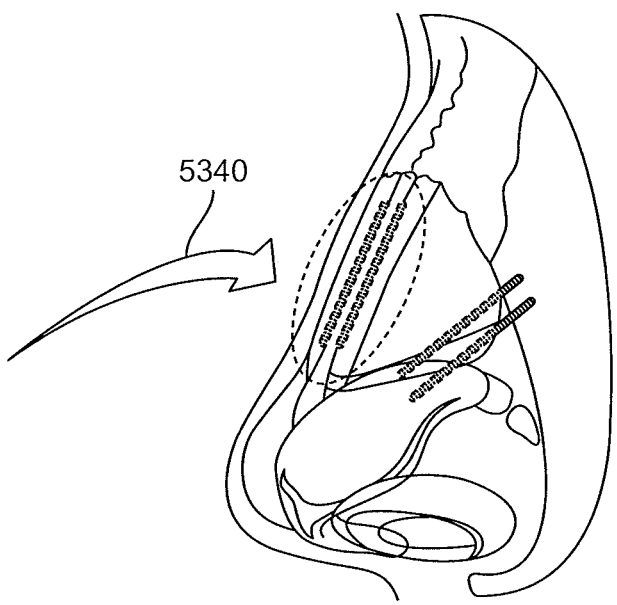
Figure 66B:
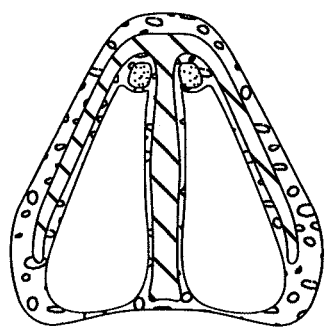

FIGS. 66A-66C show implants 5340 placed in a "spreader" region, such as along a superior aspect of the nose. Such an implant may endonasally pierce through mucosa, wedge between the lateral cartilage and the septum, and/or increase an internal nasal angle.

Figure 67C:
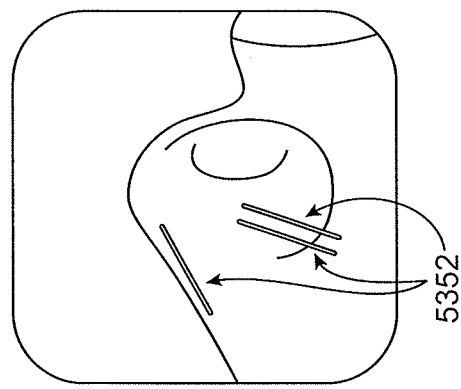
FIGS. 67A-67C show an embodiment of a method for placing one or more implants in nasal tissue.
Figure 67B:
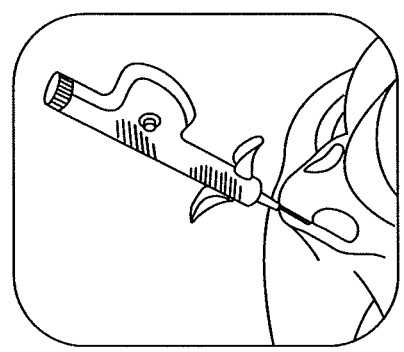
Figure 67A:
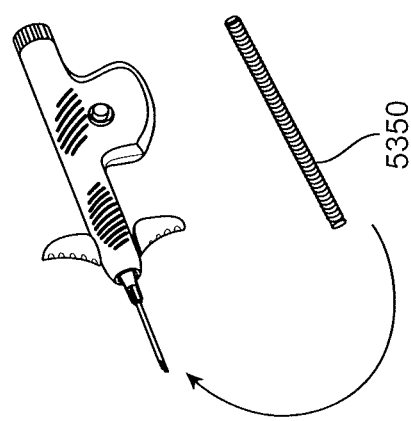

FIGS. 67A-67C show one embodiment of a method for placing one or more implants in nasal tissue. Any number of implants may be placed and in any orientation. Implants may be placed almost parallel to a bottom plane of the nose (e.g. as shown in FIG. 67C). Implants may be oblique relative to a bottom plane of the nose. For example, an implant may form a line from a tip of the nose to a corner of the eye. In some embodiments, an implant 5350 may be sized by a physician to an appropriate length and inserted into a delivery device as shown in FIG. 67A. As shown in FIG. 67B, the delivery device is inserted below lateral cartilage and advanced to the maxilla bone. An implant is pushed out of the delivery device, creating a support beam between lateral cartilage and maxilla. A plurality of implants 5352 may be placed. As shown in FIG. 67C, the delivery device is removed, leaving the implant as a support beam to prevent nasal valve collapse.

Figure 68A:
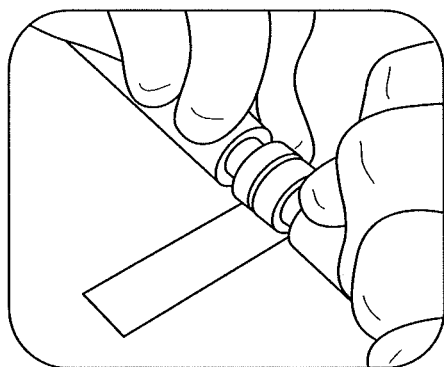
FIGS. 68A-68D show steps in preparing an implanting an implant in a nose.
Figure 68B:
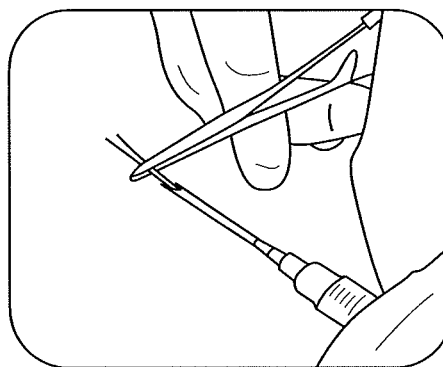
Figure 68C:
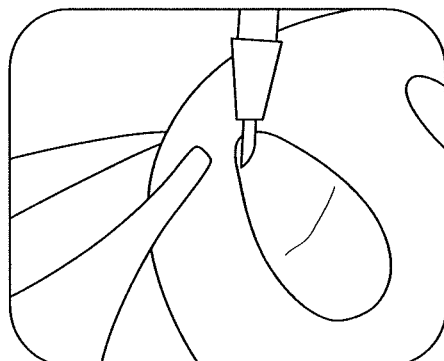
Figure 68D:
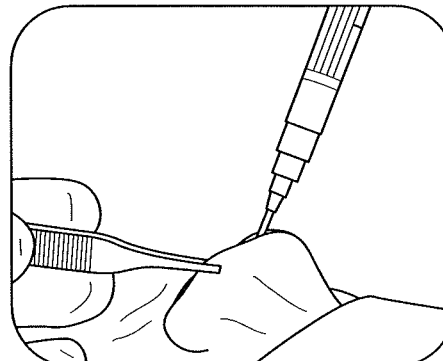

FIGS. 68A-68D show steps in preparing and implanting an implant in a nose. FIG. 68A shows forming an implant. FIG. 68B shows implant delivery preparation. FIGS. 68C-68D show, respectively, internal and external views of implant delivery.

Figure 69:
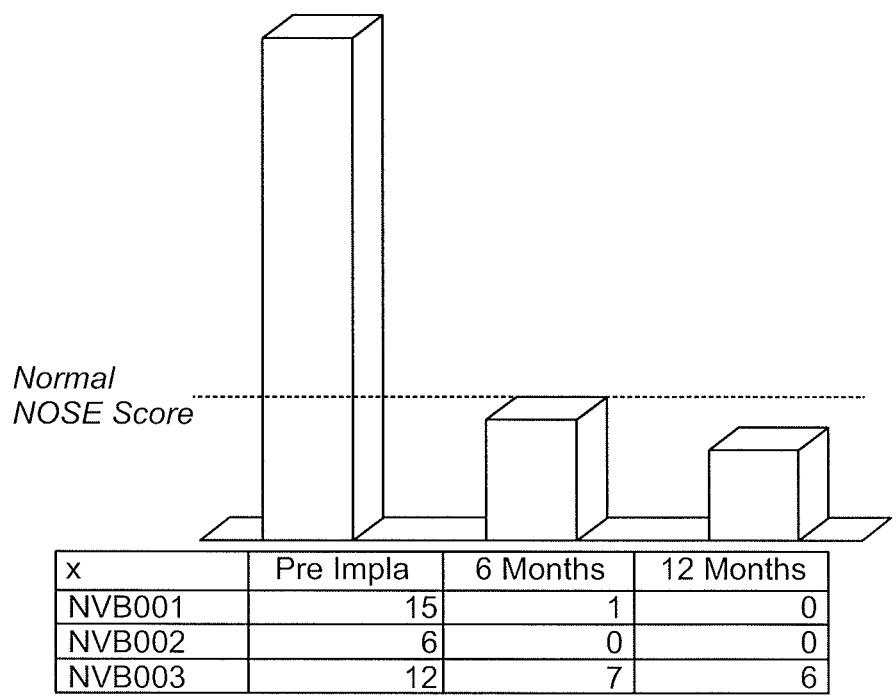
FIG. 69 shows subjective interpretation of nasal obstruction symptoms after implanting implants in a pilot study after 6 months and 12 months, compared with pre-implantation symptoms.

FIG. 69 shows subjective interpretation of nasal obstruction symptoms after implanting implants in a pilot study after 6 months and 12 months, compared with pre-implantation symptoms using a validated NOSE (Nasal Obstruction Symptom Evaluation) scale. Nasal obstruction was reduced.

What is claimed is:

1. A method of implanting an implant into a nasal tissue of a patient, the implant comprising a first end including a resiliently deformable portion configured to have a contracted first shape with a non-circular cross-section and an expanded second shape, the method comprising:
providing the implant in the contracted first shape close to a distal end of a delivery conduit of a housing, the delivery conduit comprising an interior orienting portion with a cross-sectional shape configured to orient the implant relative to the delivery conduit, wherein the implant comprises a rod-shaped implant and the resiliently deformable portion comprises a plurality of tines connected to and extending from the rod-shaped implant;
piercing a nasal tissue with a piercing end of the delivery conduit by moving the delivery conduit through the nasal tissue;
advancing the implant out of the delivery conduit and/or retracting the delivery conduit to thereby expand the implant to the expanded second shape and to leave the implant in place in the nasal tissue, wherein the expanded second shape of the resiliently deformable portion corresponds to an orientation of the implant within the delivery conduit orientating portion; and
removing the delivery conduit from the patient.

2. The method of claim 1, wherein the resiliently deformable portion comprises two tines.

3. The method of claim 2, wherein the resiliently deformable portion comprising the two tines and a remainder of the implant comprise a same material.

4. The method of claim 1, further comprising: holding the implant near the distal end of the delivery conduit when the implant is in the delivery conduit.

5. The method of claim 4, further comprising: providing a friction fit between the implant and the delivery conduit to hold the implant in the delivery conduit.

6. The method of claim 1, wherein the delivery conduit comprises a needle selected from a group consisting of a 14 gauge, a 16 gauge, or an 18 gauge needle and the implant is configured to sit in the needle.

7. The method of claim 1, further comprising: placing the implant into the delivery conduit through a window along a length of a delivery tool, the window configured to accept the implant into the delivery conduit.

8. The method of claim 1, wherein the cross-sectional shape of the delivery conduit comprises an ellipse.

9. The method of claim 1, wherein a length of the implant comprises a plurality of repeating features.

10. The method of claim 1, wherein the implant comprises a plurality of ribs with alternating raised regions and depressed regions.

11. The method of claim 1, wherein the implant comprises a first end feature and a second end feature different from the first end feature.

12. The method of claim 11, wherein the first end feature comprises a rounded end.

13. The method of claim 1, wherein the implant comprises a biodegradable material.

14. The method of claim 1, wherein the implant comprises a biocompatible, biodegradable poly-L-lactic acid (PLLA) or poly-D-lactic acid (PDLA).

15. The method of claim 1, wherein the implant is configured to provide an implant flexural rigidity between $2.5e^{-6}$ N-m$^2$ and $1.5e^{-5}$ N-m$^2$.

16. The method of claim 1, further comprising advancing a stylet within the delivery conduit to move the implant distally within the delivery conduit.

17. The method of claim 1, wherein the first end of the implant is a distal end of the implant.

18. The method of claim 1, further comprising: engaging the implant with lateral cartilage.

19. The method of claim 1, further comprising: engaging the implant with septal cartilage.

20. The method of claim 1, further comprising:
releasing a user-controlled safety mechanism to thereby allow movement of the implant;
and advancing the implant further to the distal end of the delivery conduit; and
advancing the implant out of the delivery conduit and/or retracting the delivery conduit by actuation of an actuation mechanism.

21. The method of claim 1, further comprising: anchoring the implant to the nasal tissue when the implant is in place in the nasal tissue.

22. The method of claim 1, further comprising: supporting the nasal tissue with the implant.

23. The method of claim 1, wherein advancing the implant out of the delivery conduit and/or retracting the delivery conduit includes pushing the implant out of the delivery conduit.

24. The method of claim 1, further comprising: loading the implant into the housing.

25. The method of claim 1, further comprising: loading the implant into the delivery conduit such that the implant is in the contracted first shape.

26. The method of claim 1, further comprising: advancing the implant through the delivery conduit until the implant is close to the distal end of the delivery conduit.

27. The method of claim 1, wherein the resiliently deformable portion and a remainder of the implant comprise a same material.

28. The method of claim 10, wherein the plurality of ribs are circumferential ribs.

29. A method of implanting an implant into a nasal tissue of a patient, the implant comprising a first end including a resiliently deformable portion configured to have a contracted first shape with a non-circular cross-section and an expanded second shape, the method comprising:
providing the implant in the contracted first shape close to a distal end of a delivery conduit of a housing, the delivery conduit comprising an interior orienting portion with a cross-sectional shape configured to orient the implant relative to the delivery conduit;
piercing a nasal tissue with a piercing end of the delivery conduit by moving the delivery conduit through the nasal tissue;
advancing the implant out of the delivery conduit and/or retracting the delivery conduit to thereby expand the implant to the expanded second shape and to leave the implant in place in the nasal tissue, wherein the expanded second shape of the resiliently deformable portion corresponds to an orientation of the implant within the delivery conduit orientating portion; and
removing the delivery conduit from the patient,
wherein the resiliently deformable portion comprises two tines and the expanded second shape includes each end of the two tines pointing from the first end of the implant away from a second end of the implant that opposes the first end of the implant.

30. A method of implanting an implant into a nasal tissue of a patient, the implant comprising a first end including a resiliently deformable portion configured to have a contracted first shape with a non-circular cross-section and an expanded second shape, the method comprising:
providing the implant in the contracted first shape close to a distal end of a delivery conduit of a housing, the delivery conduit comprising an interior orienting portion with a cross-sectional shape configured to orient the implant relative to the delivery conduit;
piercing a nasal tissue with a piercing end of the delivery conduit by moving the delivery conduit through the nasal tissue;
advancing the implant out of the delivery conduit and/or retracting the delivery conduit to thereby expand the implant to the expanded second shape and to leave the implant in place in the nasal tissue, wherein the expanded second shape of the resiliently deformable portion corresponds to an orientation of the implant within the delivery conduit orientating portion; and
removing the delivery conduit from the patient,
wherein the resiliently deformable portion of the expanded second shape points from the first end of the implant away from a second end of the implant that opposes the first end of the implant.

* * * * *